US 6,416,471 B1

(12) United States Patent
Kumar et al.

(10) Patent No.: US 6,416,471 B1
(45) Date of Patent: Jul. 9, 2002

(54) PORTABLE REMOTE PATIENT TELEMONITORING SYSTEM

(75) Inventors: Harpal S. Kumar, Cambridge; Paul Johnson, Oxford; Michael D. Llewellyn, Cambridge; William J. Mullarkey, Wigan, all of (GB); William New, Jr., Woodside, CA (US); Laurence J. Nicolson, Liverpool (GB); William G. O'Brien, Herts (GB); John D. Place, Suffolk (GB); Peter M. Relph, Essex (GB)

(73) Assignee: Nexan Limited, Cambridge (GB)

( * ) Notice: Subject to any disclaimer, the term of this patent is extended or adjusted under 35 U.S.C. 154(b) by 0 days.

(21) Appl. No.: 09/292,405

(22) Filed: Apr. 15, 1999

(51) Int. Cl.$^7$ ................................................. A61B 5/00
(52) U.S. Cl. ........................ 600/300; 600/301; 128/903; 128/904
(58) Field of Search ................................ 600/300–301, 600/481–486, 500–508, 529–538, 544–545; 128/903, 904, 900, 920–925

(56) References Cited

U.S. PATENT DOCUMENTS

| 2,298,125 A | 10/1942 | Hartman |
| 2,660,165 A | 11/1953 | Miller |
| 3,212,496 A | 10/1965 | Preston |
| 3,409,007 A | 11/1968 | Fuller |

(List continued on next page.)

FOREIGN PATENT DOCUMENTS

| CH | 293560 | 12/1953 |
| EP | 0 212 278 | 3/1987 |
| EP | 0 479 857 B1 | 12/1993 |

(List continued on next page.)

OTHER PUBLICATIONS

"Microcomputer–based Telemetry System for ECG Monitoring," *Proceedings of the Ninth Annual Conference of the IEEE Engineering in Medicine and Biology Society*, The Boston Park Plaza Hotel, Boston, MA, Nov. 13–16, 1987, vol. 3 of 4, 2 pages.

(List continued on next page.)

*Primary Examiner*—Eric F. Winakur
*Assistant Examiner*—Michael Astorino
(74) *Attorney, Agent, or Firm*—Woodcock Washburn Kurtz Mackiewicz & Norris LLP

(57) ABSTRACT

A system and method for monitoring vital signs and capturing data from a patient remotely using radiotelemetry techniques. The system is characterized by a cordless, disposable sensor band with sensors form measuring full waveform ECG, full waveform respiration, skin temperature, and motion, and transmission circuitry for the detection and transmission of vital signs data of the patient. A small signal transfer unit that can either be worn by the patient, e.g., on his or her belt, or positioned nearby receives data from the sensor band, which it then forwards by e.g., radio transmission to a base station that can be located up to 60 meters away. The base station receives data transmissions from the signal transfer unit and is designed to connect to conventional phone lines for transferring the collected data to a remote monitoring station. The base station may also capture additional clinical data, such as blood pressure data, and to perform data checks. Patient safety is enhanced by the ability of the base station to compare clinical data, e.g., ECG, against given profiles and to mark events when appropriate or when the base station is programmed to do so. Such events are indicated to the physician and could be indicated to the patient by reverse transmission to the signal transfer unit. A remote monitoring station allows the presentation and review of data (including events) forwarded by the sensor band. ECG analysis software and a user-friendly graphical user interface are provided to remotely analyze the transmitted data and to permit system maintenance and upkeep. The system of the invention has useful application to the collection of patient clinical data during drug trials and medical testing for regulatory approvals as well as management of patients with chronic diseases.

90 Claims, 24 Drawing Sheets

U.S. PATENT DOCUMENTS

| | | |
|---|---|---|
| 3,572,316 A | 3/1971 | Vogelman et al. |
| 3,572,322 A | 3/1971 | Wade |
| 3,603,881 A | 9/1971 | Thornton |
| 3,757,778 A | 9/1973 | Graham |
| 3,848,582 A | 11/1974 | Milani et al. |
| 3,858,576 A | 1/1975 | Dehnert et al. |
| 3,882,277 A | 5/1975 | DePedro et al. |
| 3,902,478 A | 9/1975 | Konopasek et al. |
| 3,908,641 A | 9/1975 | Judson et al. |
| 3,943,918 A | 3/1976 | Lewis |
| 3,986,498 A | 10/1976 | Lewis |
| 4,023,564 A | 5/1977 | Valiquette et al. |
| 4,082,087 A | 4/1978 | Howson |
| 4,121,573 A | 10/1978 | Crovella et al. |
| 4,121,575 A | 10/1978 | Mills et al. |
| 4,122,843 A | 10/1978 | Zdrojkowski |
| 4,141,351 A | 2/1979 | James et al. |
| 4,202,344 A | 5/1980 | Mills et al. |
| 4,233,987 A | 11/1980 | Feingold |
| 4,249,538 A | 2/1981 | Musha et al. |
| 4,319,241 A | 3/1982 | Mount |
| 4,328,814 A | 5/1982 | Arkans |
| 4,353,372 A | 10/1982 | Ayer |
| 4,356,486 A | 10/1982 | Mount |
| 4,494,553 A | 1/1985 | Sciarra et al. |
| 4,522,211 A | 6/1985 | Bare et al. |
| 4,593,284 A | 6/1986 | Clifford et al. |
| 4,606,352 A | 8/1986 | Geddes et al. |
| 4,622,979 A | 11/1986 | Katchis et al. |
| 4,658,831 A | 4/1987 | Reinhard et al. |
| 4,662,378 A | 5/1987 | Thomis |
| 4,709,704 A | 12/1987 | Lukasiewicz |
| 4,742,831 A | 5/1988 | Silvian |
| 4,763,660 A | 8/1988 | Kroll et al. |
| 4,784,162 A | 11/1988 | Ricks et al. |
| 4,827,943 A | 5/1989 | Bornn et al. |
| 4,852,572 A | 8/1989 | Nakahashi et al. |
| 4,893,632 A | 1/1990 | Armington |
| 4,909,260 A | 3/1990 | Salem et al. |
| 4,926,868 A | 5/1990 | Larsen |
| 4,955,381 A | 9/1990 | Way et al. |
| 4,957,109 A | 9/1990 | Groeger et al. |
| 4,967,748 A | 11/1990 | Cohen |
| 4,967,749 A | 11/1990 | Cohen |
| 4,981,141 A | 1/1991 | Segalowitz |
| 4,984,572 A | 1/1991 | Cohen |
| 4,986,270 A | 1/1991 | Cohen |
| 5,027,816 A | 7/1991 | Cohen |
| 5,038,782 A | 8/1991 | Gevins et al. |
| 5,050,612 A | 9/1991 | Matsumura |
| 5,069,215 A | 12/1991 | Jadvar et al. |
| 5,078,134 A | 1/1992 | Heilman et al. |
| 5,080,099 A | 1/1992 | Way et al. |
| 5,163,429 A | 11/1992 | Cohen |
| 5,168,874 A | 12/1992 | Segalowitz |
| 5,199,433 A | 4/1993 | Metzger et al. |
| 5,224,485 A | 7/1993 | Powers et al. |
| 5,228,449 A | 7/1993 | Christ et al. |
| 5,269,301 A | 12/1993 | Cohen |
| 5,279,305 A | 1/1994 | Zimmerman et al. |
| 5,307,817 A | 5/1994 | Guggenbuhl et al. |
| 5,307,818 A | 5/1994 | Segalowitz |
| 5,343,860 A | 9/1994 | Metzger et al. |
| 5,353,793 A | 10/1994 | Bornn |
| 5,372,125 A | 12/1994 | Lyons |
| 5,373,852 A | 12/1994 | Harrison et al. |
| 5,394,882 A | 3/1995 | Mawhinney |
| 5,431,171 A | 7/1995 | Harrison et al. |
| 5,456,682 A | 10/1995 | Edwards et al. |
| 5,458,124 A | 10/1995 | Stanko et al. |
| 5,462,501 A | 10/1995 | Oka et al. |
| 5,465,715 A | 11/1995 | Lyons |
| 5,511,553 A | 4/1996 | Segalowitz |
| 5,522,396 A | 6/1996 | Langer et al. |
| 5,538,005 A | 7/1996 | Harrison et al. |
| 5,544,661 A | 8/1996 | Davis et al. |
| 5,549,113 A | 8/1996 | Halleck et al. |
| 5,558,638 A | 9/1996 | Evers et al. |
| 5,564,429 A * | 10/1996 | Bornn et al. .................. 600/301 |
| 5,579,001 A | 11/1996 | Dempsey et al. |
| 5,579,775 A | 12/1996 | Dempsey et al. |
| 5,617,871 A | 4/1997 | Burrows |
| 5,634,468 A | 6/1997 | Platt et al. |
| 5,652,570 A | 7/1997 | Lepkofker |
| 5,670,944 A | 9/1997 | Myllymäki |
| 5,678,545 A | 10/1997 | Stratbucker |
| 5,682,902 A | 11/1997 | Herleikson |
| 5,687,734 A | 11/1997 | Dempsey et al. |
| 5,778,882 A | 7/1998 | Raymond et al. |
| 5,891,044 A | 4/1999 | Golosarsky et al. |
| 5,919,141 A | 7/1999 | Money et al. |
| 6,014,432 A * | 1/2000 | Modney ..................... 600/300 |
| 6,095,985 A | 8/2000 | Raymond et al. |

FOREIGN PATENT DOCUMENTS

| | | |
|---|---|---|
| EP | 0 617 914 A1 | 10/1994 |
| EP | 0 458 883 B1 | 11/1996 |
| EP | 0 760 224 A1 | 3/1997 |
| EP | 0 761 160 A1 | 3/1997 |
| EP | 0 770 349 A1 | 5/1997 |
| EP | 0 719 108 B1 | 6/1997 |
| EP | 0 796 589 A1 | 9/1997 |
| EP | 0 796 590 A1 | 9/1997 |
| EP | 0 598 016 B1 | 10/1997 |
| GB | 2 003 276 A | 3/1979 |
| GB | 2 207 579 A | 2/1989 |
| WO | WO 87/06447 | 11/1987 |
| WO | WO 90/01898 | 3/1990 |
| WO | WO 91/00054 | 1/1991 |
| WO | WO 93/02622 | 2/1993 |
| WO | WO 93/08734 | 5/1993 |
| WO | WO 93/10706 | 6/1993 |
| WO | WO 93/19667 | 10/1993 |
| WO | WO 94/01039 | 1/1994 |
| WO | WO 94/03105 | 2/1994 |
| WO | WO 94/25841 | 11/1994 |
| WO | WO 95/07048 | 3/1995 |
| WO | WO 95/07652 | 3/1995 |
| WO | WO 95/10974 | 4/1995 |
| WO | WO 96/01585 | 1/1996 |
| WO | WO 96/29005 | 9/1996 |
| WO | WO 96/38080 | 12/1996 |
| WO | WO 97/09923 | 3/1997 |
| WO | WO 97/28736 | 8/1997 |
| WO | WO 97/40747 | 11/1997 |

OTHER PUBLICATIONS

"Biomedical Telectrodes: Compact transmitters would eliminate the need for visits for wires to monitors," *NASA TechBrief*, Lyndon B. Johnson Space Center, Houston, Texas, Feb., 1990, 1 page.

* cited by examiner

|  | (i) before | (ii) after |
|---|---|---|
| (0,0) | 00001111 0 ⋯ 1 00001111 | 00001111 0 ⋯ 1 00001111 |
| (0,1) | 00001111 0 ⋯ 0 00111100 | 00001111 0 ⋯ 0 000111100000 |
| (0,2) | 00001111 0 ⋯ 0 01111000 | 00001111 0 ⋯ 0 01111000 |
| (0,3) | 00001111 0 ⋯ 1 11100001 1 | 00001111 0 ⋯ 1 111000011111 |
| (1,0) | 00111100 0 ⋯ 1 00001111 | 1111000 ⋯ 1 00001111 |
| (1,1) | 00111100 0 ⋯ 0 00111100 | 1111000 ⋯ 0 000111110000 |
| (1,2) | 00111100 0 ⋯ 0 01111000 | 1111000 ⋯ 0 01111000 |
| (1,3) | 00111100 0 ⋯ 1 11100001 1 | 1111000 ⋯ 1 111000011111 |
| (2,0) | 11110000 1 ⋯ 1 00001111 | 11110000 1 ⋯ 1 00001111 |
| (2,1) | 11110000 1 ⋯ 0 00111100 | 11110000 1 ⋯ 0 000111110000 |
| (2,2) | 11110000 1 ⋯ 0 01111000 | 11110000 1 ⋯ 0 01111000 |
| (2,3) | 11110000 1 ⋯ 1 11100001 1 | 11110000 1 ⋯ 1 111000011111 |
| (3,0) | 11000011 1 ⋯ 1 00001111 | 00001111 ⋯ 1 00001111 |
| (3,1) | 11000011 1 ⋯ 0 00111100 | 00001111 ⋯ 0 000111110000 |
| (3,2) | 11000011 1 ⋯ 0 01111000 | 00001111 ⋯ 0 01111000 |
| (3,3) | 11000011 1 ⋯ 1 11100001 1 | 00001111 ⋯ 1 111000011111 |

↓ convert to code (0,0) CNNNSNNNC ... NCNNNSNNN
(0,1) CNNNSNNNC ... NNNSNNNCNNN
(0,2) CNNNSNNNC ... NSNNNCNNN
(0,3) CNNNSNNNC ... NNNCNNNSNNN ↓ insert case selection (0,x) → CT, NST, NC ... NCNNNSNJ
              ↘ NC ... NNNSNNNCNJ
       → NST, NC ... NSNNNCNJ
              ↘ NC ... NNNCNNNSNJ → (1,x)
→ (2,x)
→ (3,x)

N no operation
C clear output bit
S set output bit
T test and conditional jump
J jump Example assembly of regularly-sampled values into packets

| Nexoft v0.39 Monitoring Setup |
| Patient Number: 123 |
| Group Study Code: 321 |

Monitoring and Download Schedule | Event Setup | Auxiliary Sensor Setup

This page specifies the schedule for patient monitoring and the schedule for downloading data from the Base Station.

Monitoring days
- ● Monitor every day
- ○ Monitor only on these days  ☑ Monday  ☑ Tuesday  ☑ Wednesday  ☑ Thursday
  ☑ Friday  ☑ Saturday  ☑ Sunday

Monitoring times
- ● Monitor at [14:00:00]          [19:00:00]
- ○ Monitor every [1 ▶] hour(s) at [00 ▶] minute(s) past the hour, starting at [00:00:00]
- Monitor for [1 ▶] hour(s) and [00 ▶] minute(s)

Download days
- ● Download every day
- ○ Download only on these days  ☑ Monday  ☑ Tuesday  ☑ Wednesday  ☑ Thursday
  ☑ Friday  ☑ Saturday  ☑ Sunday

Download time
Download data from patient at [00:00:00]

[Save Changes]
[Undo Changes]

[Print]   [Close]

Auxiliary Sensor Changes Saved.   01/04/99   19:20

PORTABLE REMOTE PATIENT TELEMONITORING SYSTEM

BACKGROUND OF THE INVENTION

1. Field of the Invention

The present invention relates to a system and method for monitoring vital signs and capturing data from a patient remotely using radiotelemetry techniques. In particular, the present invention is a low cost, patient-friendly, ambulatory monitoring system for remote electronic capture of nonincasive vital signs data including, e.g., full waveform ECG, repiration rate, skin temperature, and blood pressure. The present invention also has the capability for real-time monitoring or recording of continuous or point-in-time information with the data presented to the user in a tailored form. Monitoring software included in the system of the invention may also incorporate full ECG analysis as well as alarms for arrhythmias and other abnormalities determined from the measured vital signs.

2. Description of the Prior Art

Before drugs and related therapies are approved for widespread use by physicians, such drugs and therapies typically undergo numerous trials for efficacy and safety. Successful human trials are critical to regulatory approval of a new drug or therapy, and accordingly, much money an effort goes into the human trials. At present, patients are selected for the trial and placed on the regimen under test. The efficacy and safety of the drug and/or therapy is tested by having the patient make numerous visits to his or her physician for testing during the trial period. While a great deal of information can be gathered at such tests, generally there is no method for collecting the data between physician visits, thereby causing decisions regarding efficacy and safety to be made based on a small sampling of the patients' experiences with the drug and/or therapy. More frequent visits to the physician would improve the data pool; unfortunately, such visits are expensive, add to the overall cost of the trial, and, because a limited data set is available, the trial duration is lengthened, thereby delaying the drug's market introduction.

An improved technique for testing the efficacy and safety of a drug and/or therapy is desired which does not require additional visits to the physician. It is desired to develop a technique for collecting data from a human subject at all times during a trial without requiring any visits to the physician's office, thereby eliminating the cost and inconvenience of visiting the physician's office for routine monitoring.

Also, an improved remote patient monitoring/management system is generally desired whereby useful vital signs data may be obtained from a patient without requiring frequent visits to the physician's office. Such remote monitoring/management is particularly desirable for home patient monitoring of patients with chronic illnesses such as congestive heart failure of for post-operative or out-patient monitoring. Prior art patient telemetry systems have had limited commercial success for a variety of reasons such as difficult of use and cost.

Remote patient monitoring techniques are generally known in which electrodes are placed on the patient to monitor the patient's vital signs and the captured data is transmitted to a remote display for monitoring the patient's condition. Remote monitoring systems are known which permit a doctor or nurse to monitor the conditions of several hospitalized patients from a central monitoring site in the hospital. Typically, sophisticated patient monitoring equipment is used to collect data from the patient, and the collected data is transmitted via wire to the central monitoring site in the hospital. Generally, wireless systems are problematic in the hospital setting because of the proximity of the respective patients and the amount of interference found in such a setting.

Typically, most of the patients receiving a particular drug regimen or therapy being tested are ambulatory and, in many cases, participating in the study from home. Remote monitoring of patients from their homes introduces an entirely new set of challenges for transmitting the gathered data to a central location for evaluation. Numerous attempts have been made to facilitate such data collection and trasmission; however, in each case, cumbersome and uncomfortable monitoring equipment is placed on the patient and the patient is tethered to the monitoring equipment by electrical cords, thereby limiting the patient's movement. In some prior art systems, the electrical cords have been removed and the transmissions to the monitoring equipment made using telemetry techniques; however, such systems have been used primarily for real-time vital signs monitoring and not for data collection of the type needed for diagnosis and efficacy and safety testing. Moreover, such systems also limited the movement of the patient to a limited area near the vital signs monitor.

For example, an early telemetry system is described is U.S. Pat. No. 3,603,881 in which short transmission distances to a building's wiring system are covered using VHF transmission. Physiologic data such as electrocardiographic (ECG) data is collected by a sensor and transmitted by a VHF transmitter to a fixed VHF receiver RF transmitter coupled to the wiring system in the building. An RF receiver demodulator monitor is coupled to the building's wiring system at the nurse's station for receiving the physiologic data for patient monitoring and/or data recording.

A similar telemetry system for monitoring ECTG signals is described in U.K. Patent Application No. 2 003 276 except that telephone connections are used in place of the building wiring and the system is also designed to collect blood pressure, pulse rate, respiratory rate and the like and to relate that information to the physician via the telephone connections.

Other early telemetry systems of the type described by Lewis in U.S. Pat. No. 3,943,918 and by Crovella et al. in U.S. Pat. No. 4,121,573 use telemetric techniques to transmit data from a sensor device attached to the patient's chest via RF to a radio telemetry receiver for display and/or recording as desired. S.S. Ng described yet another telemetry system for ECG monitoring in an article entitled "Microprocesor-based Telemetry System for ECG Monitoring," IEEE/Ninth Annual Conference of the Engineering in Medicine and Biology Society, CH2513-0, pages 1492–93 (1987). Ng therein describes a system for providing continuous ECG monitoring and analysis by means of a PC AT via wireless link. In the Ng system, the patient requires a transmitter which is carried by the patient for sensing and transmitting the patient's ECG signal to a central base station via wireless link. At the base station, a receiver recovers the original ECG signal from a few patients simultaneously for display.

Each of the above-described telemetry systems is designed primarily for hospital use and include relatively expensive sensor arrays and processing devices for real-time patient monitoring and diagnosis. The real-time monitoring is generally used in an "alarm" mode to capture events, rather than to collect data over a period of time to determine trends which might indicate a more gradual deterioration or improvement in the patient's condition or to predict a forthcoming event. Also, these systems require the patient to remain in close proximity to the base stations including the receivers.

Bornn et al. describe a portable physiological data monitoring/alert system in U.S. Pat. Nos. 4,784,162; 4,827,943; 5,214,939; 5,348,008; 5,353,793; and 5,564,429 in which one or more patients wear sensor harnesses including a microprocessor which detects potentially life-threatening events and automatically calls a central base station via radiotelemetry using a radio modem link. In a home or alternate site configuration, communications between the base station and remote unit is by way of commercial telephone lines. Generally, the system automatically calls "911" or a similar emergency response service when an abnormality is detected by the ECG monitor.

Unfortunately, the sensor harness is quite cumbersome and conspicuous and includes sensors for performing an alert function rather than data collection and analysis functions.

Segalowitz discloses a wireless vital signs monitoring system in U.S. Pat. Nos. 4,981,141; 5,168,874; 5,307,818; and 5,511,553 including a precordial strip patch including a multi-layer flexible structure for telemetering data by radio frequency or single wire to hardware recording apparatus and a display monitor. Microsensors and conductive contact elements (CCEs) are mounted on the strip patch so as to permit simultaneous and continuous detection, processing and transmission of 12-lead ECG, cardiac output, respiration rate, peripheral blood oximetry, temperature of the patient, and ECG fetal heart monitoring via a single wavelength of radio frequency transmission. While the precordial strip patch used by Segalowitz purportedly transmits vital signs data up to 50 meters, it requires a dual-stage operational amplifier chip, an encoder modulator chip, a wireless transmitter chip including an oscillator, and other costly components such as artificial intelligence software, sound and visual alarms, and a microprocessor. As a result, the precordial strip patch is relatively expensive to manufacture and operate. Also, as with the other telemetry systems noted above, the emphasis of Segalowitz is on real-time monitoring and alerting of medical personnel to immediate medical needs of the patient.

Platt et al. also disclose a sensor patch for wireless physiological monitoring of patients in U.S. Pat. No. 5,634,468. Platt et al. describe a sensor and system for monitoring ECG signals remotely from patients located in non-hospital sites. In this system, a sensor patch containing sensing electrodes, signal processing circuitry and radio or infra-red transmission circuitry is attached to the patient's body and preferably worn for at least a week before its power supply is exhausted and the sensor patch is thrown away. A receiver at a primary site in the vicinity of the patient receives the data transmitted by the sensor patch and stores the sensed data. When the patient feels discomfort or concern, or if the portable unit sounds an alarm, the patient telephones the monitoring station and downloads the stored data from the portable unit via the standard voice telecommunications network. The downloaded ECG data is then monitored and analyzed at the monitoring station. The receiver in the proximity of the patient may be a portable unit carried around by the patient, where the portable unit includes a receiver, a processor for processing the received data to identify abnormalities, a memory for storing the sensed data, and circuitry for interfacing to a telephone line to send the ECG data signals to the monitoring station. The monitoring station decodes the received ECG signals and performs beat and rhythm analysis for classification of the ECG data. If an abnormal condition is discovered, medical personnel in the vicinity of the patient are contacted. While the system described by Platt et al. may collect ECG data from the patient and process it at a remote monitoring station, the data is only collected when the patient initiates the data download. Otherwise, data is lost once the memory in the portable unit is full. No mechanism is provided for continuously collecting data, at all times, in a way which requires no patient action.

In U.S. Pat. No. 5,522,396, Langer et al. disclose a telemetry system for monitoring the heart of a patient in which a patient station includes telemetering apparatus for transmitting the outputs of patient electrodes to a tele-link unit connected to a monitoring station by telephone lines. As in the Platt et al. system, Langer et al. transmit ECG data to a central location. However, unlike the Platt et al. system, the Langer et al. system checks the ECO data for predetermined events and automatically calls the monitoring station when such events are detected. A similar telemetry system is described by Davis et al. in U.S. Pat. No. 5,544,661 which initiates a cellular phone link from the patient to the central monitoring location when an event is detected. As with the Platt et al. system, neither of these systems provides a mechanism for continuously collecting data without patient action.

Accordingly, a telemetry system is desired which collects vital signs data from a patient using an inexpensive device which permits the continuous collection of a patient's vital signs data without patient action. Also, a data management system is desired which permits the collected data to be reviewed and formatted for use in patient trials and the like. The present invention has been designed to meet these needs in the art.

SUMMARY OF THE INVENTION

The present invention meets the above-mentioned needs in the prior art by providing a portable remote patient telemonitoring system having four separate elements, each with different functions within the system.

The system of the invention is characterized by a first component, an adhesive, cordless, disposable sensor band with electrode patches, other sensors, and transmission circuitry for the detection and transmission of vital signs data. The sensor band is easy-to-use and is positioned on the patient by the patient. The sensor band is designed to be worn comfortably by the patient for 24 hours, at which time the sensor band may be discarded and replaced by a new sensor band.

The system of the invention is further characterized by a second component, a small signal transfer unit that can either be worn by the patient, e.g., on his or her belt, or positioned nearby (within approximately 1.5 meters), e.g., on a desk or chair or at the bedside. The function of the signal transfer unit is to receive data from the sensor band, which it then forwards by, e.g., radio transmission to a base station that can be located up to 60 meters away. The small signal transfer unit is designed to minimize the transmission requirements of the sensor band while also allowing the patient to move around freely while his or her vital signs are being monitored.

A third component, a base station, receives data transmissions from the signal transfer unit and is designed to connect to conventional phone lines for transferring the collected data to a remote monitoring station. The base station may also be designed to capture additional clinical data, such as blood pressure data, and to perform data checks. For data transfer, the base station connects the output of the sensor band, via modem and land or cellular telephone line, to the remote monitoring station. Connections for auxiliary sensors such as a blood pressure cuff extend the number of clinical parameters that can be captured. Patient safety is enhanced by the ability of the base station to compare clinical data, e.g. ECG, against given profiles and to raise alarms when appropriate or when the base station is programmed to do so. Such alarms could be indicated to the patient by reverse transmission to the signal transfer unit.

The fourth component, a remote monitoring station, allows the presentation and review of data (including event flags) forwarded by the sensor band and other sensors and simply requires a standard PC running, e.g., Windows NT. ECG analysis software and a user-friendly graphical user interface are provided to remotely analyze the transmitted data and to permit system maintenance and upkeep.

In preferred embodiments, the patient vital signs data collection and monitoring system of the invention is characterized by a sensor band having a sensor assembly for application to a patient. The sensor assembly produces a data signal including vital signs data indicative of values of at least one vital sign of the patient, and the sensor band further comprises a transmitter which transmits the data signal over a first communications link to a transceiver coupled to the first communications link so as to receive the vital signs data for retransmission of the data signal over a second, wireless communications link. A remote monitoring station is also provided which is disposed so as to receive the retransmitted data signal from the transmitter via the second communications link, where the remote monitoring station is characterized by its ability to capture the vital signs data for display and subsequent access and processing of the vital signs data for medical diagnosis or analysis.

In a preferred embodiment, the transceiver includes a buffer which stores vital signs data received from the sensor band at least during times when the second communications link is disconnected, lost, or unreliable. Also, the sensor band preferably comprises a transmitter having a first antenna which transmits the data signal over the first wireless communications link to a transceiver having a second antenna inductively coupled to the first communications link so as to form a wireless inductive loop with the first antenna for reception of the vital signs data. Also, in a preferred embodiment, the remote monitoring station captures the vital signs data and stores it in a database with vital signs data from a plurality of other patients. A user interface provides access to the vital signs data in the database for processing, medical diagnosis and/or analysis.

In presently preferred embodiments, the sensor band measures full waveform single or multiple lead ECG, full waveform respiration, skin temperature, and motion and transmits the measured data to the signal transfer unit, where the data is retransmitted to the base station. Auxiliary sensors may be provided at the base station including a blood pressure cuff, a spirometer, and weight scales. Also, the user interface at the remote monitoring station may contain full ECG analysis software covering waveform measurements, interval measurements, beat-typing and arrhythmia detection. "Event flags" also may be generated and indicated to the physician for high and low heart rate, high and low respiration rate, high and low temperature, high and low blood pressure or arrhythmias.

While there are many potential patient management applications for the remote telemetry system of the invention, such as remote measurement of cardiovascular abnormalities including hypertension, congestive heart failure, arrhythmia, silent ischaemia, and the like, and respiratory abnormalities including chronic obstructive pulmonary disease, in a presently preferred implementation of the invention, the remote telemetry system of the invention is also designed to reduce both the length and the cost of clinical drug trials by providing versatility in data collection with respect to site (in-clinic or domiciliary), time, and volume, and to provide direct, electronic data capture, which can be real-time if necessary. Additional applications include the monitoring of sleep apnea, diabetes, acute or sub-acute infection, asthma, and the like. The system of the invention may be used in a clinic or hospital setting but, when used in such settings, must be designed to minimize interference between radio signals.

Corresponding methods of collecting a patient's vital signs data using the remote telemetry system of the invention are also described and claimed herein.

BRIEF DESCRIPTION OF THE DRAWINGS

The above and other objects and advantages of the invention will become more apparent and more readily appreciated from the following detailed description of presently preferred exemplary embodiments of the invention taken in conjunction with the accompanying drawings of which:

FIG. 7A illustrates waveform templates which begin with a state change and end with a period free of state changes.

FIG. 7B illustrates the method by which idle periods between changes are converted into a sequence of no-operation instructions such that the correct time delays between changes are introduced.

FIG. 16B illustrates the case home screen listing the events which occurred for the selected patient during the selected time interval.

FIG. 16C illustrates the monitoring setup change screen available for the selected patient.

FIG. 16D illustrates the patient information listing the patient data for the selected patient.

FIG. 16E illustrates the auxiliary sensors setup screen available for the selected patient.

DETAILED DESCRIPTION OF PRESENTLY PREFERRED EMBODIMENTS

A system and method with the above-mentioned beneficial features in accordance with a presently preferred exemplary embodiment of the invention will be described below with reference to FIGS. 1–17. It will be appreciated by those of ordinary skill in the art that the description given herein with respect to those figures is for exemplary purposes only and is not intended in any way to limit the scope of the invention. All questions regarding the scope of the invention may be resolved by referring to the appended claims.

I. System Overview

Figure 1:
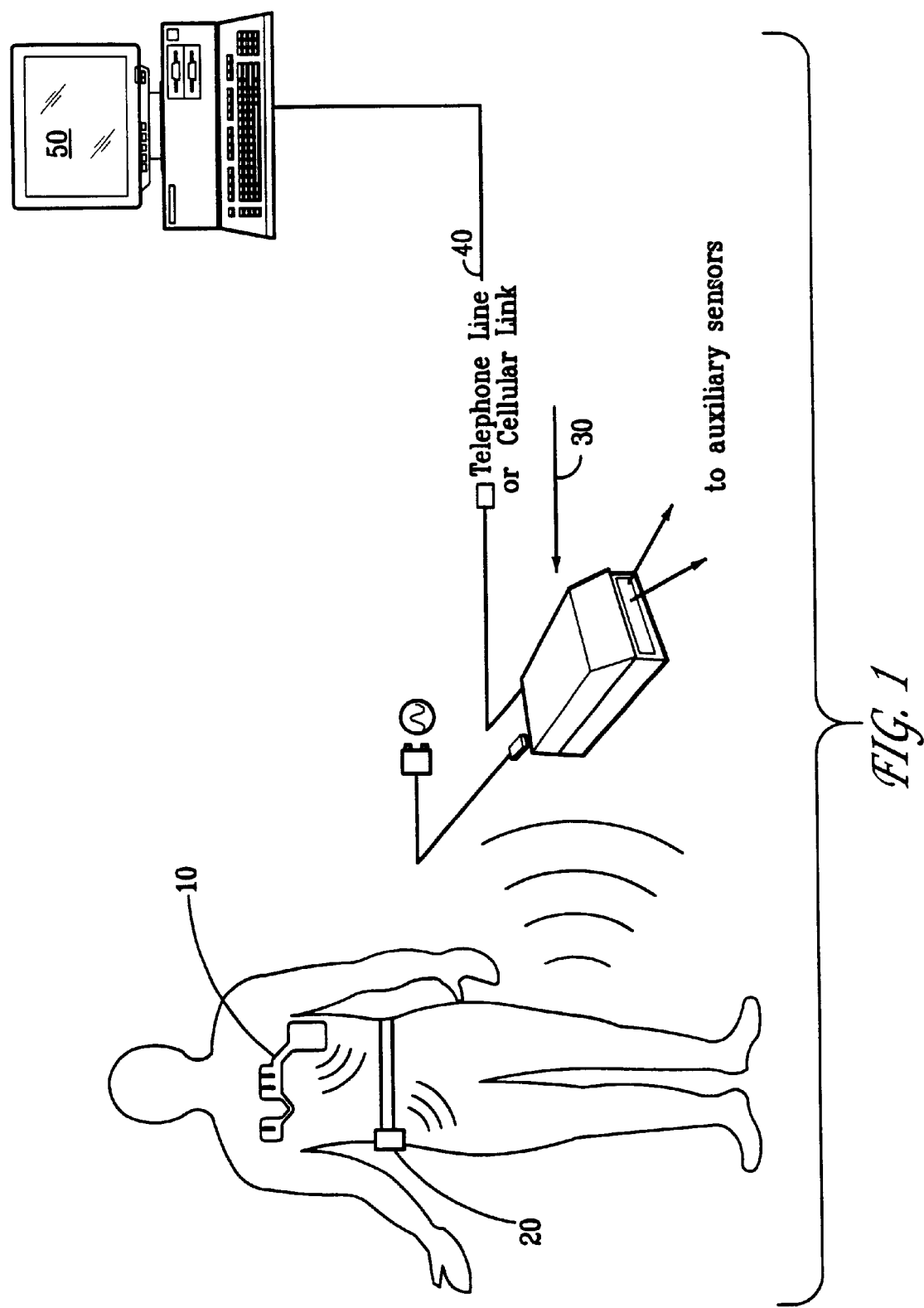
FIG. 1 illustrates a presently preferred embodiment of the remote patient monitoring system in accordance with the invention.

A presently preferred embodiment of the remote patient telemonitoring system of the invention is illustrated in FIG. 1. As illustrated, the system of the invention comprises a disposable multi-parameter sensor band 10, preferably worn on the patient's chest, for measuring patient vital signs and transmitting the measured vital signs data, a signal transfer unit 20 in proximity to the sensor band 10 for storing and retransmitting the measured vital signs data, a base station unit 30 which receives the retransmitted vital signs data and transmits the vital signs data over a telecommunications link 40, and a remote monitoring station 50 which receives the vital signs data from the base station unit 30 via the telecommunications link 40. The operation of each of the components of the system will be described in more detail below.

A. Multi-Parameter Sensor Band

Figure 2:
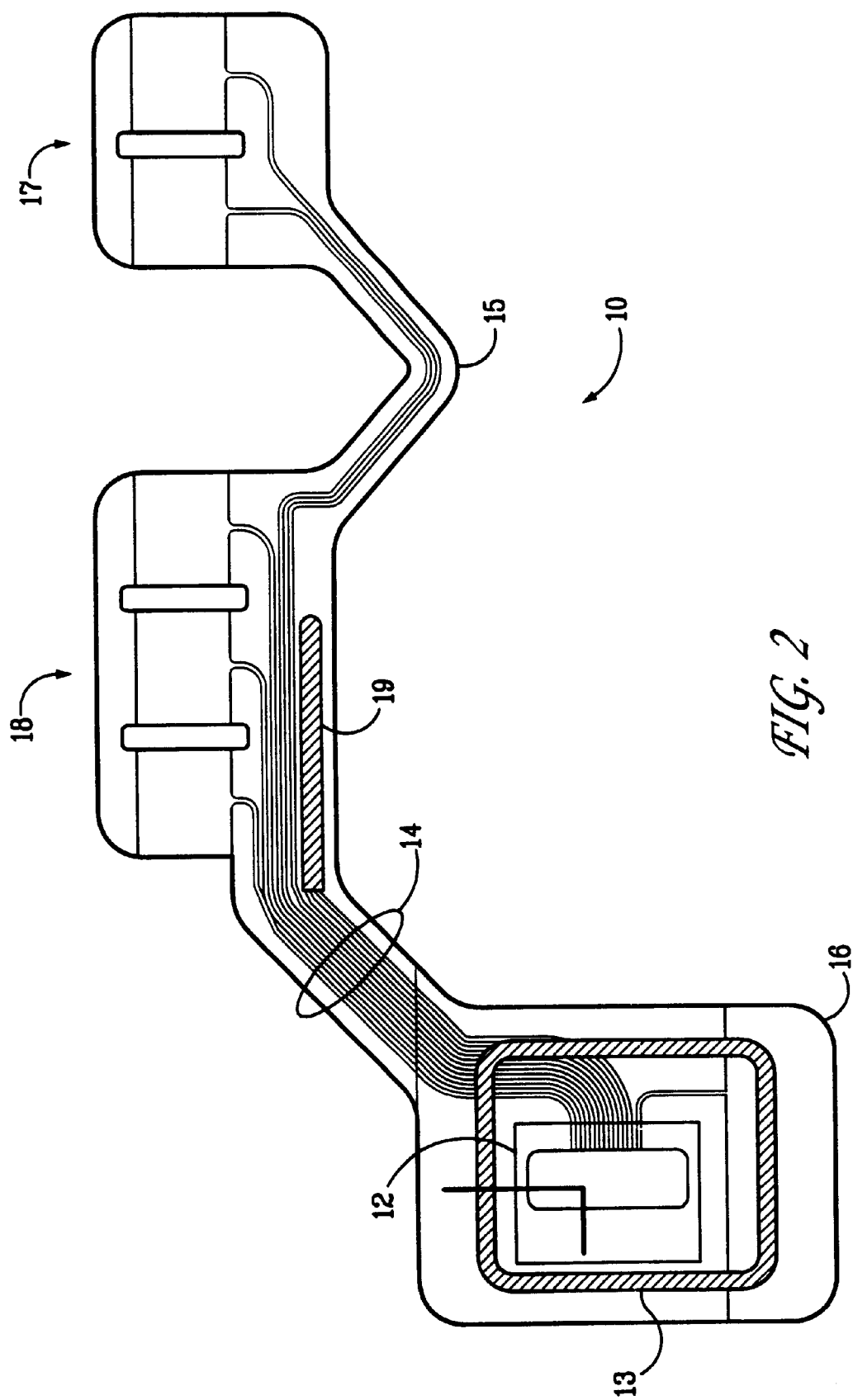
FIG. 2 illustrates a sensor band including electrodes and sensors for attachment to the patient's body for measuring and transmitting vital signs data such as full waveform single or multiple lead ECG, full waveform chest respiration, skin temperature, and motion using the techniques of the invention.

As illustrated in FIG. 2, the sensor band 10 is designed to extend across the patient's chest and includes electrodes and other sensors (not shown) which are situated so as to measure full waveform single or multiple lead ECG, full waveform chest respiration (using impedance and/or resistance bend sensor), skin temperature, and motion. Of course, other vital signs, such as EEG and blood oxygenation, could be measured as desired using sensors included within the existing sensor band and placed either on the chest or elsewhere on the body, or using sensors in another sensor band placed either on the chest or elsewhere on the patient's body. Conventional blood oxygenation sensors placed on the finger, wrist, or ear may also provide data through a wire or wireless link to the sensor band 10 or signal transfer unit 20. The signal processing and transmission circuitry 12 receives the sensor data from traces 14 and a directly connected thermistor (not shown) and is powered by, e.g., a zinc-air battery pack (not shown) designed to permit the sensor band 10 collect and transmit vital signs data for approximately 30 hours. The sensor band 10 is typically removed and disposed of every 24 hours and replaced by a new sensor band 10. Upon power up of the new sensor band 10, the serial number of that sensor band 10 is randomly generated and sent in a repeating cycle. The transmission circuitry 12 in the sensor band 10 includes a transmission antenna 13 which transmits digitized signal samples continuously via a wireless link to signal transfer unit 20, which is preferably within 1.5 meters distance. Alternatively, a back-up wire transmission link may be provided to the signal transfer unit 20; however, such a wire transmission link is not preferred because of the inconvenience to the patient. The sensor band 10 is designed such that the patient only has to prepare his or her skin, peel back a protective strip over the hydrogel and hydrocolloid adhesive layers which are, in turn, placed over the electrodes, signal processing and transmission circuitry 12, and battery, and stick the sensor band 10 to the prepared skin in a position for measurement of the vital signs such as ECG. The sensor band 10 may be provided in a number of sizes sufficient to administer to infants as well as large adults. The "V" bend 15 is preferably located between the left and right chest sections so as to allow some movement of the sensor band 10 when it is attached to the chest.

In a presently preferred embodiment, full waveform ECG data is collected at a 250 Hz sampling frequency from three electrodes: one electrode in portion 16 placed under the patient's left armpit, one electrode in a portion 17 on the right hand side of the chest, and one reference electrode in portion 18 on the left hand side of the chest. The ECG data is collected with a resolution of 10 bits.

Full waveform respiration data is also collected at a 25 Hz sampling frequency using the trans-thoracic impedance method, with a 50 kHz continuous reciprocating current and two electrodes (force and sense) at the left hand side of the chest and two electrodes at the right hand side of the chest. The sense electrode on the right hand side of the chest is preferably the same as that used for ECG detection. The respiration data has a data resolution of 8 bits. Respiration data (with the same qualities except for 7 bit resolution) may also be collected using a printed carbon on flextrate resistance bend sensor 19 located on the left hand side of the chest. One or both methods of respiration measurement may be used for a given patient.

Skin temperature data is collected at 25 Hz using a thermistor located in portion 16 under the armpit. The temperature range is 25 to 45 degrees C. with a reporting accuracy of +/−0.5 degree C., an output sampling frequency of 25 Hz, and data resolution of 6 bits.

Motion data is collected at 25 Hz sampling frequency using impedance sensing across the chest using the same drive electrodes as those described for respiration above. The motion data has a data resolution of 6 bits. In a preferred embodiment, the motion data may be compared to the ECG waveform and/or respiration waveform to determine if the measured data has been corrupted by movement.

In modified embodiments, additional data, such as blood oxygen saturation data either from a finger band or included within the chest sensor band 10, may also be collected and provided to the sensor band 10 for transmission.

Signal processing and transmission circuitry 12 preferably includes a single ASIC (Application Specific Integrated Circuit) that will receive, amplify, filter, and signal process the analog data from the sensors, perform analog to digital data conversion at 10 bit accuracy (with subsequent reduction for all but the ECG signal), pass the data stream to two micro-controllers which format and modulate the data stream and output it back to the ASIC; however, the functionality of one or more such micro-controllers could be implemented in the ASIC using techniques known in the art. In a preferred embodiment, the ASIC contains an H Bridge Drive circuit for output transmission of the data stream using antenna 13. The data is output from the ASIC either by a single wire (back up), or by wireless inductive transmission to the signal transfer unit 20. The ASIC and any micro-controllers of the transmission circuitry 12 are mounted on a flexible or rigid PCB which also contains passive components (resistors, capacitors etc.), a crystal, batteries, and connections. The PCB is connected to a flexible substrate which has printed circuit traces 14 providing connections to the electrodes and the antenna 13 or wire. More details concerning the design and manufacture of the sensor band 10 can be found in contemporaneously filed U.S. patent application Ser. Nos. 09/292,159, and 09/292,157, the contents of which are incorporated herein by reference.

For the wireless communications used in the preferred embodiment of the invention, the sensor band 10 uses a one-way inductive loop transmission scheme using digital frequency modulation in a 4 kHz band on channels with 6 kHz separation in the frequency range 50–150 kHz for a transmission distance of up to 2.5 meters. Preferably, the randomly-generated unique serial number of each sensor band 10 is inserted in the data transmissions for easy tracking. The transmission antenna 13 is either screen-printed on the flextrate or provided as a wire wound coil and embedded within the underarm portion 16 for location under the patient's armpit. Additional information regarding the antenna 13 may be found in the afore-mentioned related applications, while additional information regarding the inductive loop transmission scheme will be provided below.

B. Signal Transfer Unit

In accordance with a presently preferred embodiment of the invention, a patient will carry a signal transfer unit 20 to receive the vital signs data signals transmitted by the sensor band 10. The signal transfer unit 20 is designed to retransmit the received data to the base station unit 30 from a distance of up to 60 meters, but a typical range is approximately 30 meters. The signal transfer unit 20 need not be carried by the patient at all times, but must be within communications range of the sensor band 10 (unless a wire is used) in order to receive the transmitted vital signs data. The signal transfer unit 20 is small (approximately 110×65×25 mm) and is battery operated using, e.g., 4 "AA" primary or rechargeable cells, or a rechargeable battery pack designed to last for a minimum of 30 hours. Preferably, the signal transfer unit 20 has a clip for attachment to a waist belt and/or a holster for easy carrying by the patient.

The signal transfer unit 20 has a memory buffer which is used in the case of a loss of radio connection with the base station unit 30. This memory buffer is capable of storing vital signs data from the sensor band 10 for a period of time determined by the size of the memory buffer. The memory buffer thus allows the patient increased mobility by allowing the patient to move out of range of the base unit 30 for some period of time, preferably at least an hour (one hour of storage would require a 2 MB buffer using the sampling rates described herein and no data compression). The present inventors contemplate that, as memory options expand and costs continue to fall, the signal transfer unit 20 may be designed to include enough memory to permit the patient to move out of range of the base station unit 30 for even longer (e.g., 24 hours) without losing any data. Preferably, the signal transfer unit 20 automatically shuts down its transmission circuitry when it is out of range of the base station unit 30 in order to save energy. In this case, the signal transfer unit 20 keeps trying to reconnect to the base station unit 30 until it is back in range. Generally, the memory buffer will operate in FIFO data transfer mode and the signal transfer unit 20 will transmit data at a rate substantially faster than it is received so that the memory buffer may be emptied once the signal transfer unit 20 comes back into range of the base unit 30. However, the inventors contemplate that, in another embodiment, if an alarm condition is detected in the received data by the base station unit 30, the most recent data could be transmitted to the base station unit 30 first. Also, if the memory buffer should become full at any point, the earliest data in the memory will be replaced with the latest data.

Figure 3:
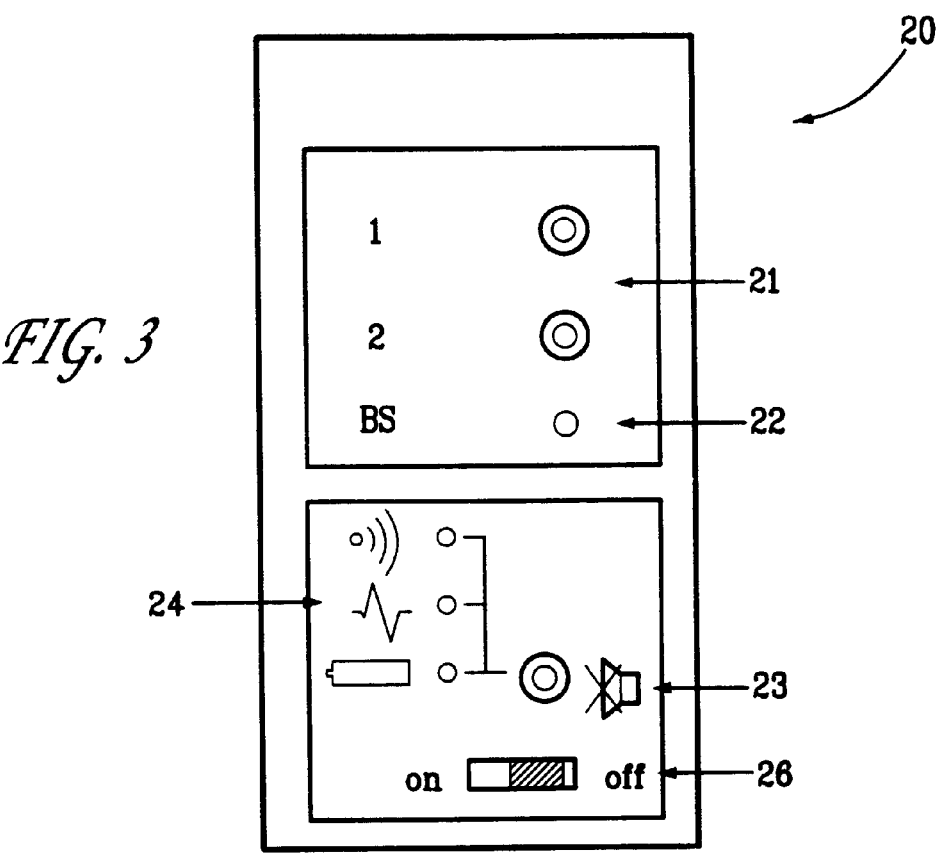
FIG. 3 illustrates the user interface to the signal transfer unit provided in accordance with the invention.

As illustrated in FIG. 3, the signal transfer unit 20 preferably provides several buttons for inputting information and displays/alarms for providing information to the patient. For example, event buttons 21 may be pressed to identify a particular event such as the taking of medication or pressed to indicate that the patient is experiencing a particular pain, feeling ill, and the like. Preferably, event buttons 21 are low profile or recessed to prevent them from being pressed accidentally. These events may be specified by the physician and agreed upon by the patient. Also, a light 22 may be illuminated when an auxiliary sensor measurement by the base station unit 30 is scheduled. A buzzer sound may also be provided as desired. A buzzer silence button 23 also may be used to silence the buzzer.

In a preferred embodiment, warning lights 24 are provided in addition to the buzzer to indicate particular conditions and/or that the system is not working properly. Such conditions include battery low in signal transfer unit 20, batteries of the signal transfer unit 20 are at the end of recharge life, no signals are being received from the sensor band 10, loss of radio contact with base station unit 30, the memory buffer in the signal transfer unit 10 is 90% full, the memory in the base station unit 30 is 90% full, time to take treatment, time to take an auxiliary sensor measurement at the base station unit 30, a physiological alarm condition has been detected in the base station unit 30, and the like. Depending on the LED "message", the patient may need to take appropriate action.

Upon starting a monitoring session, the patient will simply need to check that batteries are inserted correctly in the signal transfer unit 20, that the power on LED is lit, and that there are no warning lights 24 indicating low power, loss of contact with the base station, etc. At the end of each day, or when the patient changes the sensor band 10, he or she will need to recharge the batteries of the signal transfer unit 20 or replace them with new ones. Other than this, no action will be required on the part of the patient to operate the signal transfer unit 20. However, in the event that a wire link from the sensor band 10 is used instead of wireless transmission, the patient will need to connect the wire link from the sensor band 10 to the signal transfer unit 20.

The signal transfer unit 20 will receive the vital signs data signals from the sensor band 10 using three receiving coils (or via the wire back up link). Data packets received are CRC checked, and any packets of data not received correctly or intact by the signal transfer unit 20 are discarded. In the presently preferred embodiment, the signal transfer unit 20 will only receive data from a single sensor band 10, although a software change on the signal transfer unit 20 will enable multiple sensor bands 10 to broadcast vital signs data to a single signal transfer unit 20.

The signal transfer unit 20 may also have an internal position sensor which, when the patient is carrying signal transfer unit 20, indicates when the patient is in the horizontal position and will switch when the patient's position changes towards the vertical by more than 15 degrees. A three axis sensor or accelerometer may be used for this function. The signal transfer unit 20 may also have the facility for the connection of a microphone for recording lung or breathing sounds.

In a presently preferred embodiment, the signal transfer unit 20 transmits all data to the base station unit 30 via a half-duplex single frequency radio link using standard off the shelf radio components and a transmission rate of 40 kbps, with a frequency shift keying modulation scheme. The transmission frequency is preferably 433 MHZ in Europe and 915 MHZ in the United States and Canada. As will be explained in more detail below, the radio transmission system uses a simple low-power, high efficiency protocol, ensuring CRC error checking of data packets in the forward direction, with an instruction set enabling retransmission of erroneous packets. The system is preferably fail-safe, erring on the side of sending no data rather than erroneous data.

A more detailed description of the structure and operation of the signal transfer unit 20 of the invention may be found in contemporaneously filed U.S. patent application Ser. No. 09/292,158, the contents of which are incorporated herein by reference.

C. Base Station Unit

The signal transfer unit 20 transmits its signals via radio link to base station unit 30, which is powered by a selectable 110/230V mains power supply and includes a modem connection for a land telephone line or cellular link 40. The modem is used to send data and information to a remote monitoring station 50 at a remote telemonitoring center, which may be a physician's office or a hospital. In using the base station unit 30, the patient will need to ensure that it is switched on and that the telephone line 40 is connected. Otherwise, the base station unit 30 operates automatically, with no further action required by the patient, other than the use of auxiliary sensors.

In a presently preferred embodiment, a base station unit 30 can only receive signals from a single signal transfer unit 20, and two base station units 30 will not be able to operate within interference range of each other unless they are frequency differentiated.

Of course, known transmission techniques such as spread spectrum, CDMA, or TDMA may be used to permit the reception of signals from a plurality of signal transfer units 20 at a single base station unit 30.

Figure 4:
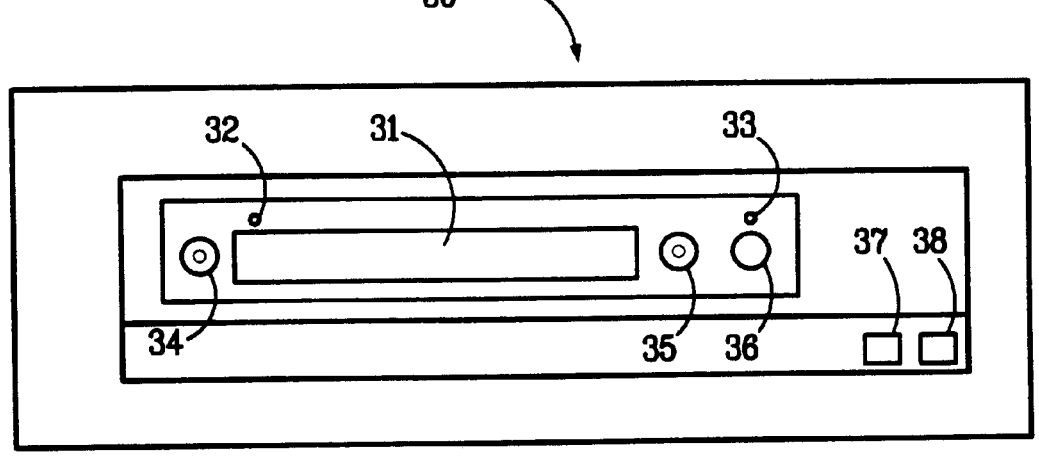
FIG. 4 illustrates the user interface to the base station unit provided in accordance with the invention.

As illustrated in FIG. 4, the base station unit 30 may include a liquid crystal display screen 31 which provides information regarding system operation and gives the patient guidance when stepping through the options for collecting data from an auxiliary sensor. A light 32 indicates that the base station unit 30 is receiving mains power. A similar light 33 may be used to indicate that the base station unit 30 is communicating with the remote monitoring station 50 via modem. An auxiliary sensor button 34 illuminates to indicate that an auxiliary sensor measurement is due, and the auxiliary sensor button 34 may be pushed to acknowledge when an auxiliary sensor measurement is about to be started and when it has been completed. A buzzer silence button 35 is preferably provided to silence the buzzer, which will sound to indicate that a message is to be read on the display screen 31. A telephone hang-up button 36 preferably breaks the communication between the base station unit 30 and the remote monitoring station 50 when depressed so that normal use of a phone connected to the same telephone line either directly or via a base station port is enabled, e.g., in emergency situations.

As noted above, the base station unit 30 preferably includes the facility for the connection of a blood pressure sensor to a connector 37 or a spirometer or weigh scales to a connector 38. The blood pressure sensor and spirometer are preferably standard commercially available units with standard RS232 digital data output streams. The base station has electrical isolation to these units. Alternatively, other point in time sensors such as a blood glucose meter could be connected to either connector 37 or 38.

During operation, the base station unit 30 will collect and store all data received from the sensor band 10. The base station unit 30 preferably has a hard disk memory, enabling storage of data until it is ready to be sent to the remote monitoring station 50. In a presently preferred embodiment, a memory having the capability of storing several days of data (at least 2 GB of memory at the sample rates described herein and assuming no data compression) is desired. Preferably, the sensor data from the sensor band 10, the event data (threshold violations, button presses, and the like), and the auxiliary measurement data (spirometer, weight scales, and/or blood pressure) are stored separately and aged independently in the memory of the base station unit 30 based on the time stamps from the sensor band 10 and/or the signal transfer unit 20. Time synchronization signals may be sent from the base station unit 30 to the signal transfer unit 20 and/or sensor band 10 to synchronize the time stamps. All data is retained in the base station memory until either it is directed to be discarded by an instruction sent from the remote monitoring station 50, or until the base station memory is full, at which point the earliest data is discarded first.

In the preferred embodiment, the base station unit further contains software algorithms which enable the calculation of heart rate and respiration rate from the ECG and respiration signals, respectively. Such algorithms include artefact detection and filtering to ensure that a high quality reading is obtained. Preferably, the algorithm for heart rate also includes a 50 Hz/60 Hz notch filter for removal of any mains noise. The base station may further contain a look-up table to convert signals received from the thermistor of the sensor band 10 into an accurate temperature reading.

The base station unit 30 may also include software which compares the various vital signs data signals received with pre-programmed thresholds for certain physiological variables. In particular, the base station unit 30 may look for threshold violations; however, the actual processing for determining whether an "event" has occurred is performed when processing the raw data at the remote monitoring station 50. Where data points fall outside these threshold values for a certain period of time, the base station unit 30 may record an event condition and could also indicate this fact to the patient by reverse radio transmission to the signal transfer unit 20 via a two-way radio link. Events are preferably generated for high or low heart rate, high or low respiration rate, or high or low temperature. The inventors also contemplate that, in alternative embodiments, events could be generated for high or low blood pressure, ischaemic events, or arrhythmias. When an event is generated, the buzzer on the base station unit 30 is sounded and the buzzer silence button 35 is illuminated. Events will also be generated at the base station unit 30 if the base station unit 30 has lost contact with the signal transfer unit 20 and/or if the memory of the base station unit 30 is full. Any or all of these situations except for loss of contact could also generate an "event" and/or an alarm in the signal transfer unit 20 through reverse transmission via the two-way radio link.

As will be explained in detail below, the base station unit 30 is preferably programmable remotely from the remote monitoring station 50 via modem or, in an alternative embodiment, locally using a laptop or PC. In the latter case, the base station unit 30 would have an interface for the optional connection of a PC or notebook computer for the display of live graphical data or for programming of the base station unit 30. The local PC or laptop could also be used for a simple video link with the remote monitoring station 50. In any case, programming of the base station unit 30 is password protected. Programming involves setting study start and stop times, setting alarm thresholds and minimum breach times, setting pre-specified dial up times for the remote monitoring station 50 to download data, setting data collection times (e.g., 5 minutes every hour), and setting times for recording data from auxiliary sensors. In this manner, the physician may choose to collect only the required data and at intervals set by the physician.

In the preferred embodiment, the remote monitoring station 50 has the ability to automatically dial in to the base station unit 30 to download data at specified times or to view real-time live data. If the line for the base station unit 30 is busy, the remote monitoring station 50 may also have the automatic ability to try again after a pre-specified period. However, the inventors contemplate that in an alternative embodiment the base station unit 30 could initiate the dial-up for uploading the stored data. Generally, the data is downloaded in a binary TCP/IP compatible protocol, providing guaranteed transmission integrity over the link with the remote monitoring station 50.

In the preferred embodiment, the base station unit 30 has a plug-in for a normal telephone so that the patient is not required to have two telephone lines. Voice communications will take precedence over data communications, i.e. the patient will be able to interrupt a data download if he or she needs to make an urgent telephone call.

In addition to the base station unit 30, each patient may be provided with a battery charger for charging the batteries of the signal transfer unit 20 if rechargeable batteries are to be used.

D. Remote Monitoring Station

At the remote monitoring station 50, a physician or nurse has access to a normal PC connected by modem to the telephone line 40. Physiological monitoring software is run on this PC or on a networked system to process the data received via the modem from the base station unit 30. Preferably, though not necessarily, the received data will incorporate the serial number of the base station unit 30, as well as the serial number of the sensor band 10, to be used for historical data tracking purposes, should this be necessary. Remote monitoring station 50 may display continuous or non-continuous data in real-time or historically and may also enable the physician to review previously stored data, to view events, and to store data to a database or other electronic file.

Figure 5A:
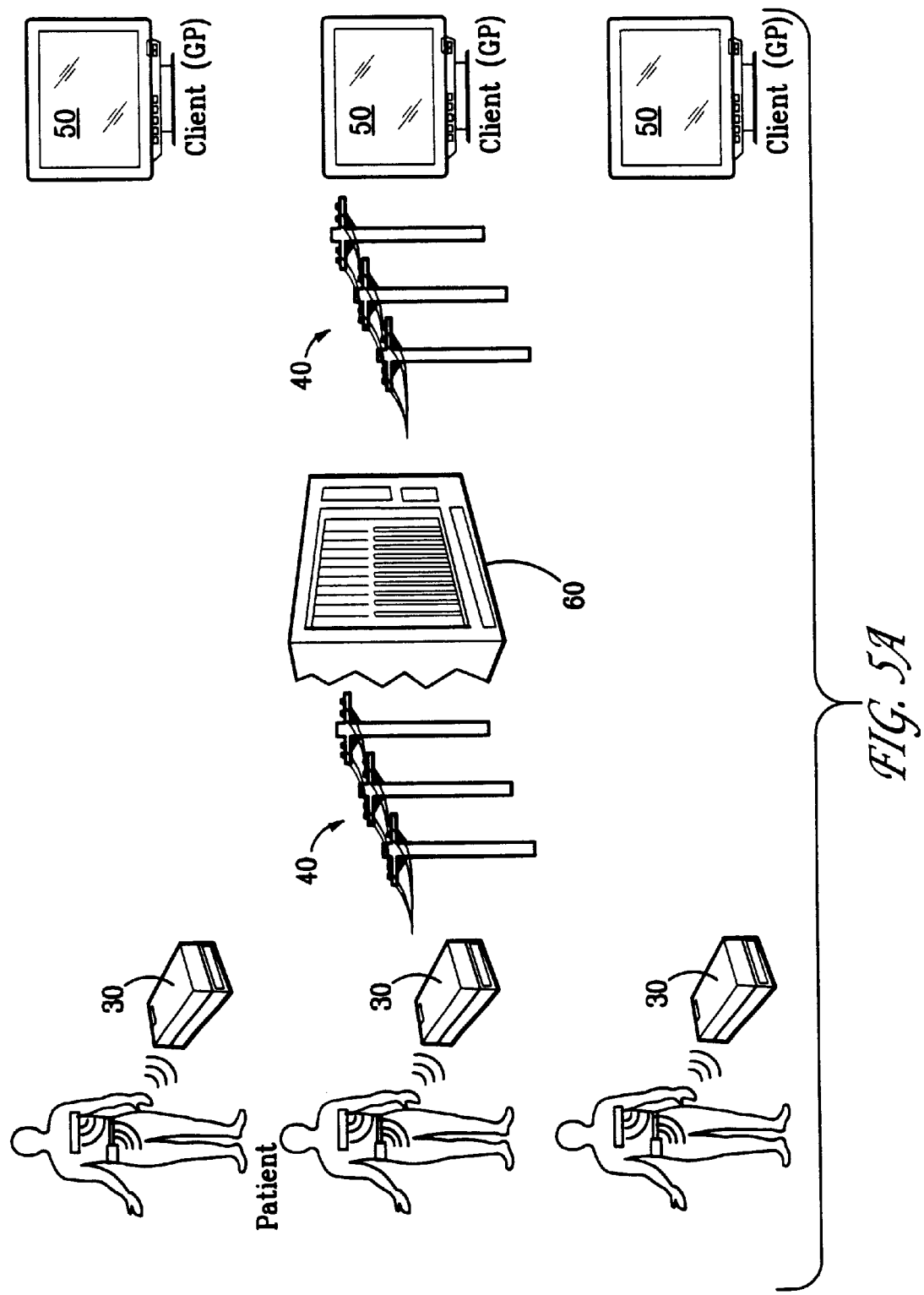
FIG. 5A illustrates a remote monitoring embodiment in which a server is used for data acquisition from a plurality of patients and providing the acquired data to client systems which are connected to access the acquired data for analysis.
Figure 5B:
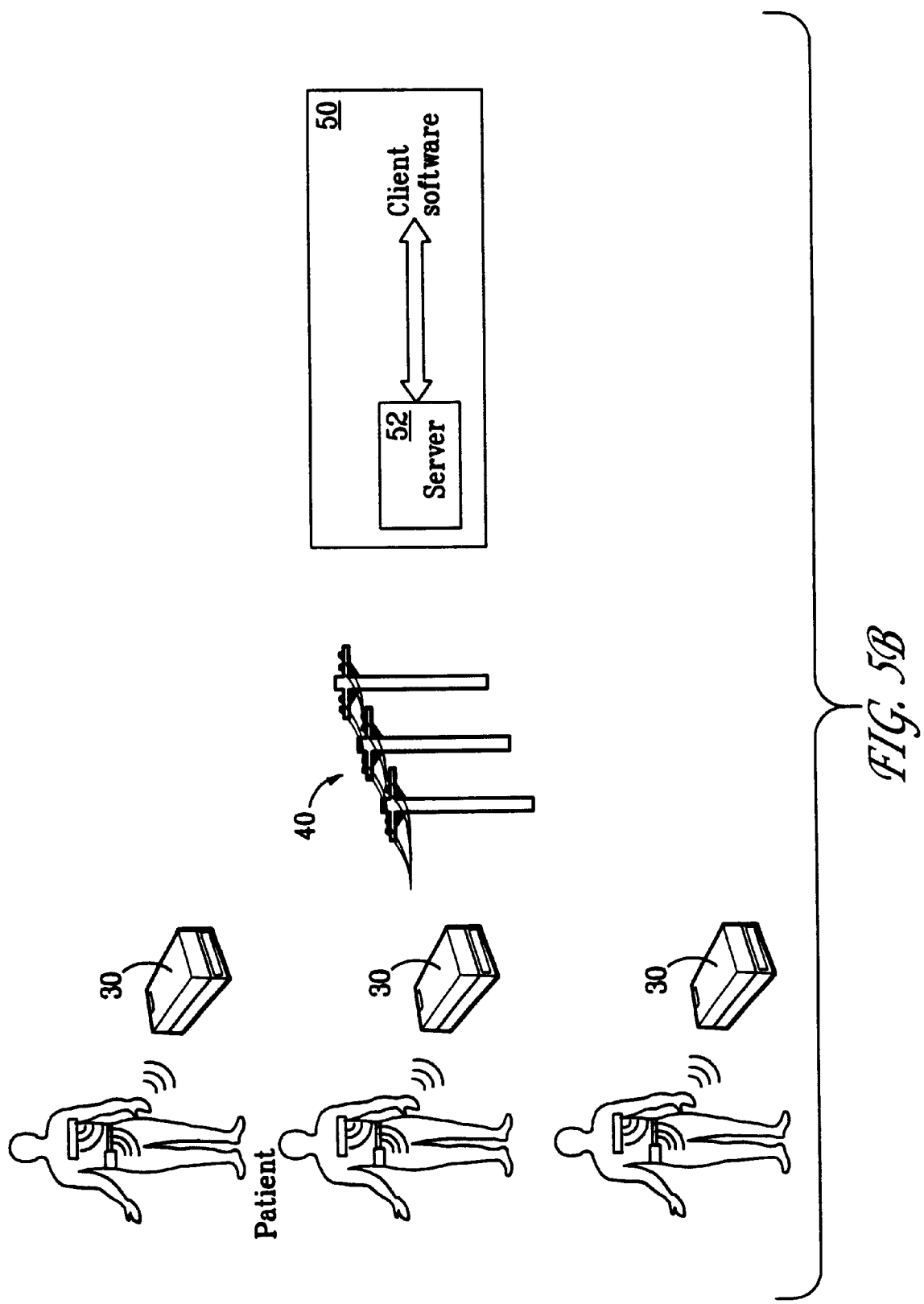
FIG. 5B illustrates a remote monitoring embodiment in which the end user has a server for data acquisition from a plurality of patients, where the end user accesses the server directly.

As illustrated in FIG. 5A, a server 60 may be located in the transmission lines 40 to permit data from a plurality of patients to be stored on the server 60 and provided to a plurality of remote monitoring stations 50 in a telemonitoring center or centers. In this case, a plurality of patients are monitored using a telemonitoring service which receives data generated and transmitted in accordance with the techniques of the invention and allows the operator at the telemonitoring center to configure studies and to analyze data. On the other hand, as illustrated in FIG. 5B, the remote monitoring station 50 may be used to simply monitor a single patient or several patients from a single remote monitoring PC running the server 52 and physiological monitoring software.

At the start of any patient study, the operator of the remote monitoring station 50 will need to configure the system's software for the type of study, e.g. real-time continuous viewing, historical data viewing, viewing of summaries, etc. The operator will also need to remotely program the base station unit 30 to collect the desired data from the patient. In some circumstances, the operator at the remote monitoring station 50 also may want to dial in to a particular base station unit 30 to check the status of a particular patient. In these instances, the operator will be able to view real-time data, even if such data is not otherwise scheduled to be downloaded by the base station unit 30 for a particular study. The operator also may download any data that has already been stored at the accessed base station unit 30. The operator will need to program a unique patient identifier at the start of a study so that data recordings can later be identified and so that patient data confidentiality can be maintained.

The inventors contemplate that under continuous real-time monitoring, the physiological monitoring software could detect alarm conditions locally and could alert the operator of the remote monitoring station 50 or of a central monitoring station on a network to this fact.

In a preferred embodiment, the remote monitoring station 50 may display several scrolling traces and several numerical measures on a single screen at any time, with the operator able to configure which traces or measures he/she wishes to see. The operator will be able to choose from a number of time bases for the review of live or historical data. Some parameters (e.g. temperature) could be shown as the latest numerical value only. The operator will also have the ability to define a data schedule enabling him/her to download selected samples of the continuous and auxiliary sensor data to the remote monitoring station 50. When a threshold event is detected by the base station unit 30, a "recording session" for later download may be flagged, causing a block of data to be recorded containing all the parameters being monitored for several (e.g. ten) minutes leading up to the event and for its duration.

If a monitoring station is provided as in the FIG. 5A or 5B embodiments, the remote operator will be able to review data from a number of patients, with data being transmitted from a number of base station units 30. When data is downloaded, events data could be sent first and could be viewed for any particular patient by the operator. The physiological monitoring software enables summaries of data to be viewed, e.g., traces of sample data points taken every 15 minutes for a particular parameter, and a display of events generated. For review of historical data, on the other hand, the physiological monitoring software will enable the operator to look at data using a choice of time-bases and a horizontal scroll bar.

In a preferred embodiment, the physiological monitoring software contains software algorithms for the analysis of the ECG signal for standard single or multiple lead ECG waveform measurements, interval measurements, beat-typing and for arrhythmia detection. These algorithms preferably include artefact detection and filtering to ensure that a high quality reading is obtained. The algorithms preferably include a 50 Hz/60 Hz notch filter for removal of any mains noise and the above-mentioned 3 lead detection algorithm.

For any data downloaded by the base station unit 30, the data is stored in a standard flat file format on the local hard disk, or in a separate location such as on a separate optical disk drive. In a preferred embodiment, all blocks of data stored are in a form that enables them to be exported from the physiological monitoring software in an HL7 compliant format. Each block of data stored may have a unique patient identifier, the sensor band and base station unit identification numbers, the date, and the time.

Remote monitoring unit 50 may also perform other types of processing on the received ECG data such as heart rate variability analysis, atrial fibrillation detection, ST episode detection, QT analysis, and other flagging events. Such processing techniques may be used to detect disease states such as cardiac failure, hypertension, angina, ischaemia/ coronary artery disease, peripheral vascular disease, acute and chronic respiratory insufficiency, history of recurrent arrhythmias, sub-acute patients, post-infarction patients, acute and recurrent febrile illnesses (including malaria, hepatitis, lymphoma, Hodgkin's disease, AIDS, tuberculosis) and the like, and such processing techniques are believed to be known to those skilled in the art.

II. Data Transmission Scheme

As noted above, the present invention wirelessly transmits data from the sensor band 10 a short distance to a signal transfer unit 20 and retransmits the data wirelessly from the signal transfer unit 20 to the base station unit 30. The data is then transmitted over conventional phone lines 40 or via a conventional wireless telecommunications link to a remote monitoring station 40. Each of these transmission links will be discussed in detail in this section.

Figure 6:
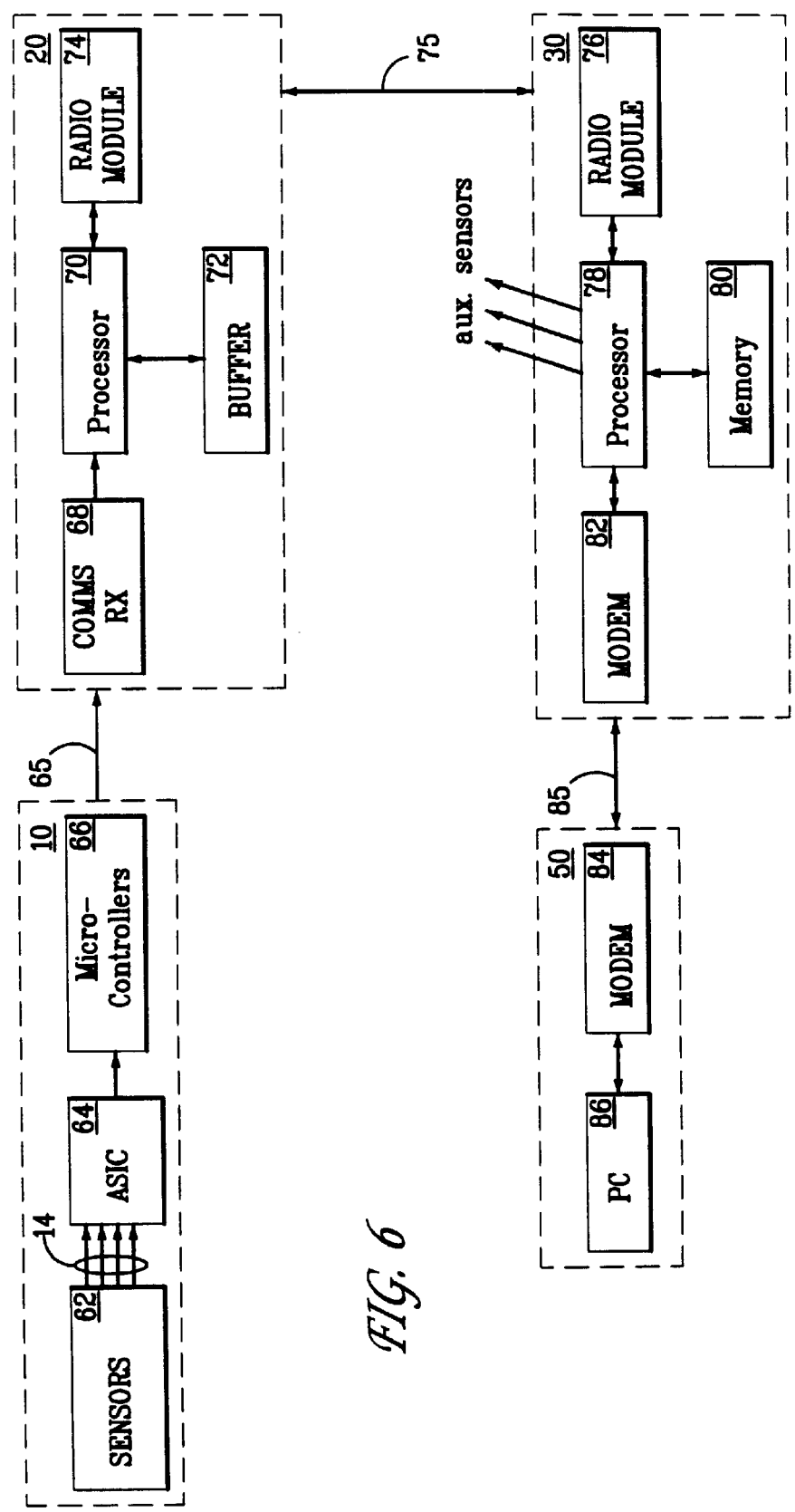
FIG. 6 illustrates a general block diagram of the system transmission electronics.

FIG. 6 illustrates a general block diagram of the system transmission electronics. As shown, the sensor band 10 includes a plurality of sensors (e.g., electrodes) 62 which provide analog vital signs data via traces 14 to an ASIC 64 for A/D conversion and signal conditioning. ASIC 64 also provides the necessary supply and drive signals to the electrodes 62. One of the micro-controllers 66 implements the communications modulation coding scheme described herein and passes the modulated signal to ASIC 64 and then to an antenna for wire-free communication to the signal transfer unit's signal conditioning unit. ASIC 64 in conjunction with one of the micro-controllers 66 continuously transmits the data including vital signs data over communications link 65 to signal transfer unit 20, where the vital signs data is received by communications receiver 68 and processed by processor 70. For example, processor 70 may condition the received signal, optionally compress the received data, and store the received data in FIFO memory buffer 72. As noted above, memory buffer 72 preferably has sufficient size so that the patient may leave the range of the base station unit 30 for at least an hour without losing any vital signs data. Radio transceiver 74 of signal transfer unit 20 then transmits the data over communications link 75 to a corresponding radio transceiver 76 of the base station unit 30. As noted above, base station unit 30 includes a processor 78 which preferably implements software algorithms that calculate heart rate and respiration rate from the ECG and respiration signals, respectively. The received vital signs data is accumulated in memory 80 where it is stored until a remote monitoring station download is initiated, at which time the stored data is uploaded over communications link 85 (e.g. including telephone lines 40) using modem 82 of the base station unit 30 and modem 84 of the remote monitoring station 50. For example, the vital signs data may be uploaded once per day in the early morning hours to minimize interference with normal telephone usage, uploaded several times per day, or once per week. Remote monitoring station 50 then processes and displays the received vital signs data using a conventional personal computer 86, as will be described in more detail in the following section.

The remainder of this section will address the formatting of the communications links 65, 75, and 85 in the preferred embodiment. The communications links described herein were chosen for satisfactory performance in the home environment. Those skilled in the art will appreciate that other communications modalities may be preferred in different environments under different circumstances. For example, radio transceiver 74 of the signal transfer unit 20 may include a conventional cell phone which communicates directly with the remote monitoring station 50 so as to eliminate the base station unit 30; similarly, communications link 85 could be a cell phone link. Moreover, the signal transfer unit 20 could be eliminated by providing cell phone capability in the sensor band 10 or by providing expanded broadcast capability to extend the range to the base station unit 30; however, such devices will inevitably be more expensive to manufacture than the device described in connection with the preferred embodiment of the invention.

A. Sensor Band—Signal Transfer Unit Link

In the preferred embodiment, communications link 65 uses digital phase-shift keyed modulation to transmit the vital signs data via an inductive link. For the purposes of this discussion it is assumed that a band from 50 kHz to 150 kHz is available for inductive transmissions from the sensor band 10 to the signal transfer unit 20. If only a narrower frequency band is available, then one or more channels will be lost from the transmission scheme described below.

The sensor band 10 and the signal transfer unit 20 each contain a coil, and inductive coupling between the two coils is used to transmit the vital signs data. In a preferred embodiment, the signal transfer unit 20 contains three orthogonal coils with reception selected on the coil with the most usable signal at any point in time. The preferred embodiment also defines sixteen frequency-division multiplex channels with carriers at 6 kHz intervals from 54 kHz to 144 kHz inclusive. A one-bit digital version of the modulated signal is generated directly in software by one of the micro-controllers 66. The steps entailed in producing the code for the one of the micro-controllers 66 are described below.

In the preferred embodiment, the modulation scheme employed for transmission from in the sensor band 10 is digital QPSK (quadrature phase-shift keying). In this scheme, binary data is transmitted as bit pairs, known as symbols, at a regular rate, called the symbol rate. The effective bit rate is thus twice the symbol rate. Each symbol corresponds to a different phase offset (0, 90, 180 or 270 degrees) of the transmitted signal relative to a fixed carrier. These phase offsets can be represented as the points 1, i, −1 and −i in the complex plane. The nature of the transitions between adjacent symbols determines the envelope of the spectrum of the transmitted signal. In practice, to constrain the bandwidth of the signal, a raised cosine function is used to interpolate between the signals representing adjacent symbols. Unlike more sophisticated interpolation functions, the raised cosine function has the characteristic that the influence on the transmitted signal of one symbol does not extend further than the two symbols either side of it. Transitions between the symbols can be thought of as the motion of a point between the symbol points, and thus as a complex function of time. The transmitted signal is then the real part of this function multiplied by a complex exponential representing the carrier.

In the preferred embodiment, symbols are transmitted at a 2 kHz rate.

Since each symbol represents two bits, this corresponds to a bit rate of 4 kbps. In the preferred embodiment, the carrier signal is phase-locked to the symbol transitions. For example, with a carrier frequency of 102 kHz, there are exactly 51 cycles (102 kHz/2 kHz) of carrier in each symbol time. Thus, the value at any given time of the complex exponential representing the carrier only depends on the time since the last symbol transition. This, coupled with the characteristic of the raised cosine interpolation function stated above, means that the transmitted signal is built up from only a limited number of template waveforms: one for each possible transition between symbols. Since there are four symbols, there are sixteen possible transitions and thus sixteen possible template waveforms (including those where the symbol remains constant).

The several stages involved in compiling the communications code will now be described. Reference is made to implementation on a PIC16F84 micro-controller running at an instruction rate of 1 MHZ, but the principles described herein are generally applicable to other micro-controllers which may be used in the communications scheme described herein. An example carrier frequency of 102 kHz is assumed for illustrative purposes; the same principles will apply to other frequencies.

The modulated output is generated on one bit of an output port, and symbol data is received on a pair of input bits. A trigger pulse is generated on a further output port bit to request each new symbol.

Sixteen template waveforms are generated at compile time that are sampled at the instruction rate of one of the micro-controllers 66, i.e. 1 MHZ. These template waveforms are then converted to digital streams, either by simple thresholding or by a more sophisticated 'bitstream' method. Each of the sixteen waveforms contains 500 (1 MHz/2 kHz) samples, for 8000 samples in all. Where simple thresholding has been used, each waveform consists of about 51 (102 kHz/2 kHz) pulses, or 102 state changes. If the phase angle increases through the waveform, there may be more than 102 state changes; if the phase angle decreases, there may be fewer.

The template waveforms are referenced by the symbol represented at their start (0,1,2 or 3) and by the symbol represented at their end (again 0,1,2 or 3). For example, waveform [0,1] starts with a phase angle of 0 relative to the implied carrier, and ends with a phase angle of 90 degrees relative to it. For a waveform [a,b] to join smoothly to a waveform [c,d], it is necessary that b=c. A symbol sequence . . . u,v,w,x . . . therefore includes the waveform sequence . . . [u,v][v,w][w,x] . . .

With a slight modification to the interpolation function, waveform templates [u,0], [u,1], [u,2] and [u,3] can be made all to begin with the same sequence of samples and, in particular, can be made all to have their first state change at the same point. All samples leading up to this first state change are removed from the waveforms and added to the end of each waveform template [0,u], [1,u], [2,u] and [3,u]. This is carried out for each value of u from 0 to 3 as illustrated in FIG. 7A. Each template waveform now begins with a state change and ends with a period free of state changes. This idle period will later be used to link together the various templates. As a result, the templates are no longer all necessarily the same length.

The sampled waveforms are now converted into micro-controller instructions. Zero-to-one waveform state changes are converted into instructions which set an output port bit; one-to-zero waveform state changes are converted into instructions which clear that bit. Idle periods between changes are converted into a sequence of no-operation instructions such that the correct time delays between changes are introduced. This procedure is illustrated in FIG. 7B. As shown, the end of each template now consists of a number of no-operation instructions.

A small number of extra instructions is required to read the state of the input port bits corresponding to the next symbol to be transmitted, select the appropriate waveform template, and produce a symbol trigger pulse. The instructions at the start of template [u,0] (for each u) are searched for suitable points where these extra instructions can replace no-operation instructions. If symbol 1 is required, these new instructions cause a jump into the code for template [u,1] at the correct point to ensure continuity of the waveform; similarly, if symbol 2 is required, a jump is caused into template [u,2]; and if symbol 3 is required, a jump is caused into template [u,3]. Code in templates [u,1], [u,2] and [u,3] before the destinations of these new jump instructions will never be executed and is deleted. Finally, as illustrated in FIG. 7B, some of the last no-operation instructions in template [u,v] (for each u and v) which were created in the step of creating an idle period at the end of each template are replaced by a jump instruction to the start of template v, again in such a way as to ensure continuity of the waveform.

The code at this point is typically 8000 instructions long, too long to fit in a low-cost micro-controller. A number of optimization algorithms is therefore applied to reduce the code size. Unlike conventional optimization algorithms, it is essential that these preserve exactly the timing of instructions executed.

The code is searched for the longest sequence of instructions that occur more than once using an algorithm which iteratively increases the length of candidate sequences, rejecting them as they become unique. Only those sequences which could be converted to a subroutine are considered;

these need to have enough no-operation instructions at either end to cover the subroutine call and return overheads of the micro-controller. When the longest sequence is found, it is converted to a subroutine with the appropriate number of no-operation instructions deleted from either end to cover the time required for the call and return; each occurrence of the sequence is then replaced with a subroutine call instruction. This procedure is then repeated until no further suitable duplicated sequences are found. The code size will now have been reduced to perhaps 2000 instructions.

The pool of newly-created subroutines is now searched to identify instances where the whole of a subroutine A (consisting of n instructions) is identical to the last n instructions of another subroutine B. All calls to subroutine A are replaced with calls to the point n instructions from the end of subroutine B. Subroutine A is then deleted.

A number of peephole optimizations is also performed which reduce code size while preserving timing in accordance with the invention. For example, on the PIC16F84, two consecutive no-operation instructions can be replaced with a jump to the following location, saving one instruction.

A small number of instructions is added to the beginning of the optimized code to initialize the micro-controller. The code is now complete and ready to be programmed into the appropriate one of the micro-controllers 66. The above procedure need only be performed once for each desired carrier frequency.

Figure 8:
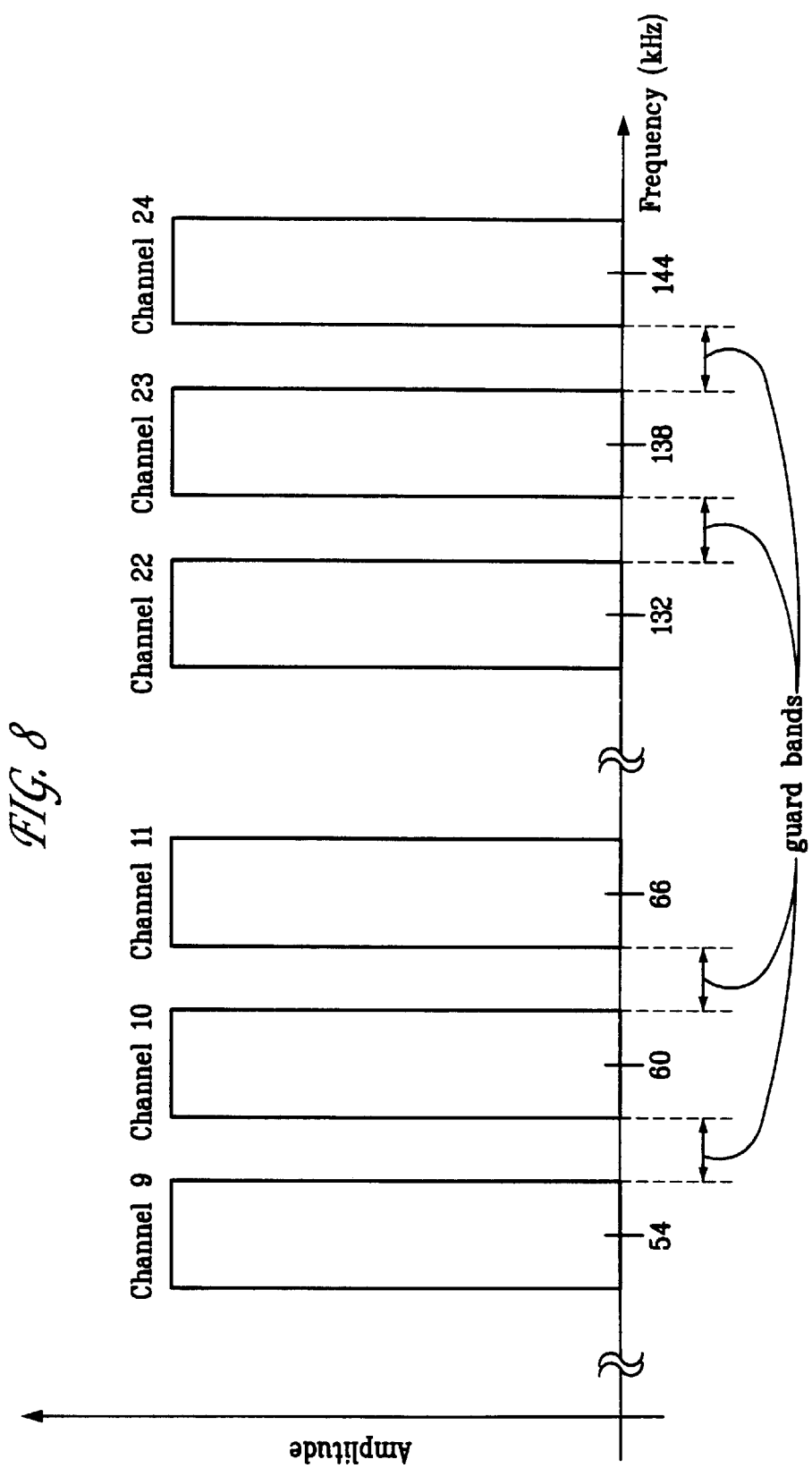
FIG. 8 illustrates the sixteen channels spaced at 6 kHz intervals used in the communications link between the sensor band and the signal transfer unit.

As noted above, the communications link 65 is divided into sixteen channels spaced at 6 kHz intervals. For simplicity, the center frequencies of the channels are at multiples of 6 kHz. The lowest-frequency channel is therefore centered at 54 kHz and the highest at 144 kHz as illustrated in FIG. 8. Channels are referred to by number, where the number is the center frequency divided by 6 kHz. Thus, the available channels are numbered 9 to 24 inclusive. Each channel carries a QPSK signal with a symbol rate of 2 kHz and a data rate of 4 kbps. The channel thus occupies a band 2 kHz either side of its center frequency with guard bands 2 kHz wide separating adjacent channels as shown in FIG. 8.

Those skilled in the art will appreciate that, given the digital nature of the coil driving circuit of the sensor band 10, the majority of the out-of-band power for any channel is likely to be at its third harmonic. Since the third harmonic of channel 9 (52 kHz–56 kHz) lies in the range 156 kHz–168 kHz, it will not cause interference with channel 24, which occupies the range 142 kHz–146 kHz.

The majority of the different types of sensor bands 10 for use in accordance with the invention will have data rates which fit comfortably within a 4 kbps channel. For those sensor bands that require a higher data rate, it is possible to retain the phase-shift keying modulation scheme of the preferred embodiment but to represent more than two bits per symbol by the use of m-ary phase-shift keying. This would allow a higher data rate in the same channel width, although a higher signal-to noise ratio would be required for reliable communication. Alternatively, data compression techniques may be used to compress data into a single 4 kbps channel, or multiple channels could be used for a single sensor band.

The QPSK signal can be generated digitally and then passed through an oversampling modulator, implemented within the ASIC 64. This would directly generate a digital signal suitable for feeding to the coil driver. Alternatively, the transmitter of the sensor band 10 may require a small additional circuit, probably involving a phase-locked loop, to reduce out-of-band transmissions further than a practical oversampling modulator will allow.

At the communications receiver 68 of signal transfer unit 20, a number of QPSK channels can be simultaneously demodulated using a DSP device. A front-end comprising amplifiers, anti-aliasing filters and analog-to-digital converters is required. Such circuitry is described in detail in the aforementioned related U.S. patent application Ser. No. 09/292,159.

In accordance with the invention, the output of the DSP device comprises three signals:

1) a clock signal C;
2) a framing pulse F; and
3) a data signal D.

In the preferred embodiment, the data from the sensor band 10 consists of a continuous sequence of 160-bit packets, where the bit rate is nominally approximately 4 kHz and the packet rate is thus approximately 25 Hz. The framing pulse F indicates the position of bit 0 of each packet.

Figure 9:
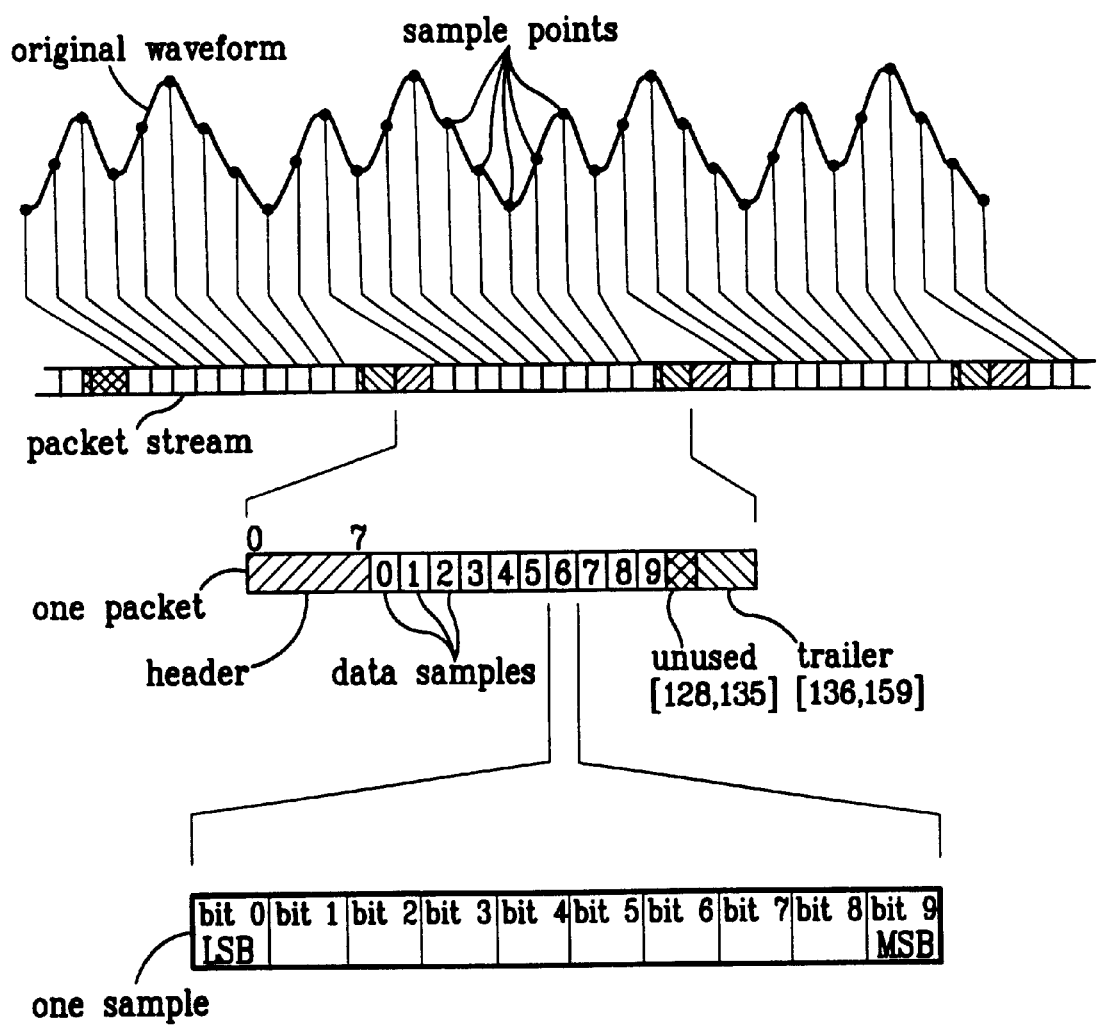
FIG. 9 illustrates the format of the data packets transmitted in the communications link between the sensor band and the signal transfer unit.

As illustrated in FIG. 9, of the 160 bits in each packet, 128 form the data payload. The remainder include a header including a field to indicate the format of the data and a sequence number that increments with each packet. A trailer includes an error-checking (CRC) field. The data capacity of the channel is therefore 25 Hz multiplied by 128 bits, or 3200 bps. This is sufficient capacity for the majority of the known sensor arrays to require only one channel each. If not, data compression or multiple channels may be used for each sensor band 10. Packets of data from several received channels can be multiplexed into a single output stream for the DSP.

As shown in FIG. 9, each packet of 160 bits is divided into a number of fields as follows:

1) bits 0–7; header, including packet type and sequence number. The packet type field defines the format of the data within the payload field. Each different sensor array could be assigned a different packet type. The three-bit sequence number increments modulo 8 with each packet and can be used to check the integrity of the data stream.
2) bits 8–135; data payload. The format of the data within the payload field is defined by the packet type.
3) bits 136–159; trailer. This field may include a CRC field which is an eight-bit CRC of the data in bits 0–135 of the packet. The CRC may be used to detect errors in marginal reception conditions or in the presence of interference.

Of course, certain sensor arrays may generate raw data at a rate higher than one channel can handle. The provision of suitable compression in the ASIC 64 or one of the micro-controllers 66 would allow one channel to be used, as well as reducing the bandwidth requirement of the transmissions over the communications link 65. In addition, buffering requirements in the signal transfer unit 20 would be reduced, and communications requirements between the signal transfer unit 20 and base station unit 30 would be simplified. However, if such compression cannot be provided due to cost and the like, more than one channel would need to be used for each sensor array 10.

B. Signal Transfer Unit—Base Station Unit Link

As noted above, the signal transfer unit 20 has a memory buffer 72 which enables at least three modes of operation for the signal transfer unit 20. In normal operation, the signal transfer unit 20 communicates with the base station unit 30 with no data stored in the memory buffer 72. The memory buffer 72 is preferably disabled in order to minimize the supply current. The data is transmitted via the communications link 75 using the protocol to be described below. The user interface (FIG. 3) has normal operational information displayed. The signal transfer unit 20 may also operate without a communications link to the base station unit 30. In this state, the vital signs data arrives at the signal transfer unit 20 as in the normal state. However, the data is redirected from the communications receiver 68 to a buffer of processor 70. When the processor's buffer fills up (this only allows 4 packets worth of data and is held on-chip in the RAM of processor 70) the data is directed to the much larger memory buffer 72, which may be, e.g., a DRAM, a flash memory, or other comparable memory device. If the memory buffer 72 becomes 90% full, an alarm condition may be set. On the other hand, the signal transfer unit 20 may operate with a communications link 75 but still having data stored in the processor's buffer and/or memory buffer 72 on a "first-in, first-out" (FIFO) basis. In this state, the buffered data is sent to the base station unit 30 as quickly as possible, with new incoming data being directed to the memory buffer 72. In any of these states, the CRC status bits of the incoming data frame will be examined, and if these show that the data is valid, the data is extracted and, depending on the state of the signal transfer unit 20, this information will either be directly built into a packet for transmission to the base station unit 30 (or placed in a buffer ready for transmission) or will be sent to the next available area of the memory buffer 72. If the CRC fails, the data packet is discarded.

In the preferred embodiment, the radio-transciever 74 of the signal transfer unit 20 is a transmitter/receiver based on the RF2905 transceiver chip with the following interface lines to baseband:

1) data in (data received from the base station unit 30);
2) data out (data transmitted to the base station unit 30);
3) T/R—transmit/receive switch; and
4) power up flag (to wake the transceiver from sleep mode).

The other interface connections to the RF2905 chip can be derived from these interfaces using a small amount of logic circuitry so as to reduce the number of I/O ports required on the processing device.

In the preferred embodiment, communications link 75 runs at a 40 kbps baud rate. A packet typically comprises a preamble, a synchronization codeword, various packet definition codes, a packet ID, data, and a CRC error detection code. In a preferred embodiment, the CRC code is 16 bits wide and the data content within a packet is 32 bits, resulting in a CRC algorithm performing over a 48-bit packet. The CRC is performed in baseband in the signal transfer unit 20 for both the transmitted and received data. The CRC algorithm is performed in real-time if possible, utilizing 32-bit registers and various rotate and shift instructions in the instruction set of processor 70. If the CRC cannot be performed in real-time, the data will be buffered and the CRC will be performed as soon as the current reception is complete. Due to the base station channel being predominantly for data traffic to the base station unit 30, this incoming data procedure should have little activity; however, this will not be the case during periods of poor reception when data will need to be re-transmitted and "NAK" codes sent regularly from the base station unit 30.

Data received from the transceiver of the radio transceiver 74 is asynchronous; therefore, clock extraction is a function that must be performed by the signal transfer unit 20 in baseband. This involves over-sampling of the synchronization codeword (a 101010 . . . pattern) and performing frame alignment.

The communications protocol between the signal transfer unit 20 and the base station unit 30 has been designed to address the following requirements:

1) The system must be compatible with half duplex operation for implementation within a single radio frequency allocation;
2) Battery life at the signal transfer unit 20 is a critical parameter in the overall system performance and the power consumption at the base station unit 30 is of lesser consideration. Therefore, the protocol must favor low consumption at the signal transfer unit 20;
3) High efficiency in the data flow from the signal transfer unit 20 to the base station unit 30 is required to maximize the channel information capacity of the radio link;
4) A simple protocol implementation is desirable to minimize processing power at the signal transfer unit 20 and hence reduce power consumption; and
5) A high degree of data integrity is required with erroneous data being harmful to the applications supported by the system. Therefore, the system must 'fail safe' with the preference being to supply no data rather than erroneous data.

The communications protocol between the signal transfer unit 20 and the base station unit 30 has been designed to transport data over a physical channel implemented as a radio link. The behavior of radio propagation channels is well documented and of relevance to the protocol design is its tendency to exhibit burst error characteristics rather than random bit errors. This is due to fading effects originating from mechanisms such as multi-path, shadowing, and antenna orientation. Therefore, a data packet scheme has been adopted with CRC to provide error detection and an ARQ scheme to retransmit erroneous data packets. No provision for bit error correction has been implemented and data scrambling has been included to minimize the DC component in the data stream. Wherever possible, the protocol has been designed to be unrestrictive to the data format being transferred over the communications link 75 while maximizing efficiency, which assumes prior knowledge of the format of the measurement data.

Since the protocol favors low power consumption at the signal transfer unit 20, a communications dialog is always initiated by the signal transfer unit 20 and never the base station unit 30. This allows the signal transfer unit 20 to power down when in idle mode and removes the requirement for high specification timing components.

In the preferred embodiment, the communications protocol is asynchronous. Initial dialogue synchronization is established with a preamble sequence and provision for subsequent timing alignment is provided by synchronization sequences preceding all data packets.

Three basic functional mechanisms are provided in the signal transfer unit/base station unit protocol:

1) Registration;
2) Idle/re-registration; and
3) Information flow.

These mechanisms will now be described in detail.

Registration Mechanism

Figure 10A:
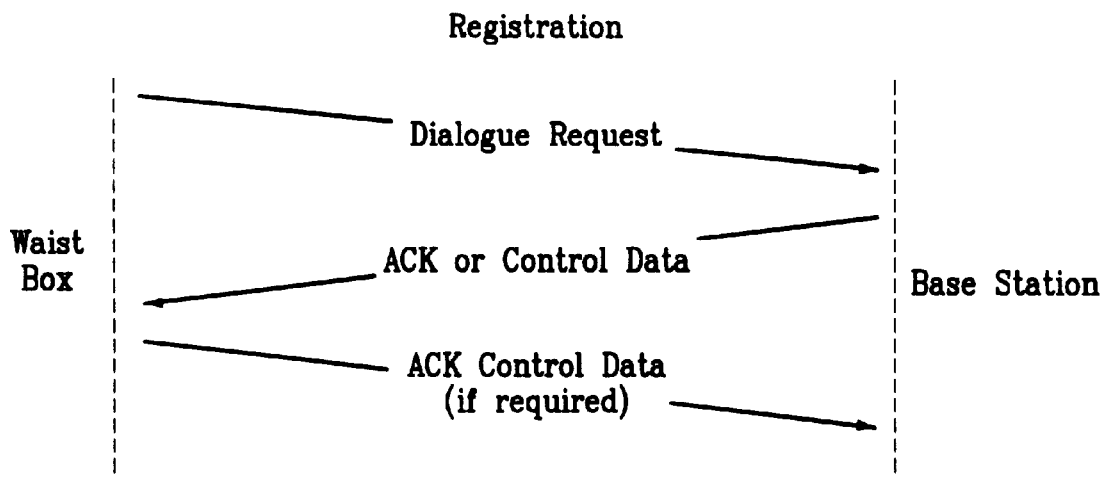
FIG. 10A illustrates schematically the registration mechanism by which the signal transfer unit and the base station unit acknowledge their mutual presence and confirm the performance of the radio link.

The purpose of the registration mechanism is to provide a means by which the signal transfer unit 20 and the base station unit 30 acknowledge their mutual presence and confirm the performance of the radio link 75. It provides an opportunity for the base station unit 30 to send initializing control parameters to the signal transfer unit 20 if required. FIG. 10A represents this mechanism. As illustrated in FIG.

10A, the dialog is initiated with a dialog registration request from the signal transfer unit 20 which must be transmitted within $t_{POWER\_UP}$ seconds of the signal transfer unit 20 being powered up. The base station unit 30 responds to the registration request with an acknowledgment (ACK) packet to confirm its correct receipt or a data packet containing control information which implicitly provides the acknowledgment. In the latter case, the signal transfer unit 20 must acknowledge the safe receipt of the control information. If the control data exceeds a single packet length, multiple packets may be used to fragment the control information, with an acknowledgment being required from the signal transfer unit 20 for each packet. This is conducted in the same manner as the data flow mechanism described below with respect to FIG. 10B. If no control data is transmitted from the base station unit 30 and a simple acknowledgment packet is sent, the signal transfer unit 20 will not provide further acknowledgment. It is recommended that the base station unit 30 allocate a unique logical unit number to the signal transfer unit 20 during the registration dialog using the appropriate control code such that control data is always sent in place of the acknowledgment package.

If the signal transfer unit 20 fails to achieve registration, the signal transfer unit 20 will wait for a minimum time of $t_{MIN\_REG\_WAIT}$ and a maximum time of $t_{MAX\_REG\_WAIT}$ before making another attempt at registration with a dialog request. It is recommended that a random element be included in the wait time in order to facilitate random access schemes in the case of multiple signal transfer units 20 transmitting to a single base station unit 30 in alternative embodiments.

Idle Mechanism

The purpose of the idle mechanism is to maintain registration of the signal transfer unit 20 and to provide the opportunity for the base station unit 30 to reconfigure control parameters within the signal transfer unit 20 if required. The format of the dialog is identical to the registration mechanism with the difference lying in the format of the dialog request packet. In order to maintain registration, the maximum allowable time between idle dialog (or registration dialog in the first instance) will be $t_{MAX\_IDLE}$ and registration will become invalid if no dialog is conducted after $t_{LOSE\_REG}$ of the previous dialog. Thus, $t_{MAX\_IDLE}$ defines the maximum time permissible before control data can be sent to the signal transfer unit 20 and $t_{LOSE\_REG}$ defines the time after which registration becomes invalid.

Data Flow Mechanism

Figure 10B:
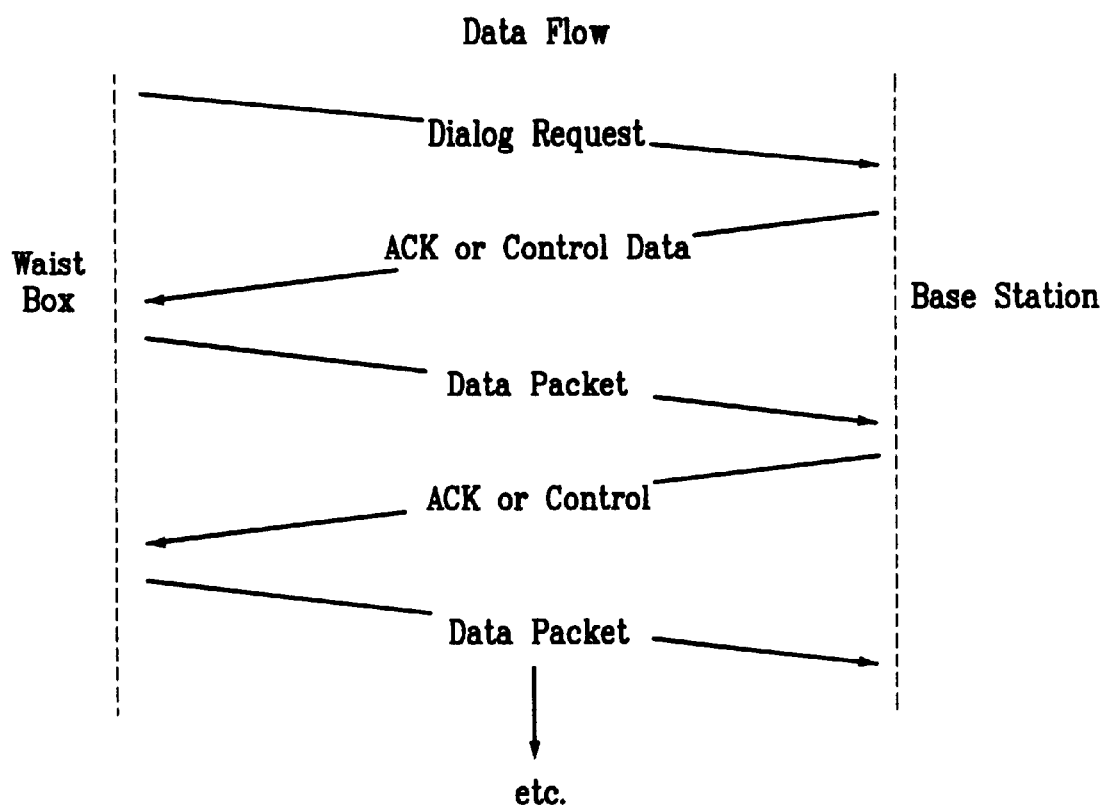
FIG. 10B illustrates the data flow mechanism by which measurement data is transferred from the signal transfer unit to the base station unit to provide the opportunity for the base station unit to reconfigure control parameters within the signal transfer unit if required.

The purpose of the data flow mechanism is to transfer measurement data from the signal transfer unit 20 to the base station unit 30 and to provide the opportunity for the base station unit 30 to reconfigure control parameters within the signal transfer unit 20 if required. FIG. 10B illustrates the data flow mechanism. As illustrated in FIG. 10B, the data flow mechanism is similar in its implementation to the registration and idle mechanisms except the dialog request packet must notify the base station unit 30 that the signal transfer unit 20 has valid data waiting. As before, an acknowledgment packet may be replaced by a data packet with implicit acknowledgment and, similarly, the data packet on the reverse link may implicitly acknowledge safe receipt of the control information. The data packets contain control information that informs the base station unit 30 if further data packets are to be transmitted in the dialog.

ARQ Scheme

The purpose of the ARQ scheme is to provide the means by which erroneous data packets are retransmitted based on the use of "not-acknowledged" (NAK) packets to request retransmission. In order to conserve power at the signal transfer unit 20, the number of times a packet may be retransmitted is limited, and if either the base station unit 30 or signal transfer unit 20 receives two consecutive erroneous packets, the data link will be considered to have failed, and a minimum time of $t_{MIN\_FAIL\_WAIT}$ will be allowed to elapse before the signal transfer unit 20 attempts to re-establish the link with a dialog request. The scheme is independent of packet type such that an acknowledgment package is treated in the same manner as a data packet.

Three cases are therefore identified.

Case 1

Figure 10C:
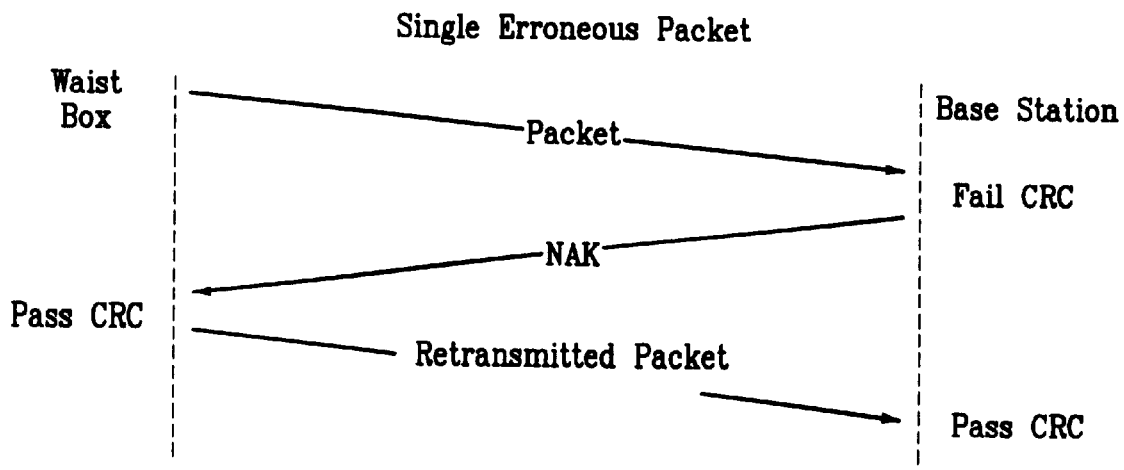
FIGS. 10C and 10D illustrate the ARQ behavior when a single erroneous packet is detected and no further errors occur on the link thereafter for transmission from the signal transfer unit to the base station (FIG. 10C) and from the base station to the signal transfer unit (FIG. 10D).
Figure 10D:
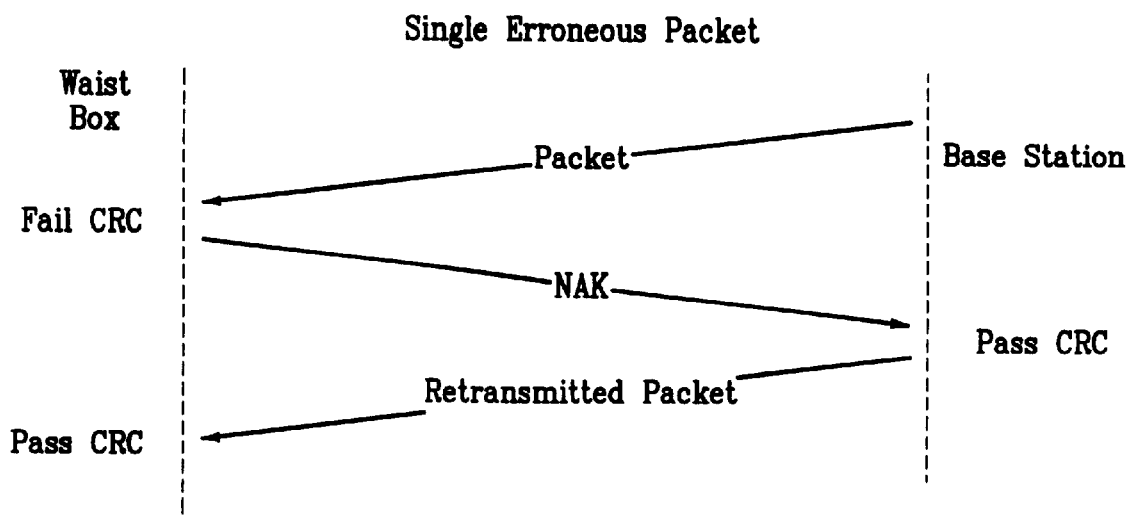

This case defines the ARQ behavior when a single erroneous packet is detected and no further errors occur on the communications link 75 thereafter. FIG. 10C defines the mechanism. As illustrated in FIG. 10C, the signal transfer unit 20 sends a data packet which is incorrectly received at the base station unit 30, the base station unit 30 sends a NAK package which contains a data field pointing to the first detected erroneous packet, and the signal transfer unit 20 retransmits the data packet. As illustrated in FIG. 10D, an identical procedure is adopted if the signal transfer unit 20 fails to receive a packet from the base station unit 30.

Case 2

Figure 10E:
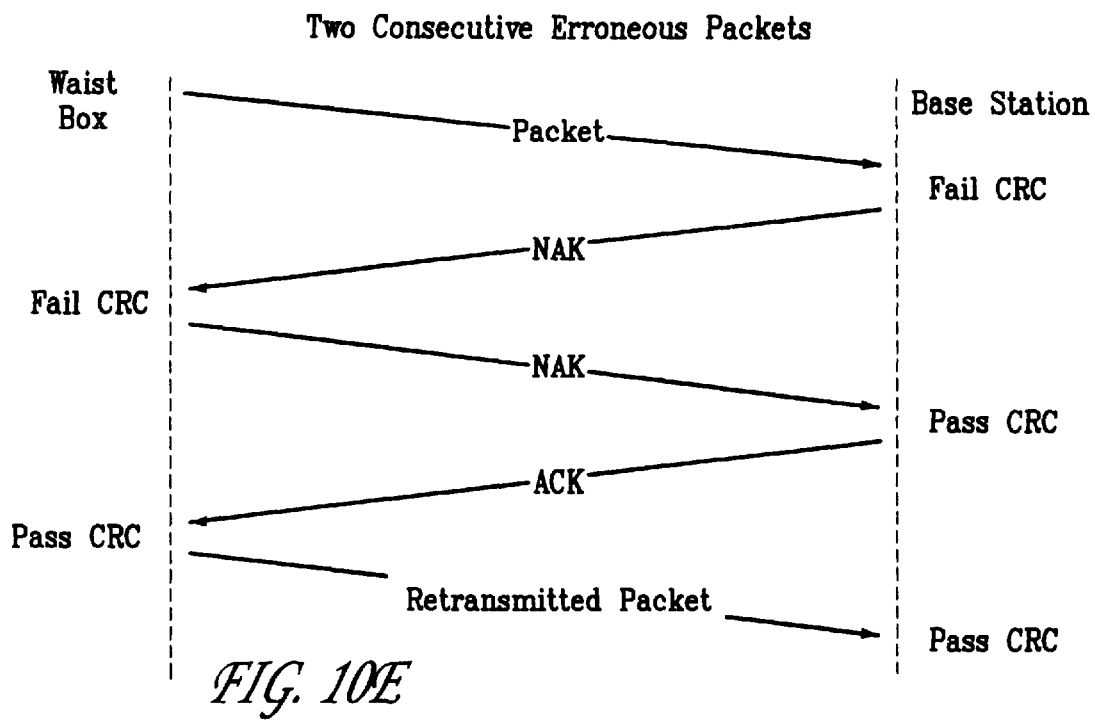
FIGS. 10E and 10F illustrate the ARQ behavior when two erroneous packets are detected consecutively and no further errors occur on the link thereafter for transmission from the signal transfer unit to the base station (FIG. 10B) and from the base station to the signal transfer unit (FIG. 10F).
Figure 10F:
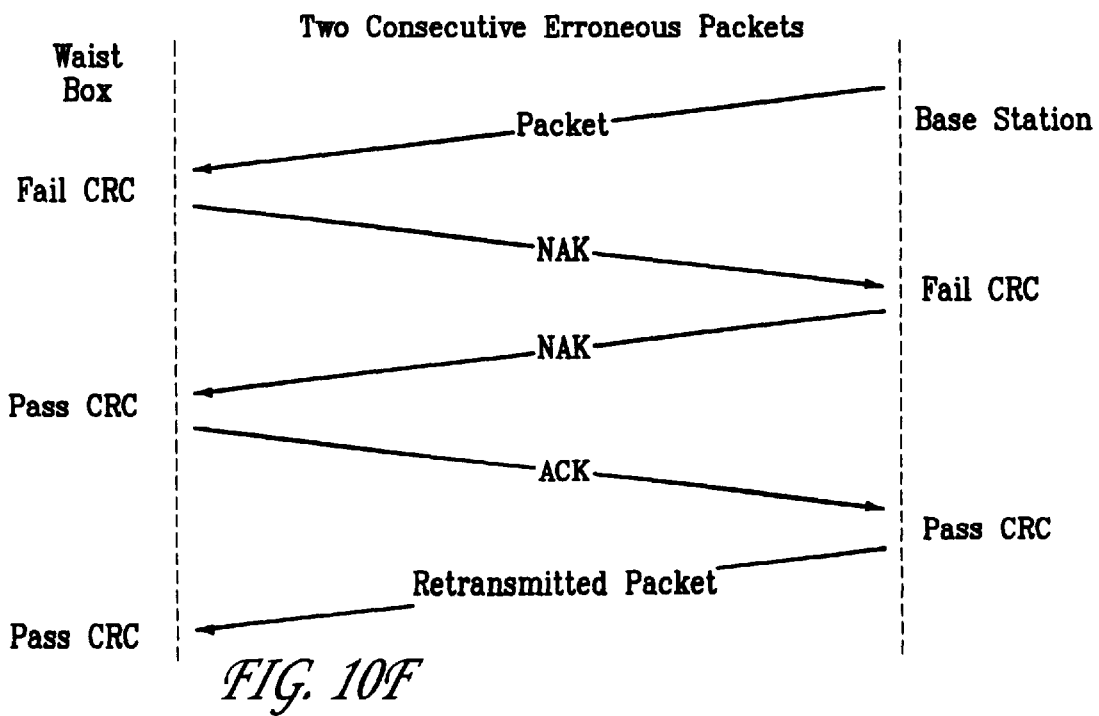

This case defines the ARQ behavior when two erroneous packets are detected consecutively and no further errors occur on the communications link 75 thereafter. FIG. 10E defines the mechanism. As illustrated in FIG. 10E, the signal transfer unit 20 sends a data packet which is incorrectly received at the base station unit 30, and the base station unit 30 sends a NAK packet which is incorrectly received by the signal transfer unit 20. The signal transfer unit 20 then transmits a NAK which is correctly received at the base station unit 30 which then retransmits the first NAK packet containing a data field pointing to the first detected erroneous packet which is subsequently retransmitted by the signal transfer unit 20. As illustrated in FIG. 10F, an identical procedure is adopted if the signal transfer unit 20 fails to receive a packet from the base station unit 30.

Case 3

Figure 10G:
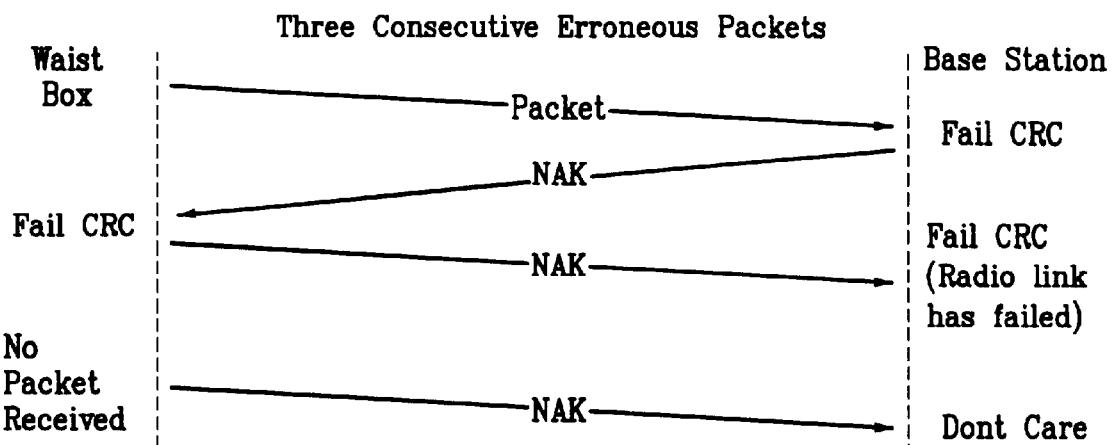
FIGS. 10G and 10H illustrate the ARQ behavior when three erroneous packets are detected consecutively and no further errors occur on the link thereafter for transmission from the signal transfer unit to the base station (FIG. 10G) and from the base station to the signal transfer unit (FIG. 10H).
Figure 10H:
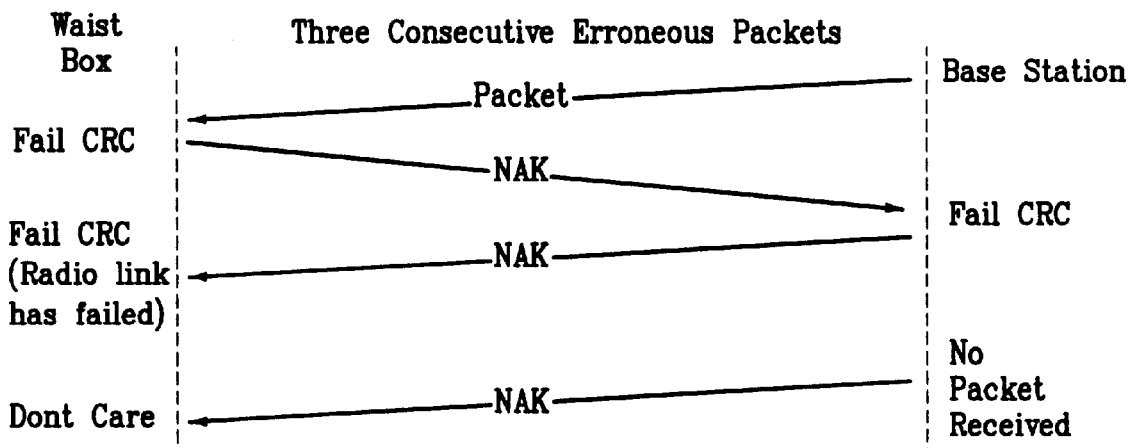
Figure 10I:
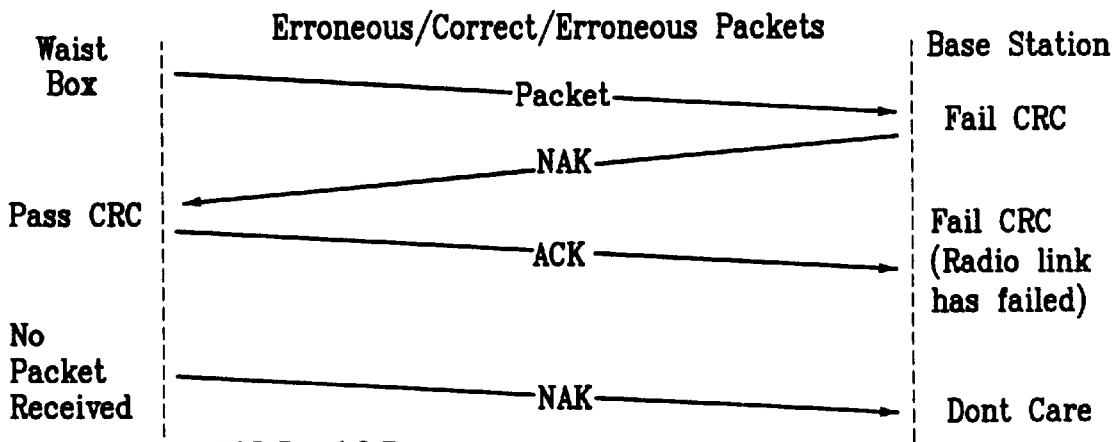
FIG. 10I illustrates the ARQ behavior when a correctly received packet lies between two erroneous packets as the receiving unit detects two consecutive erroneous data packets and considers the radio link to have failed.

This case defines the ARQ behavior when three erroneous packets are detected consecutively. FIG. 10G shows the mechanism. As illustrated in FIG. 10G, the base station unit 30 receives two consecutive erroneous packets and hence recognizes that the radio link has failed. No further reply is sent to the signal transfer unit 20 which, by implication, will inform the signal transfer unit 20 that the link has failed. The base station unit 30 then returns to receive mode and awaits re-establishment of the communications link 75 by a dialog request from the signal transfer unit 20. Similarly, if the first erroneous packet is received by the signal transfer unit 20, an identical mechanism is adopted as shown in FIG. 10H. This case also defines the situation where a correctly received packet lies between two erroneous packets as the receiving unit detects two consecutive erroneous data packets and considers the radio link to have failed. FIG. 10 illustrates the dialog in this case.

Packet Formats

The format of the data packets required to implement the functional mechanisms described above will now be described. Three primary types of packet are defined as follows:

1) Dialog Request Packet;
2) Acknowledgment Packet; and
3) Data Packet.

Subsets of each primary type are defined to implement the detailed functionality.

Dialog Request Packet

A dialog request packet initiates a dialog between the signal transfer unit 20 and the base station unit 30 and can only be sent by the signal transfer unit 20. Three types of dialog exist to implement registration, idle mode and data transfer initiation. All dialog request packets are of fixed length and preceded by a preamble with a single CRC bit sequence appended to the end of the packet. In each case, the CRC is applied to the information content of the packet and excludes the preamble and synchronization codeword. Generally, each dialog request packet contains a preamble that allows an analog data slicing hardware threshold in the radio circuitry to settle to an appropriate value for optimum data reception, a synchronization codeword which allows the receiver to synchronize its bit sampling mechanism, a registration identification codeword that identifies the transmitted data packet as a registration data packet, an optional serial ID assigned to the signal transfer unit 20 at manufacture and/or logical unit ID assigned to the signal transfer unit 20 by the base station unit 30 to provide limited addressing functionality in the case of a plurality of signal transfer units 20 transmitting to a single base station unit 30, a modulo counter number (packet ID), and CRC bits.

Acknowledgment Packet

An acknowledgment packet is used to inform the sender of the success of a transmitted packet. Two types of acknowledgment packet are defined for success and failure. All acknowledgment packets are of fixed length and have a CRC bit sequence appended to the packet. In each case the CRC applies only to the data content of the packet and excludes the synchronization codeword. Generally, each acknowledgment packet contains a preamble, a synchronization codeword, an ACK or NACK identification codeword, an optional serial and/or logical unit ID of the signal transfer unit 20, a packet ID, a packet success ID or retransmit reference ID, and CRC bits.

Data Packet

Data packets are used to transfer sensor data from the signal transfer unit 20 to the base station unit 30 and control information from the base station unit 30 to the signal transfer unit 20. In order to minimize the processing requirements of the signal transfer unit 20 and transmit-receive switching time, the information contained within the packet may be divided into an integer number of data codewords with CRC individually applied to each word. The synchronization codeword is excluded from this process. Two types of data packet are defined to implement rapid data transfer and control data transfer. For each type of data packet, two identification codewords are applicable which indicate whether another data packet is to follow.

The CRC is embedded in the data packet according to the codeword structure. Each codeword contains $N_{BITS\_PER\_CODEWORD}$ and a maximum of $N_{MAX\_CODEWORDS\_PER\_PACKET}$ are allowed in a single data packet. It is permissible to fragment data between successive data packets and no restriction is applied regarding the point of fragmentation.

The rapid data packet is used to transfer measurement data from a single sensor device as efficiently as possible and contains minimal control content. This type of data packet is preferably used in instances where maximizing the capacity of the communications channel is paramount. This data packet preferably includes an indication of the Signal Transfer Unit Logical Unit and the Data Source ID. The CRC will be embedded in the data packet according to the codeword structure.

The control data packet is used to transfer control data to configure parameters within the signal transfer unit 20. It is identical in format to the rapid data packet except that the free format sample data field contains a number of control sequences.

In a preferred embodiment, data scrambling is applied to all bits transmitted over communications link 75, with the exception of synchronization codewords and preambles. Data scrambling is applied to minimize the DC content of the data within a particular packet and is achieved by multiplying the bitstream with a fixed pseudo noise (PN) sequence having a length equal to the length of a data codeword (including the CRC) such that the scrambling is applied codeword by codeword for a data packet and a partial sequence used for all other types of packet.

In transmitting data pursuant to the above-described transmission protocol, the communications link 75 is required to transport a maximum information rate of 15 kbits/sec over a range of 60 meters. In addition, the communications link 75 must support the data overheads associated with the protocol and provide sufficient capacity for the system to transmit previously stored measurements at a higher data rate to catch up with the real time function in the event that the signal transfer unit 20 should be taken out of range for a period of time. Assuming a minimum protocol efficiency of 63%, a minimum data rate of 23.8 kbits/sec is required to achieve the required information rate assuming a perfectly reliable link.

Taking into account restrictions imposed by baseband processing, a data rate of 40 kbits/sec has been adopted in a preferred embodiment to provide an information capacity of 25.2 kbits/sec which translates to a duty cycle of 59.5% under good operating conditions or a catch-up rate of 0.68 hours/hour when the full information capacity is required. Since the spectral allocations for unlicensed radio transmission are at 433 MHZ and 915 MHZ in Europe and the USA, respectively, with a small number of exceptions where bandwidth is specifically allocated for medical telemetry applications, these frequencies are chosen for transmission via communications link 75 in the preferred embodiment. In general, the allocations provide more than 100 kHz of bandwidth which will not be restrictive to the system given the 40 kbits/s data rate.

C. Base Station Unit—Remote Monitoring Station Link

Communications link 85 is used to transfer the acquired patient vital signs data from the base station unit 30 to the remote monitoring station 50 and to transfer configuration information from the remote monitoring station 50 to the base station unit 30. In a preferred embodiment, the base station unit 30 and remote monitoring station 50 communicate in a stream-based protocol implemented using TCI/IP sockets, where each data packet has a message start byte, bytes indicating total message length, a message command, and message contents. The data packets generally contain a data timestamp and ECG, respiration, temperature, motion, and bend data; however, data packets from the base station unit 30 may also contain weight, blood pressure, and spirometer readings from the auxiliary sensors. Other packet types may include heart rate, respiration rate, temperature and/or event data.

Generally, before TCP/IP communication between the base station unit 30 and the remote monitoring station 50 can be established, a network connection must first be established between the two systems. The remote monitoring station 50 initiates connection to the base station unit 30, and once the connection has been accepted, both ends of the communications link 85 will listen for commands. The protocol may be terminated by either end of the communications link 85 disconnecting its socket. Each command is unidirectional, and acknowledgment of any command is necessary.

A command set of the protocol for communications between the base station unit 30 and the remote monitoring station 50 in the preferred embodiment of the invention will now be described. The following partial list of commands are used to implement the communications protocol over the communications link 85.

An AddDataSource command from the remote monitoring station 50 instructs the base station unit 30 to begin acquiring data from a data source (sensor band 10) specified in a data source ID within the command and to use a particular type of stream. Usually, this command identifies the wireless channel to use.

A RemoveDataSource command from the remote monitoring station 50 instructs the base station unit 30 to stop acquiring data from the specified data source ID.

A SetConfig command from the remote monitoring station 50 sends any required configuration data to the base station unit 30 and may contain flags instructing the base station unit 30 to flush the databases of the base station unit 30.

An AckConfig command from the base station unit 30 acknowledges to the remote monitoring station 50 successful receipt of the SetConfig message.

A DataRequest command from the remote monitoring station 50 requests that the base station unit 30 sends a specified time range of raw or real-time data to the remote monitoring station 50. The data record type field within the command specifies the format that the remote monitoring station 50 will expect to be returned. In some cases, the same raw data may be requested in multiple formats. Only one request for data may be active at any one time.

A DataRequestAbort command message from the remote monitoring station 50 causes all outstanding data requests to be aborted, including Event and Alarm data requests. This command should be sent before the remote monitoring station 50 terminates the communications link 85.

A ReturnComplete command is sent by the base station unit 30 to indicate that all data for the last data request has now been sent to the remote monitoring station 50. In this context, a data request includes a request for threshold alarms, session data, or events. A status field in this command indicates the reason for the base station unit 30 to stop transmission of Return records.

A DataReturn command packet from the base station unit 30 contains data as requested via a DataRequest command. Different data record types will have different data sizes.

A SetAlarm command from the remote monitoring station 50 is used to set up a threshold alarm monitor on the base station unit 30. A duration parameter indicates for how many seconds the threshold must be exceeded before the alarm is triggered. A hysteresis parameter defines a boundary around the threshold that needs to be crossed before the alarm triggers or resets.

An AlarmDataRequest command from the remote monitoring station 50 requests that the base station unit 30 send all alarms recorded between the Start and End times supplied. The data actually is returned as a series of "Alarm" commands, followed by a ReturnComplete message.

A RemoveAlarm command from the remote monitoring station 50 causes the base station unit 30 to stop monitoring for the specified alarm. This command can only be used to stop monitoring for an alarm that was configured using the SetAlarm command.

An Alarm command packet from the base station unit 30 encapsulates an alarm and returns an Alarm ID to the remote monitoring station after the SetAlarm message.

A SetEventMeasurement command message from the remote monitoring station 50 requests that the base station unit 30 makes an auxiliary measurement. If the alert time is outside the range defined by the start and end times, no user alert is sent. If a periodic flag is set, the measurements are made daily, and the date portion of the start, end, and alert times are ignored.

An EventReading command from the base station unit 30 contains the results of a scheduled auxiliary measurement, as requested by the SetEventMeasurement command. Data valid flags are used to indicate the nature of the data contained in the measurement.

An EventDataRequest command message packet from the remote monitoring station 50 contains a request for event data specified for the specified time range. The response is a series of EventReading command packets followed by a single ReturnComplete command.

A TestRequest command is sent by either end of the communications link 85 and is used to test the link between the two systems. A TestRequest command should result in a TestResponse packet within 3 seconds in a preferred embodiment.

A TestResponse command packet is sent in response to the TestRequest command packet and may include a copy of the data accompanying the TestRequest message.

Of course, other commands may be added as system features are added. Moreover, it is desired that the vital signs data be compressed for faster data downloading to the remote monitoring station 50.

III. Collecting/Managing Data Using Remote Monitoring Station

A. Monitoring Software

Figure 11:
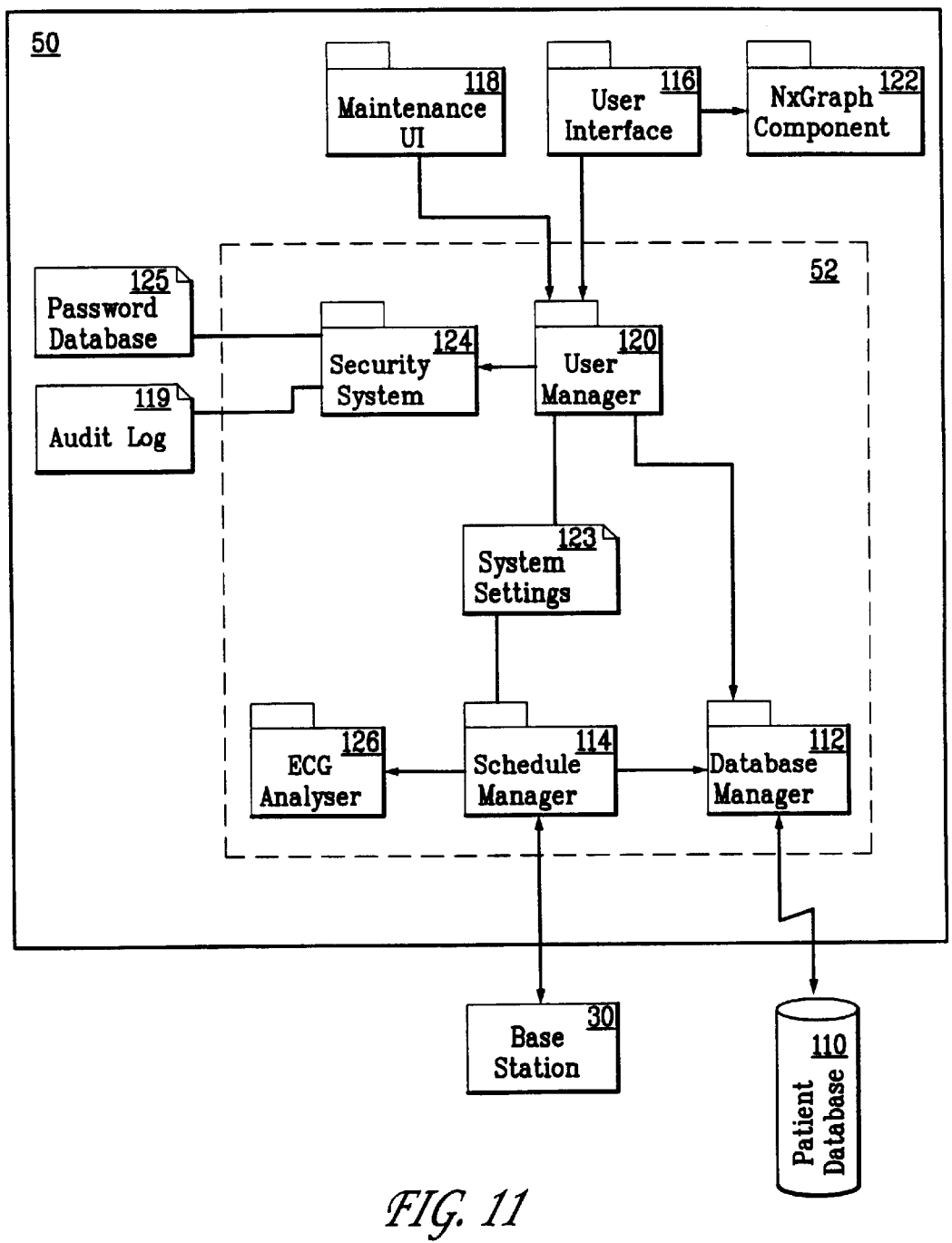
FIG. 11 illustrates the architecture of software of the remote monitoring station.

FIG. 11 illustrates the functional or software architecture of the remote monitoring station 50. As noted above, remote monitoring station 50 is utilized by a health care professional to evaluate the vital signs data received from one or more patients and to perform control functions and maintenance functions necessary for system operation. FIG. 11 illustrates an embodiment of FIG. 5B in which the remote monitoring station 50 includes a server 52 for managing the processing of the vital signs data received from the base station units 30. A similar functional arrangement would be utilized for implementing the embodiment of FIG. 5A except that the server would be located in a separate physical unit or at a remote location. Each of the components of FIG. 11 will now be discussed in turn.

The remote monitoring station 50 maintains a database 110 of patient data received from each patient taking part in a study using the techniques of the invention. In a preferred embodiment, the patient data includes a patient number which is unique for possibly linking to other patient information systems and a telephone number for the patient's base station unit 30. Preferably, additional information is maintained for each patient case which is linked to the patient information. Such information may include current medications taken by the patient, current diagnosis information, base station ID, settings used to obtain data from the base station unit 30 and auxiliary sensors, and the like.

The software of the remote monitoring station 50 maintains the patient database 110 and allows the operator to access such data for analysis and processing. As illustrated in FIG. 11, database manager 112 manages all interactions with the patient database 110. Database manager 112 runs as a continuous background process to ensure that data can always be stored on arrival. The main interface is with the database management system used for the patient database 110; all other interfaces involve extraction of information from the patient database 110.

Schedule manager 114 is responsible for all interactions with the base station unit 30 and, like the database manager 112, runs continuously as a background process. Since information about the required schedules for patient studies is stored in the patient database 110, the schedule manager 114 must obtain all relevant schedule information from the database manager 112. Similarly, the schedule manager 114 passes all data to be stored (i.e. case session data, case alarm data) to the database manager 112 for storage in the patient database 110. The schedule manager 114 interfaces with the rest of the system through the database manager 112. The schedule manager 114 also needs to interface to any modems used to connect to base station units 30. Schedule manager 114 further implements the base station-remote monitoring station communications protocol described in the previous section.

The main user interface 116 provides all normal user interaction with the remote monitoring station 50. In the preferred embodiment, the user interface 116 has no customization or set-up options; all such functionality is provided by the system maintenance user interface 118. User interface 116 is designed to interface with the user manager 120, which maintains current state information and the like. However, some components may interact via different routes for efficiency if this is felt necessary (e.g. the schedule manager 114 may interface directly for live display). Preferably, the user interface 116 embeds instances of the graphics control process 122 for controlling the display of graphical data.

The system maintenance user interface 118 provides control over any configurable parameters. In the preferred embodiment, an interface to the audit log 119 is provided from the system maintenance user interface 118 so that the operator may view the audit log. Preferably, settings that cause changes in visual elements (e.g. graphs) will provide a preview so that the user does not need to keep switching between the two modes. System maintenance user interface 118 also interfaces with the user manager 120, which maintains state information and the like.

User manager 120 maintains state information about a single client user session. The coupling of user manager 120 to user interface 116 depends on the implementation methods actually used. Preferably, user manager 120 obtains a user name and password from the user and then activates either the user interface 116 or the system maintenance user interface 118 depending on the privilege level of the user. User preferences and other settings are read from the system settings object 123. The user manager 120 also accepts connections from graphics objects 122 and supplies the necessary graphical data on demand.

The security system 124 maintains a secure database of user names and passwords used to access the system. There are two levels of user: user and administrator, which are mutually exclusive. In the preferred embodiment, the security system 124 maintains the user database files in an encrypted format. The user manager 120 validates users via password database 125 before continuing using a query to the security system 124.

Finally, an ECG analyzer 126 is provided to analyze in one second chunks any ECG signals passed to it. The processed data is output in a form that can be stored back in the patient database 110. Generally, the ECG analyzer 126 processes data as a complete session. ECG analyzer 126 preferably interfaces to the database manager 112 to perform the ECG analysis and to flag events in the vital signs data as it is uploaded. Generally, the ECG analyzer 126 performs arrhythmia analysis by searching for ventricular fibrillation (VF) and/or typing QRS complexes as normal, ventricular ectopic beat (VEB), SVEB, or artefact. ST analysis may also be performed to check for ST segment elevation, depression, and the like.

If an arrhythmia event is found by ECG analyzer 126, the operator may choose to upload additional patient data around the arrhythmia event, send a warning message to the patient via the communications link 85 to cause the buzzer on the signal transfer unit 20 to sound, or the patient may be called in for evaluation. Generally, since the review is typically performed several hours after the data is collected, the event is noted and the patient is contacted off-line.

Other functions of these software components may include the following:

1. Scheduling Data Acquisition

Scheduling of downloads, and actual data downloads may well occur at different times. In addition, a system may be managing many patients, yet only has access to a single phone line. Therefore, this aspect of the system will behave independently from the user interface.

Generally, download scheduler 114 will use the case properties to download data from the patient base station units 30. The information that the user can specify for a patient's schedule is as follows:

| | |
|---|---|
| Monitoring days | The days of the week on which monitoring is to occur |
| Monitoring times | Either 4 specific times of day that monitoring will occur, or a periodic interval (e.g. 6 hours) and a starting time. |
| Monitoring duration | How long to monitor per session |
| Download days | The days of the week on which downloads are to be performed |
| Download time | The time at which a download should be performed |

The download scheduler 114 should be aware of the download bandwidth available to it, so that estimates of download times can be presented to the user. This can be refined based on actual data transfer times experienced by the system.

Preferably, the download scheduler 114 will support multiple modems. If multiple downloads are scheduled for the same time, the download scheduler 114 will order them and perform downloads sequentially (or in parallel if multiple modems are present). Any downloads that fail should be moved to the end of the queue, and retried up to 3 times before failure is reported. Also, any downloads requested immediately by the user preferably will take priority over previously scheduled events, and the user warned of this fact. However, if the data requested does not exist on the base station unit 30, the fact will be audited, and an event raised for that patient, which would be reviewable with all other events on request. If the download is happening interactively, the user will also be notified with a message on the display screen of the remote monitoring station 50. In addition, it is preferred that any data download shall not cause data to be removed from the base station unit 30 such that the same or additional data could be downloaded more than once if necessary (e.g., in the event of a hard disk failure on the remote monitoring station 50 or in the case of a patient informing a physician that he or she felt poorly during the monitoring period at a time for which the data was not scheduled to be downloaded). As noted above, ECG analysis may be performed automatically upon data download, if appropriate.

2. Flagging Events

The following types of event can be set by the remote monitoring station 50 to be flagged by the base station units 30:

| | |
|---|---|
| Temperature threshold | Both high and low, plus an optional time before trigger value |
| HR threshold | Both high and low, plus an optional time before trigger value |
| RR threshold | Both high and low, plus an optional time before trigger value |
| Event 1 | Event button 1 pressed on the signal transfer unit |
| Event 2 | Event button 2 pressed on the signal transfer unit |
| Data not available | Data has been requested by the remote monitoring station 50 that does not exist on the base station unit 30 |

The above events will be stored on the base station unit 30, and new events will be downloaded whenever the remote monitoring unit 50 and base station unit 30 connect.

In addition, the following events will be flagged by the remote monitoring station 50 once data analysis has been performed:

| | |
|---|---|
| BP threshold | Both systolic and diastolic, high and low |
| VEB frequency | as calculated |
| Tachycardia | Onset and finish |
| Bradycardia | Onset and finish |
| Ventricular Tachycardia (VT) | Onset and finish |
| Ventricular Fibrillation (VF) | Onset and finish |
| Asystole | Onset and finish |

3. Data Analysis

The following channels of data may be analyzed: ECG (for both full analysis and heart rate calculation) and respiration (either respiration or bend channels, to produce a measurement of respiration rate). All data analysis is performed automatically on a session whenever results are required, and the results of the data analysis are stored in the patient database 110.

4. Security

For purposes of accountability, and to simplify the user interface for normal users, it is necessary to identify all users with a user name and password. There are two privilege levels, user and administrator. The two levels are mutually exclusive so that it is always necessary to log in as a different user to perform administration tasks. This prevents a normal user from simply giving themselves administration privileges and accidentally changing or accessing certain features.

5. Auditing

It is necessary to audit certain actions performed by the system or by users. The audit record should be kept in audit log 119 (FIG. 1) separate from the patient database 110. Clearing the audit log 119 will only be possible by administrator level users.

A checksum based on file size and modification date is kept in the system configuration, preferably encrypted. If on software start up, the checksum does not match the file, the software should refuse to start until reset by a user with privileged access. In other words, the software will not start until the password is entered. This event will then be logged into the audit log 19. The audit log 19 will consist of entries showing the type of entry, time of occurrence, and the name of the user causing the auditable event (where appropriate). Other event-specific information may optionally be added.

The events to be audited are:
1. Addition of a patient case;
2. Closing a patient case,
3. Re-opening a case;
4. Modification of case properties;
5. Session download;
6. Events triggered;
7. Setting/changing of event settings;
8. Failures to connect to base station units 30;
9. Errors reported by a base station unit 30;
10. Audit log tampering;
11. Data export/import;
12. Data back-up/restoration/archiving; and
13. Adding/removing users.

B. User Interface to Monitoring Software

Figure 12:
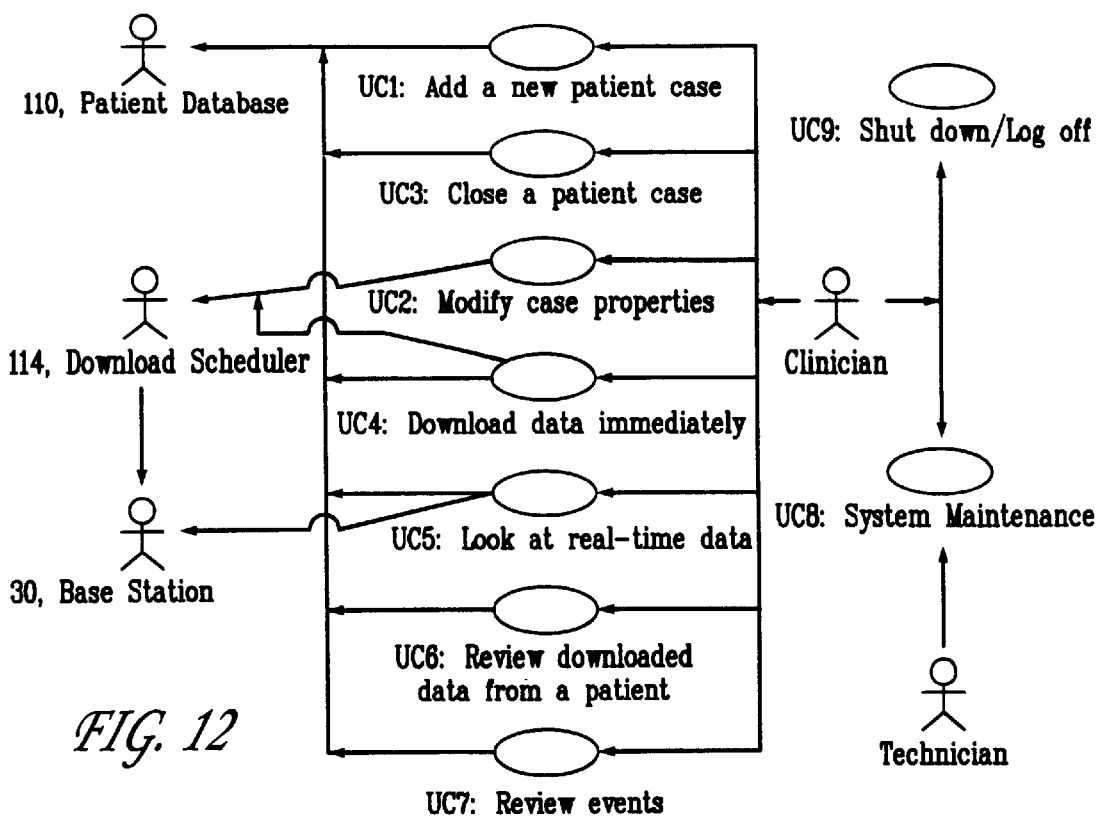
FIG. 12 illustrates a diagram of the top level uses of the remote monitoring station of the invention.

FIG. 12 illustrates a diagram of the top level uses of the remote monitoring station 50 of the invention. As illustrated, such uses include: adding a new patient to be monitored (creating a new patient case), modifying case properties, closing a patient case, downloading data immediately, monitoring real-time (live) data from a patient, reviewing downloaded data from a patient, reviewing events, performing system maintenance, and shutting down/logging off the remote monitoring station 50. The use cases and the user interface of the remote monitoring station 50 used for implementing such use cases will be described in this section. Generally, the remote monitoring station's software communicates with the base station unit 30 via the base station/remote monitoring station protocol described above.

Add a New Patient

For this case, the user is prompted to enter the new patient information, with access to all fields in the patient database 110. On finding a duplicate patient number (not name, as there may be people with the same name in the same system), the user is prompted to either try again, create a new case for that patient or go to Modify Case Properties to modify the current case for that patient. If the patient has closed cases, the option is also given to re-open a case. The patient information is added to the patient database 110 if the patient is a new patient, and the case information is also added to the patient database 110.

Modify Case Properties

Figure 13:
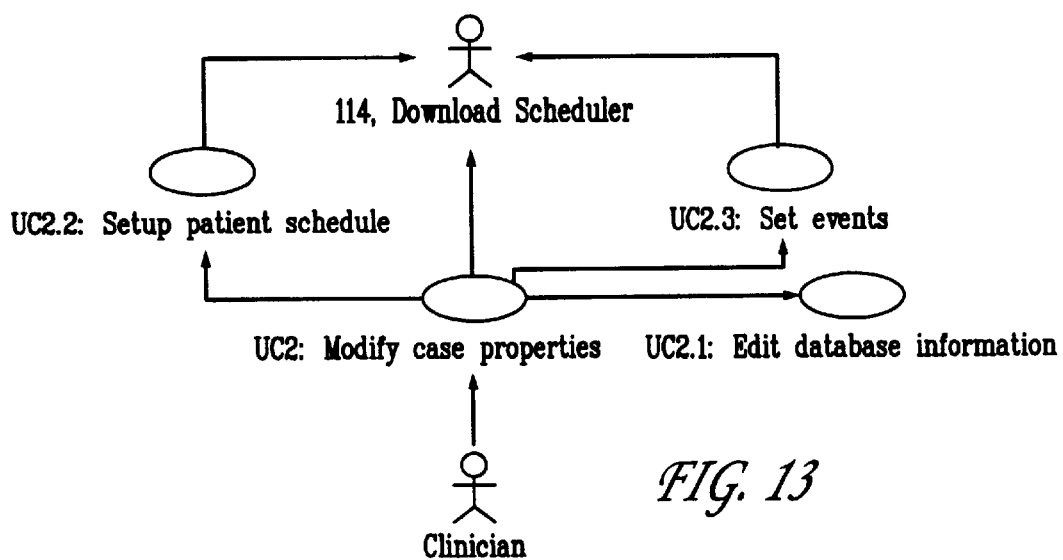
FIG. 13 illustrates the modify case properties process implemented by the monitoring station of the invention.

The user selects the case to modify, and, as illustrated in FIG. 13, the process then splits into the following tasks:

1) Edit Database Information

The user modifies any of the entries in the patient or case record, except the Patient Number and any auto-generated ID fields used to link databases together.

2) Set-up Patient Schedule

This page offers the option to have a look at the current status of the patient. The download properties are entered, with about 3 common defaults accessible from a simple interface, and the current settings (if any) displayed. Some types of download schedules actually result in multiple download instructions being generated, e.g. for downloading 5 minutes per hour over the course of a 24 hour period, with the actual download saved up for a later time. Preferably, download properties are validated, and any conflicts resolved (e.g. if an impossible amount of download time is required). The download properties are then sent to the download scheduler 114. Since some downloads may take an extended period of time, it is desirable that an estimate of the online expected time should be presented when setting download schedules.

3) Set Events

A page showing all possible event types is presented. If none has been set for the current case, all events default to OFF. Each type of event has default parameters that are supplied when it is activated. The events set for this patient case is saved in the patient database 110 with other download information. Changes to the alarm set are audited. Also, each event has associated with it a property that determines if any associated data for a given event is to be downloaded; this specifies the number of minutes data before and after the event to be acquired. This is determined by the remote monitoring station 50, so that the decision to download a session corresponding to an event is made only once an event has arrived at the remote monitoring station 50.

4) Set Auxiliary Sensor Measurements

In a preferred embodiment, the following auxiliary sensors are supported by the base station unit 30: blood pressure (systolic, diastolic and mean), spirometry (FEV1 and PEF), and weight. Measurements are set on an case by case basis; a typical scenario might require 4 measurements per day. A measurement window is defined, outside of which, the measurement is not made. Optionally an alert point (in minutes before the end of the measurement period) is selectable, which causes the patient to be reminded by the buzzer of the signal transfer unit 20. When multiple measurements are required during the same time window, the order in which the patient is required to make measurements is controllable.

Close a Patient Case

The user is asked to confirm that the case should be closed.

Download Data Immediately

Once the user selects a patient case, the user selects the time range of data to download. The user should be warned if this download would conflict with any others currently scheduled or taking place.

Monitor Live Data

The user selects a patient case and establishes a connection with the appropriate base station unit 30. Failure to connect should be reported immediately. Conditions likely to cause failure are: 1) base station unit 30 turned off or not connected, 2) patient is not wearing a disposable sensor band 10 (data not available), 3) phone line is busy, 4) all user phone lines are busy downloading other patient sessions, and 5) the signal transfer unit 20 is out of range of the base station unit 30 (or in catch-up mode). The monitored data is displayed in a real time, smooth scrolling display. When disconnected from the base station unit 30, the user may go to the review downloaded data section to analyze the session just downloaded.

Review Downloaded Data

Figure 14:
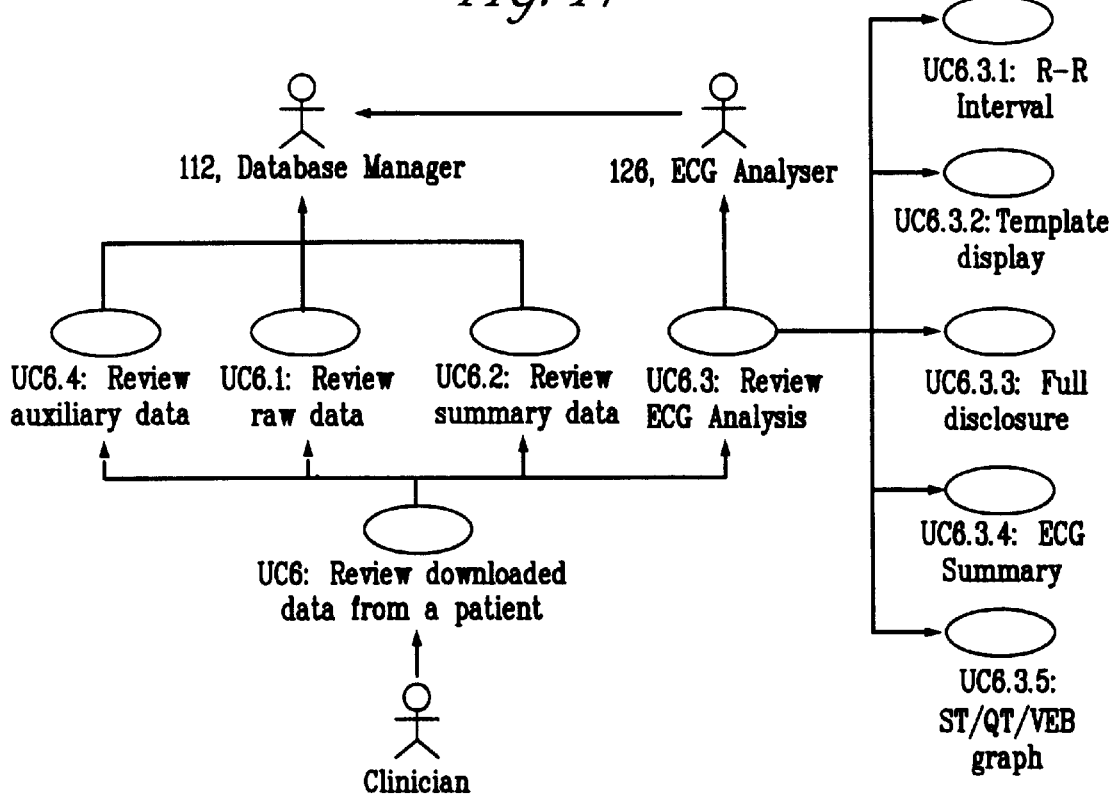
FIG. 14 illustrates the "review downloaded data from a patient" process implemented by the monitoring station of the invention.

FIG. 14 illustrates this use case and its associated subtasks, each of which will be described in turn.

1) Review Raw Data

Once the user selects a patient case, the default display shows ECG, respiration, motion and bend data, with numerical values for heart rate (HR), respiration rate (RR) and temperature. The raw data channels are filtered for display purposes only (filtered data is not stored), and the display time base is selected from 5 seconds, 10 seconds, 20 seconds or 25 mm/sec. Any gaps in the data are shown as gaps in the graphs. System maintenance allows scales to be changed, traces to be added or removed, and colors to be changed. The user has controls to change the time base, to scroll backwards or forwards through the data, to pause the display (but not to stop live acquisition), to stop monitoring and disconnect from the base station unit 30, and to print the current screen. User controls are as for live review, with the additional option to turn the above dynamic scrolling on and off.

2) Review Summary Data

Once the user selects a patient case, data is shown as a page of graphs from the whole session, showing HR, RR, and temperature. The display time base is selectable from 30 minutes, 1 hour, 3 hours, 6 hours, 12 hours and 24 hours. Where the session is smaller than some of these ranges, not all options are available (e.g. 24 hour time base is not available for a 1 hour session). Any gaps in the data are shown as gaps in the graphs. Also, system maintenance allows scales to be changed, traces to be added or removed, and colors to be changed. In addition, the display is interactive, so that selecting a region of the graph allows access to the raw data for that section. This happens in such a way that returning to the summary view is simple (perhaps bringing up a separate window for the raw data, for example).

3) Review/Perform ECG Analysis

Once the user selects a patient case, if the ECG analysis has not already been performed at the time of data download, the user is asked to confirm if ECG analysis should be performed immediately. The entire patient session is sent to the ECG analyzer 126, and the progress through analysis is reported to the user by way of a progress bar. Once completed, the results of the analysis are saved to the session record. The analysis options outlined in the following use cases are presented to the user. By default the summary report should be shown when analysis is complete.

The user is offered the ability to display a histogram of R—R intervals in the analyzed data. Also, a template display is provided which displays a page with the top 12 beat types, including the number of each type and the percent of total beats. The beats shown are one actual beat from the raw data, including its time. The user is permitted to navigate forwards and backwards through the different occurrences of that beat type in the raw data. The user may go to the section of data corresponding to a given beat; such a display is in the "full disclosure" format where a trace is displayed with the same basic properties as the raw data graphs. Additionally, the ECG trace is labeled with all classified beats and rhythms identified by the ECG analyzer 126. A summary report of the results of ECG analysis is generated.

The user has simple access to print out a report. On the other hand, the ST/QT/VEB graph of ST Level, QT Interval, and VEB frequency and heart rate, plotted against time for the entire session may be available.

4) Review Auxiliary Data

This routine displays a graph of data acquired from the auxiliary sensors at the base station unit 30. If no data exists for one of the auxiliary sensor types, no axes are drawn for that sensor. Graphs plotted are blood pressure (with systolic, diastolic and mean plotted on the same set of axes), FEV1 and PEF (highest of three readings plotted on different axes) and weight. All data points for a given series are joined by lines. Time base range is selectable between 1 week, 1 month, 3 months and 6 months.

Review Events

Figure 15:
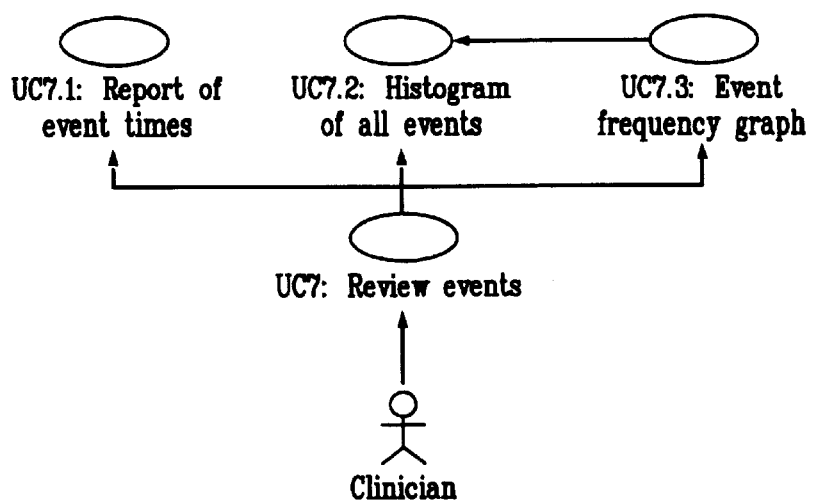
FIG. 15 illustrates the "review events" process implemented by the monitoring station of the invention.

Specific event analysis is always performed on an event for a single patient. The user is asked the time period during which to review an event. The default is the last 7 days. FIG. 15 illustrates an analysis of the applicable alarms.

1) Report of Event Times

This report is the simplest and simply lists, in a text based form, the events that have occurred in the specified period. Information listed includes the time the event was triggered, the type of event, and the cause of the event (e.g. high threshold triggered). The only customization is the ability to selectively show event of a particular type or all events. The default is to show all events.

From a given event, it is possible to go to the data associated with it. For certain events, the data will have automatically been downloaded with the event itself; for others, the data may be included in an already downloaded session. In the remaining case, where there is no data associated with an event, the user is prompted to download the associated data.

2) Histogram of All Events

This report shows a histogram spanning the selected time period, showing the number of events of each type that occurred. The histogram columns are determined by the events selected for the patient. Threshold events will give rise to 2 columns each, one for high trigger, the other for low trigger.

3) Event Frequency Graph

This report shows a graph plotting the total number of events per 15-minute interval against time. The graph is interactive in that selecting a point on the graph will open up a histogram, but with the data taken only from the selected 15-minute period.

C. Use of Remote Monitoring Station Software

Use of the remote monitoring station software will now be described with respect to the user interface screen displays of FIGS. 16 and 17.

To use the remote monitoring station software, the user logs in by entering a valid user name and password into a log in screen. Unless the user is a technician desiring to perform system maintenance, the user also ensures that the option "I want to monitor patient data" is selected. Once logged in, the user selects a patient using a choose patient screen. A patient can be found by using the patient number, study code, patient initials, or any combination of these by entering the data and selecting a "Find" button. If the user desires to see a list of all patients, the user selects a "Select from all patients" button. On the other hand, if the user wishes to work with a new patient who has no record in the system, the user selects an "Add new patient" button. If no patients meet the search criteria, the user will be given a warning message. If the search resulted in just one patient, then the patient information will be shown in the "Case Home Screen" described below. However, if the search resulted in more than one patient, then the user will be shown a list of patients. The user selects the desired patient from the list and clicks on a "View selected patient" button. If the desired patient is not in the list, the user may select a "Go Back" button to try another search.

Figure 16A:
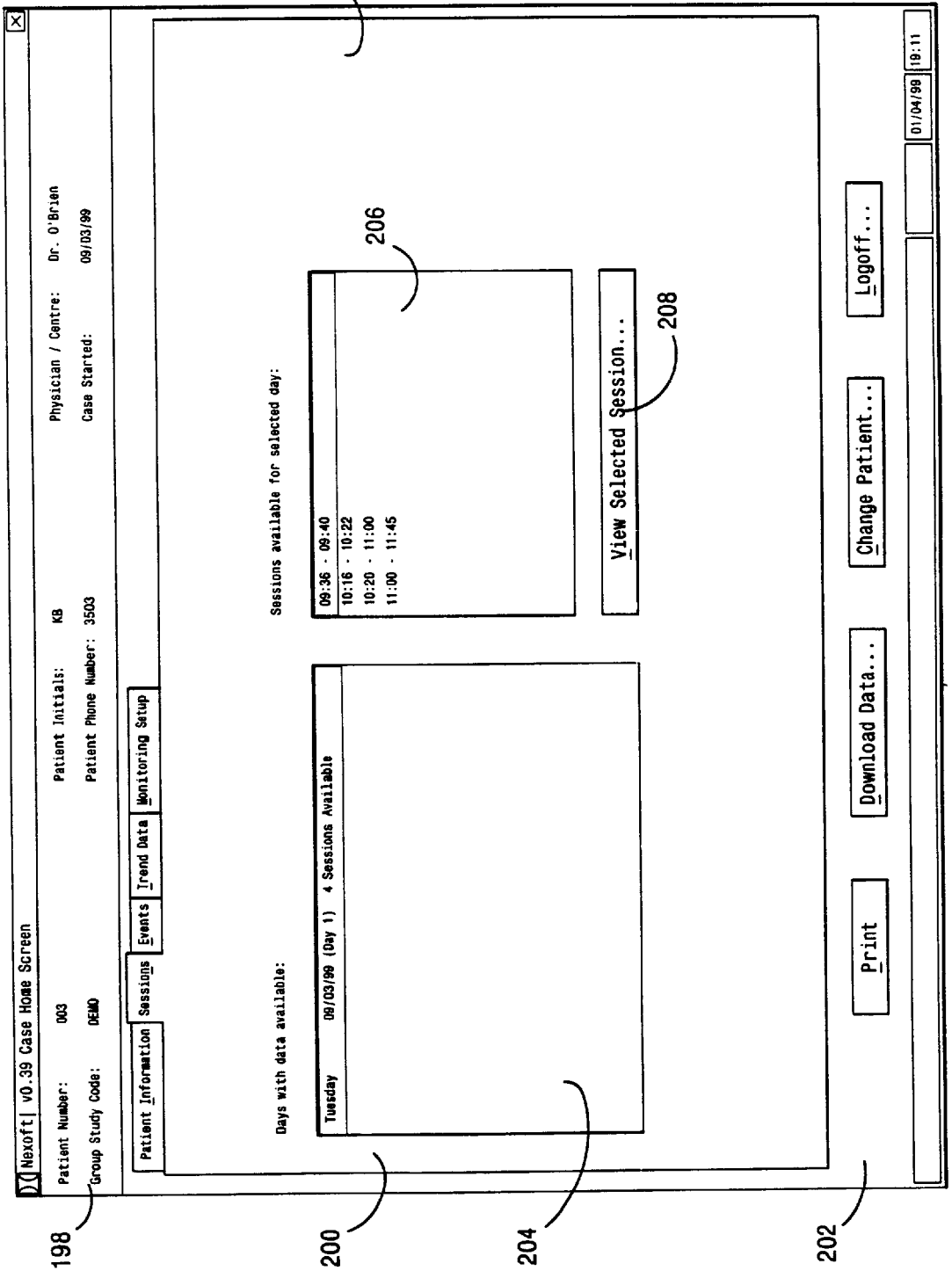
FIG. 16A illustrates the case home screen with the sessions available for the selected patient.

Once a patient has been selected, the patient's data is loaded into the case home screen 196 illustrated in FIG. 16A. As shown, the case home screen 196 is divided into three areas: a portion 198 providing information relating to the currently selected patient and study case, a portion 200 listing a number of tabs that allow the user to look at various different configurations as well as to select different sessions of data, and a portion 202 including buttons for allowing the user to print various screens, download the patient data, and to change the currently selected patient.

In order to navigate among the various options, the user selects one of the tabs in portion 200.

Upon selecting the "Sessions" tab, the user sees the boxes 204 and 206 of FIG. 16A. A list of days with sessions available is displayed in box 204, and a list of different times of the sessions is shown in box 206. The user selects a day from box 204 and one of the corresponding session times from box 206. The user then selects the "View selected session" button 208, and the session data is then loaded and displayed to the user.

Figure 16B:
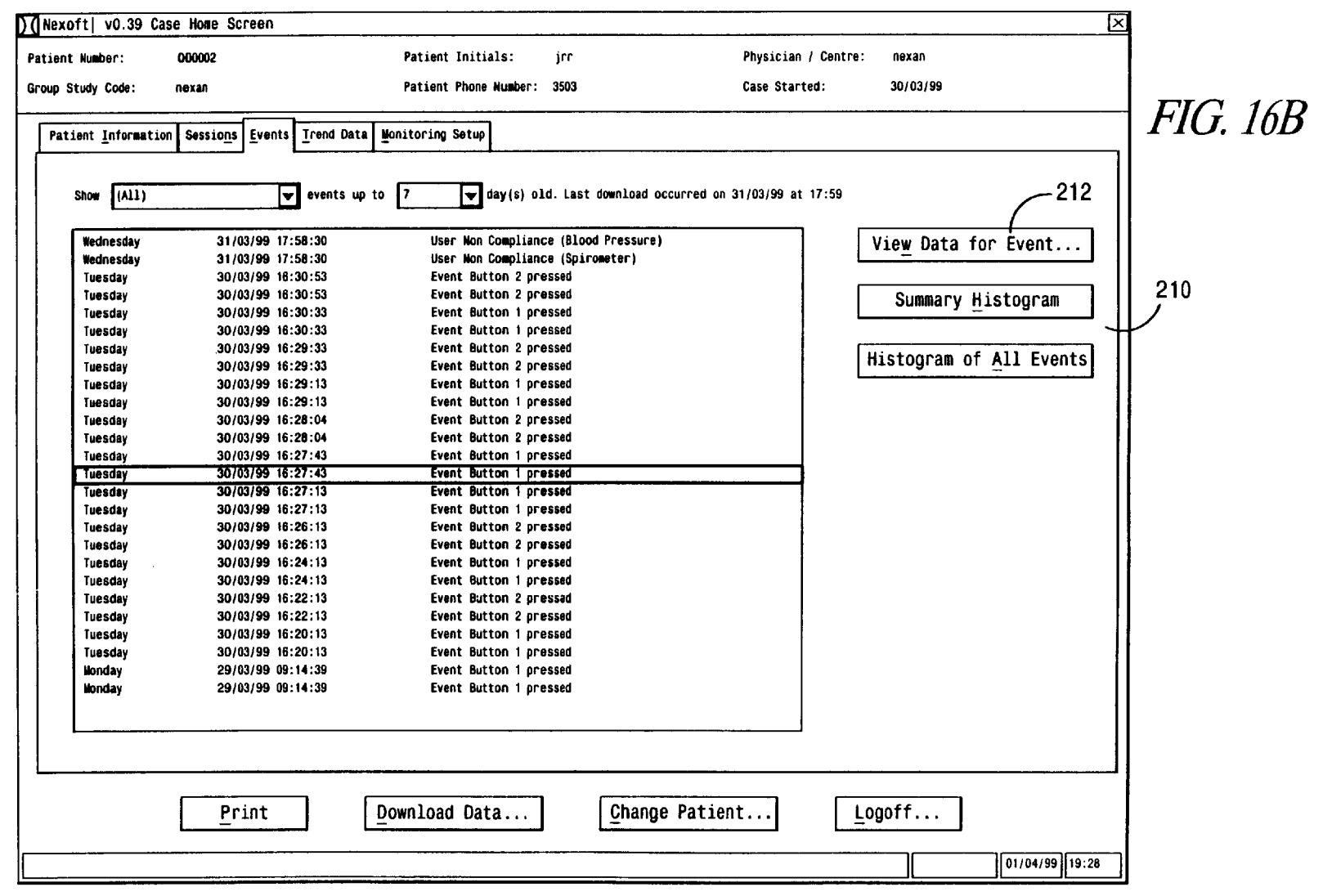

FIG. 16B illustrates the events screen 210 which appears when the "Events" tab is selected. As illustrated, the events screen 210 lists the events that have occurred over a period of time. The use may select what type of event is shown (or elect to show all events) and over what period of time the events are to be collected. The user also receives an indication of when the last download of patient data occurred. To view the monitored data associated with an event, the user selects the event from the list and selects the "View data for event" button 212. The data is then loaded and displayed to the user.

FIG. 16C illustrates the monitoring screen 214 which appears when the "Monitoring Setup" tab is selected. Monitoring screen 214 gives a number of configuration options which allow the user to change the way in which the selected patient is monitored. The top half of the monitoring screen 214 allows the user to change when and for how long the patient is monitored, including which days, the time of day, and for how long the patient will be monitored. The user may select up to 4 fixed times in which to monitor or elect to monitor on a periodic basis, such as every 6 hours. The next part of the monitoring screen 214 allows the user to configure the time of day that the application will automatically call the patient's base station unit 30 to download the patient data from the base station unit 30 to the remote monitoring station 50. The bottom part of screen 214 allows the user to setup which events should be monitored and the thresholds for these events. The user may also configure how much data on either side of the event should be downloaded in the next scheduled download.

As desired, electronic case record forms (CRFs) may also be generated directly from the data stored in the remote monitoring station 50 for each patient by CRF generating software, thereby greatly simplifying the reporting process for drug trials and the like. An electronic CRF would dictate a schedule for the patient's therapy via setup of the base station unit 30 by the remote monitoring station 50. The specified vital signs data could then be collected and inserted into the electronic CRF for management of a drug trial's results and submission of the results for FDA approval and the like, as necessary.

Figure 16D:
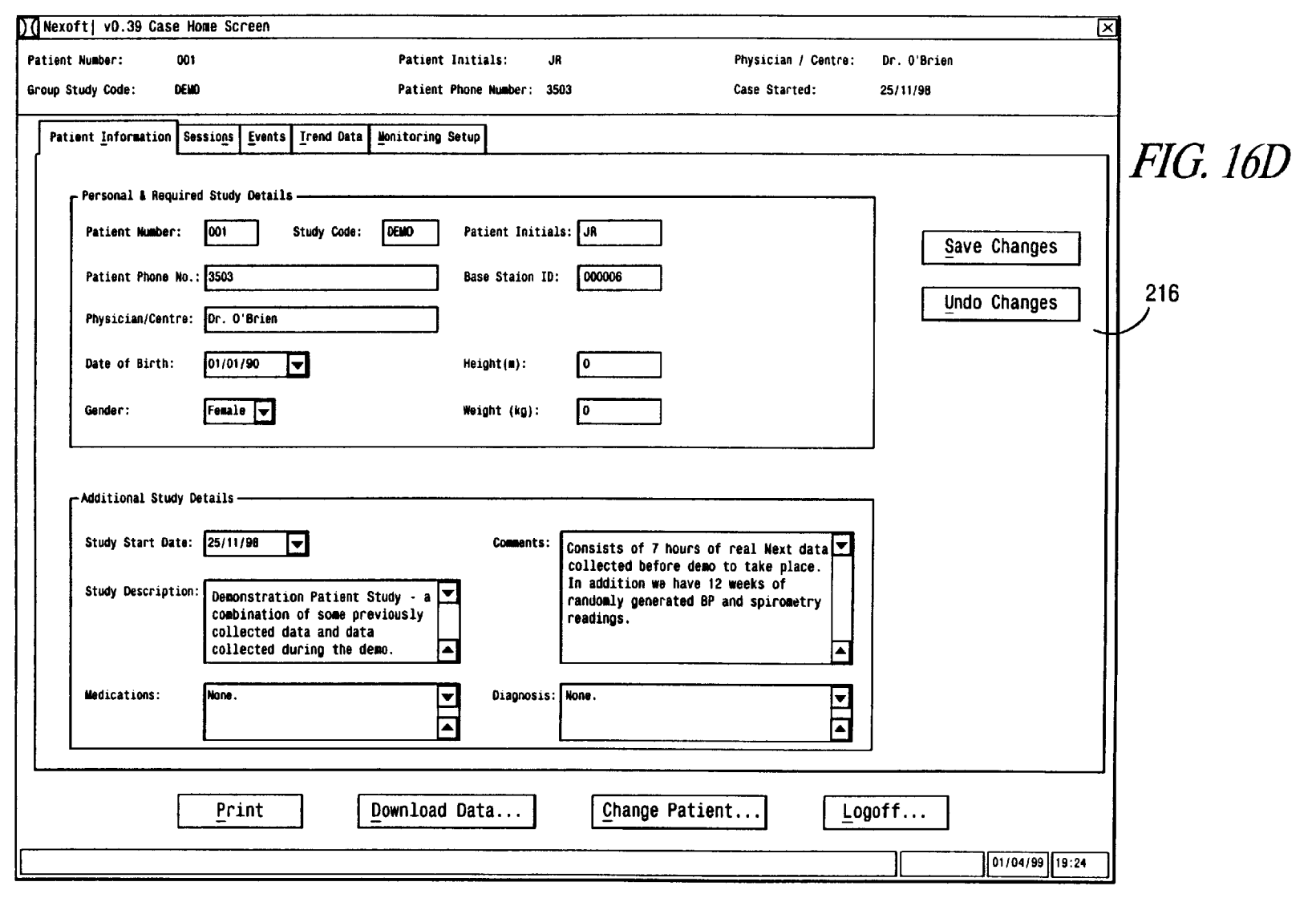

FIG. 16D illustrates the patient information screen 216 that appears when the "Patient Information" tab is selected. Patient information screen 216 displays all information relating to the patient and permits the patient information to be updated. The patient phone number is the telephone number that the application will use to call the base station unit for downloading the monitored data.

Figure 16E:
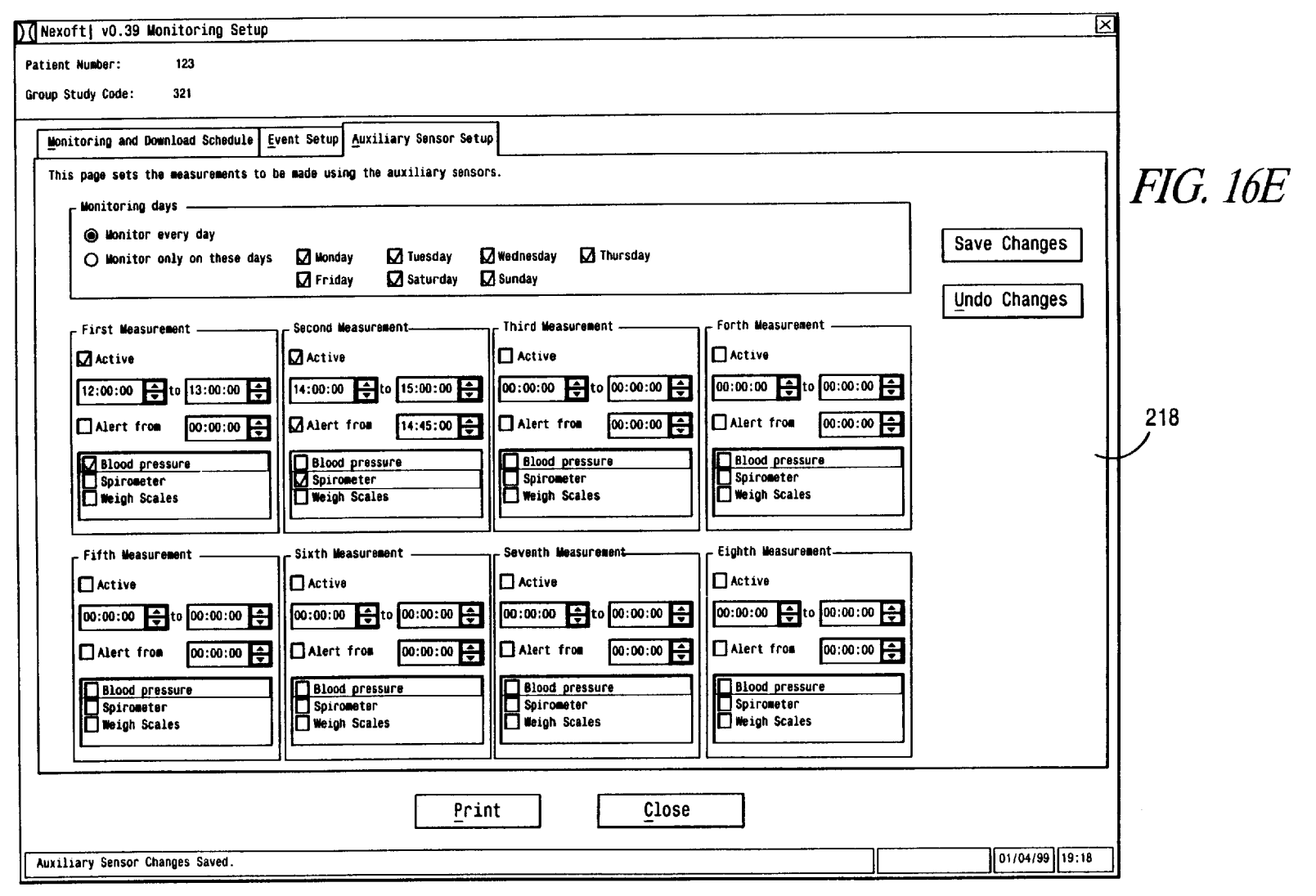

FIG. 16E illustrates the auxiliary sensors screen 218 that appears when the "Auxiliary Sensors" tab is selected. Auxiliary sensors screen 218 displays a number of configuration options that allow the user to change the way in which the auxiliary sensor measurements are taken at the base station unit 30. The top part of the auxiliary sensors screen 218 allows the user to setup on which days the auxiliary sensor measurements are taken, while the rest of the auxiliary sensors screen 218 allows the user to configure up to 8 different measurements to be taken each day. The user simply selects "Active" in the checkbox and then specifies the time period in which the measurement must be taken. The user may also tell the base station unit 30 to alert the patient by selecting the "Alert from" checkbox and specify the time at which this alert should take place. As noted above, the alert may be a light and buzzer on both the base station unit 30 and the signal transfer unit 20. Finally, the user selects the type of measurement from the list of available auxiliary sensors (e.g. blood pressure) to be used during the measurement.

Figure 16F:
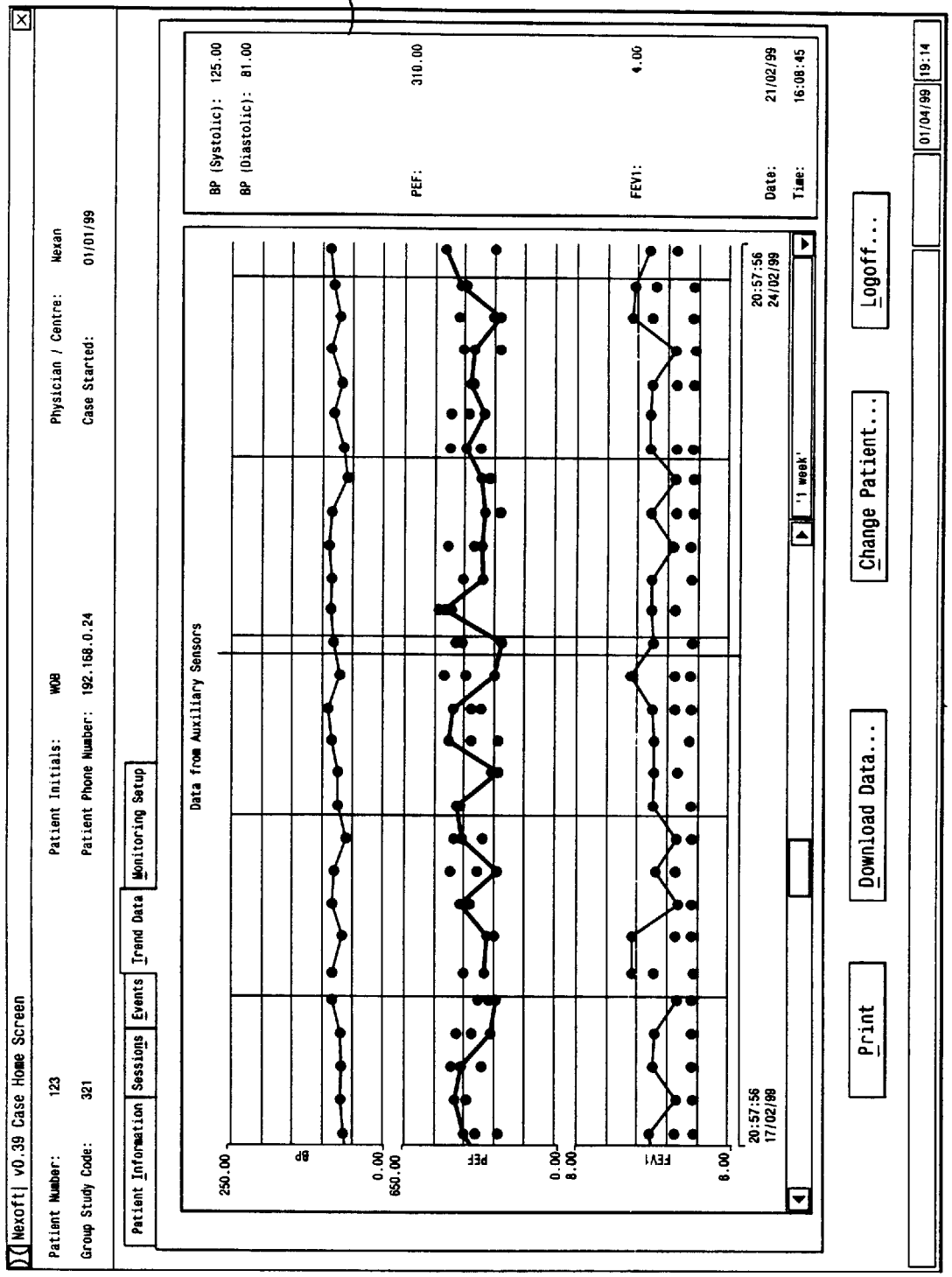
FIG. 16F illustrates the trend data screen for displaying auxiliary sensor data available for the selected patient.

FIG. 16F illustrates the trend data screen 220 that appears when the "Trend Data" tab is selected. Trend data screen 220 displays the readings taken from the auxiliary sensors during the study case. The layout varies depending on which auxiliary sensors are in use for a given patient.

As illustrated in FIGS. 16A–16F, the user is given the option of printing a report for the currently selected tab, to download data immediately from the base station unit 30 in order to view live data (if available) or previously recorded data, to change patients, or to exit.

Figure 17:
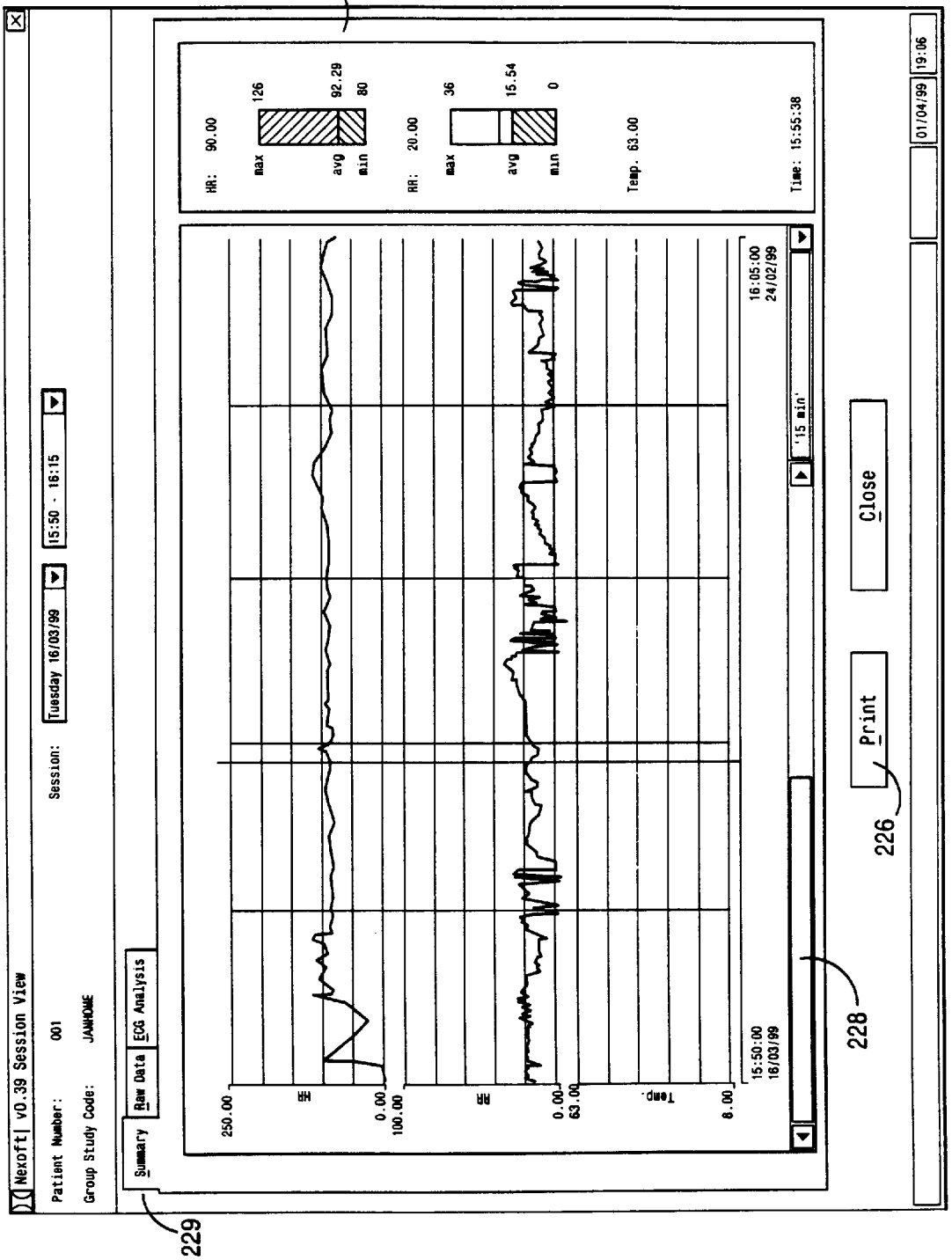
FIG. 17 illustrates the summary graphs for heart rate, respiration and temperature when the summary button is selected.

When the user has selected a patient session to view from the case home screen 196, the session data is loaded into a session view screen 222 of the type illustrated in FIG. 17. As illustrated in FIG. 17, the session view screen 222 provides session information and allows the user to change the session to be viewed, provides a set of tabs 224 from which to select to view either raw, summary or ECG data, and provides buttons 226 to allow the user to print various screens and to close the session view screen 222.

FIG. 17 illustrates the summary graphs for heart rate, respiration and temperature when the summary button is selected and provides a way for the user to look at the data over a larger range of time (i.e., hours instead of minutes). Control buttons 228 allow the user to move the cursor along the graph and to view the graph at different time scales. On the other hand, the user may manipulate the cursor with a mouse to move the cursor along the graph. A scroll bar 228 at the bottom allows the user to view the graphs at different times. Also, the user may select the "Raw Data" tab to review raw data over a smaller range of time or select the "ECG Analysis" tab to view the ECG analysis data for the current session. The user may select from among the types of ECG analysis available, and the system will display the analysis report.

Remote, electronic capture of multiple and continuous vital signs data and transmission of this data in accordance with the invention has the following benefits:

1. Reduction in study costs by replacing expensive clinic visit measurement with domiciliary data capture.
2. Reduction in the number of patients, study time and/or clinic visits required in drug trials through the availability of repeat data, offered by repeat at-home monitoring.
3. Increased safety and improved follow-up of patients provided by domiciliary monitoring.
4. Better management of patients with chronic diseases, with continuous or semi-continuous monitoring, enabling therapy regimes to be refined on an individual basis and possibly preventing acute episodes or deterioration.
5. Increased volumes of patient data for more informed patient diagnoses.
6. The capability to simultaneously capture multiple vital signs data, for example, blood pressure and ECG as defined by study or treatment protocol.
7. The ability to develop predictive algorithms to facilitate more effective treatment protocols by monitoring continuous parameters and comparing patterns with those collected from collections of other patients with similar conditions.
8. Greater speed and simplicity in data handling provided by electronic data capture.
9. Simple, easy-to-use technology (cordless, non-obtrusive design, ideal for night-time monitoring).

In short, the present invention provides more data, earlier, and at a lower cost than current telemonitoring systems. In addition, the ability to monitor the patient continuously for several days means that parameters such as duration of drug effect, drug-drug interactions and safety, which are difficult to measure/monitor at present, may now be measured in a domiciliary setting thereby optimizing drug or other therapies. In particular, the system of the invention permits closed loop control of drug presentation to the patient, whereby the physician may directly monitor the effects of adjusting drug dosages. Also, the system is designed to be very user-friendly, both from the patient's and the physician's perspectives, offering substantial advantages in patient compliance as compared to current telemetric monitoring methods.

Although an exemplary embodiment of the invention has been described in detail above, those skilled in the art will readily appreciate that many additional modifications are possible in the exemplary embodiment without materially departing from the novel teachings and advantages of the invention.

For example, data processing such as ECG analysis could be performed at the base station unit 30 and only the summary data transmitted to the remote monitoring station 50, thereby reducing download times considerably. Also, a radio receiver may be provided to the patient for attachment to his or her computer for use in downloading software and uploading data from/to an Internet server for connection to a predetermined remote monitoring station connected to a designated node on the Internet. This approach would eliminate the need for (and cost of) a separate base station. If auxiliary sensor functions were still required, connections could be built into the radio receiver unit. In addition, a low bandwidth version of the invention may also be developed by tailoring the signal from the sensor band 10 so as to leave out unnecessary data. Also, two-way communication with the sensor band 10 may also be provided. In accordance with another aspect of the invention, the received event data from several patients may be prioritized for patient management (triaging) using the techniques of the invention.

All such modifications are intended to be included within the scope of this invention as defined in the following claims.

What is claimed is:

1. A health parameter data collection and monitoring system, comprising:
    a sensor band having a sensor assembly for application to a subject, said sensor assembly producing a data signal including health parameter data indicative of values of at least one health parameter of the subject, said sensor band further comprising a transmitter which transmits said data signal over a first communications link;
    a transceiver coupled to said first communications link so as to receive said data signal for retransmission over a second, wireless communications link;
    a base station unit disposed so as to receive said retransmitted data signal from said transceiver via said second communications link, said base station unit storing received health parameter data for retransmission over a third communications link; and
    a remote monitoring station disposed so as to receive said retransmitted data signal from said base station unit via said third communications link, said remote monitoring station storing and displaying said health parameter data.

2. A system as in claim 1, wherein said sensor band is adapted for attachment to a chest of the subject and said sensor assembly produces health parameter data indicative of at least one of ECG, respiration, skin temperature, and subject motion.

3. A system as in claim 1, wherein said sensor band includes a circuit which multiplexes health parameter data signals from at least two different sensors in said sensor assembly for transmission over said first communications link by said transmitter.

4. A system as in claim 1, wherein said transceiver comprises a buffer which stores health parameter data received from said sensor band at least during times when said second communications link is disconnected, lost, or unreliable.

5. A system as in claim 1, wherein said remote monitoring station requests retransmission of said data signal to said remote monitoring station at predetermined times or conditions or on demand.

6. A system as in claim 5, wherein said remote monitoring station includes an interface which allows a user to set said predetermined times or conditions for said retransmission of said data signal to said remote monitoring station.

7. A system as in claim 6, wherein said interface allows the user of the remote monitoring station to select a subject for review of at least that subject's health parameter data.

8. A system as in claim 6, wherein said interface allows the user to simultaneously review and compare time synchronized health parameter data for a plurality of health parameters for a particular subject.

9. A system as in claim 6, wherein said interface permits the user to select at least one of unprocessed health parameter data and summary data for display to the user of the remote monitoring station.

10. A system as in claim 1, further comprising a database accessible by said remote monitoring station to store health parameter data for a plurality of subjects.

11. A system as in claim 10, wherein said remote monitoring station includes software which generates case record forms from at least the health parameter data stored for a subject in said database.

12. A system as in claim 1, wherein said transceiver is adapted to receive health parameter data transmitted by at least two sensor bands for retransmission to said remote monitoring station.

13. A system as in claim 1, wherein said base station unit includes a processor which calculates physiological parameter data including at least one of a subject's heart rate and a subject's respiration rate from said health parameter data and stores said physiological parameter data in a memory for transmission to said remote monitoring station.

14. A system as in claim 13, wherein said memory of said base station unit is a rolling first-in-first-out (FIFO) memory which stores said health parameter data irrespective of whether said health parameter data has been transmitted to said remote monitoring station.

15. A system as in claim 1, wherein said base station unit comprises at least one input connection for accepting auxiliary data input parameters from an auxiliary health parameter sensor and a memory which stores said auxiliary data input for transmission to said remote monitoring station.

16. A system as in claim 15, wherein said base station unit time stamps said health parameter data and said auxiliary data synchronously and ages independently said auxiliary data and said health parameter data while stored in said memory of said base station unit.

17. A system as in claim 15, wherein said auxiliary health parameter sensor is at least one of a blood pressure sensor, a spirometer, a weigh scale, and a blood glucose meter.

18. A system as in claim 15, wherein said base station unit detects abnormal physiological conditions in said auxiliary data and indicates an event condition and stores event data indicating a significant physiological event in said memory when an abnormal physiological condition is detected.

19. A system as in claim 18, wherein said base station unit time stamps said health parameter data and said auxiliary data synchronously and ages independently said auxiliary data and said health parameter data while stored in said memory of said base station unit.

20. A system as in claim 15, wherein said base station unit includes a processor which calculates physiological parameter data including at least one of a subject's heart rate and a subject's respiration rate from said health parameter data and stores said physiological parameter data in said memory at said base station unit for transmission to said remote monitoring station.

21. A system as in claim 20, wherein said processor further performs ECG analysis of said health parameter data and stores ECG analysis data in said memory.

22. A system as in claim 20, wherein said memory separately stores said health parameter data and said calculated physiological parameter data.

23. A system as in claim 15, wherein said remote monitoring station includes an interface which allows a user to schedule auxiliary health parameter sensor measurements at said base station unit if such measurements are required.

24. A system as in claim 1, wherein said base station unit comprises a memory and compares received health parameter data with predetermined ranges for detected physiological variables and detects abnormal physiological conditions in said health parameter data, said base station unit indicating an event condition and storing event data indicating a significant physiological event in said memory when said received health parameter data is outside said predetermined ranges or when an abnormal physiological condition is detected.

25. A system as in claim 23, wherein said memory of said base station unit is a rolling first-in-first-out (FIFO) memory which stores at least said health parameter data irrespective of whether said health parameter data has been transmitted to said remote monitoring station.

26. A system as in claim 24, wherein said remote monitoring station includes an interface which allows a user to set at least one of said predetermined ranges of said base station unit.

27. A system as in claim 23, wherein said remote monitoring station includes means for checking received data for event data and an interface which allows a user to view such event data, whereby if event data is detected, said interface allows the user of said remote monitoring station to view a desired amount of health parameter data before, during, and after an occurrence of an event condition indicated by said event data.

28. A system as in claim 1, wherein said second communications link is a bidirectional asynchronous radio link.

29. A system as in claim 28, wherein said transceiver initiates all communications dialogs with said base station unit.

30. A system as in claim 28, wherein said health parameter data is transmitted from said transceiver to said base station unit over said second communications link in data packets including CRC error detection code and ARQ code for the retransmission of erroneous data packets.

31. A system as in claim 30, wherein said data packets are scrambled for transmission in a data packet stream so as to minimize a DC component in said data packet stream.

32. A system as in claim 30, wherein if said base station unit or said transceiver receives two consecutive erroneous data packets over said second communications link, said second communications link will be determined to be disconnected, lost, or unreliable, and said transceiver will wait a predetermined period of time before attempting to re-establish the second communications link with said base station unit.

33. A system as in claim 30, wherein each data packet is one of the following types of data packets: a dialog request packet for initiating a dialog between said transceiver and said base station unit, an acknowledgment packet for informing the sender of the success of a transmitted data packet, a health parameter data packet which includes health parameter data for transfer from said transceiver to said base station unit, and a control data packet for transferring configuration data from said base station unit to said transceiver.

34. A system as in claim 28, wherein said base station unit sends an alarm signal or an indication to a subject to do something to said transceiver via said second communications link when at least one of the following occurs: a physiological event is detected in said health parameter data, it is time for the subject to take a physiological parameter reading or a medication, and the base station unit cannot accept more health parameter data.

35. A system as in claim 1, wherein said third communications link is a telecommunications link.

36. A system as in claim 35, wherein said remote monitoring station initiates a connection with said base station unit, and once the connection is established, said remote monitoring station and base station unit listen for commands.

37. A system as in claim 30, wherein said commands include a data request command from said remote monitoring station requesting at least one of real-time health parameter data and health parameter data in a designated time range from said base station unit.

38. A system as in claim 1, wherein an ID of said base station unit is checked by said remote monitoring station before data is transmitted via said third communications link.

39. A system as in claim 1, further comprising a database accessible by said remote monitoring station to capture and store health parameter data for a plurality of subjects and said remote monitoring station further includes an interface through which a user of the remote monitoring station may select a subject for review of at least that subject's health parameter data.

40. A system as in claim 1, wherein said base station unit is adapted to receive health parameter data transmitted by at least two transceivers for retransmission to said remote monitoring station.

41. A system as in claim 1, wherein said remote monitoring station is adapted to receive health parameter data transmitted by at least two base station units.

42. A system as in claim 41, wherein said remote monitoring station includes a server which controls the receipt and storage of health parameter data from said at least two base station units.

43. A health parameter data collection and monitoring system, comprising:
a sensor band having a sensor assembly for application to a subject, said sensor assembly producing a data signal including health parameter data indicative of values of at least one health parameter of the subject, said sensor band further comprising a transmitter which transmits said data signal over a first communications link;
a transceiver coupled to said first communications link so as to receive said health parameter data for retransmission of said data signal over a second, wireless communications link, said transceiver including a buffer which stores health parameter data received from said sensor band at least during times when said second communications link is disconnected, lost, or unreliable, said transceiver stopping data transmission when said second communications link becomes disconnected, lost, or becomes unreliable, and said transceiver retransmitting said data signal over said second communications link from said transceiver at an increased transmission rate after said second communications link is restored as compared to a transmission rate before said second communications link is disconnected, lost, or becomes unreliable; and
a remote monitoring station disposed so as to receive said retransmitted data signal from said transmitter via said second communication link.

44. A system as in claim 43, wherein said transceiver includes an alarm indicator which warns the subject that said second communications link has been disconnected, lost, or has become unreliable so that the subject may take steps to restore said second communications link.

45. A system as in claim 43, wherein said transceiver includes at least one event button, wherein depression of said event button indicates an event condition and corresponding event data is transmitted to said remote monitoring station.

46. A system as in claim 45, wherein said remote monitoring station includes means for checking received data for said event data and an interface which allows a user to view such that event data, whereby if event data is detected, said interfcae allows the user of said remote monitoring station to view health parameter data before, during, and after an occurrence of the event condition indicated by said event data.

47. A health parameter data collection and monitoring system, comprising:
a sensor band having a sensor assembly for application to a subject, said sensor assembly producing a data signal including health parameter data indicative of values at least one health parameter of the subject, said sensor band further comprising a transmitter having a first antenna which transmits said data signal over a first wireless communications link;
a transceiver having a second antenns inductively coupled to said first communications link so as to form a wireless inductive loop with said first antenna for reception of said health parameter data, said transceiver further retransmitting said data signal over a second wireless communications link; and
a remote monitoring station disposed so as to receive said retransmitted data signal from said transmitter via said second wireless communications link.

48. A system as in claim 47, wherein said data signal is transmitted over said first wireless communications link by said transmitter in QPSK formatted coded data packets.

49. A system as in claim 48, wherein said data packets are transmitted in at least one frequency channel of a plurality of frequency division multiplexed channels spaced at predetermined intervals in a selected frequency range.

50. A system as in claim 49, wherein coded data packets in each of said frequency channels comprise a clock signal, a framing pulse, and said health parameter data.

51. A system as in claim 48, wherein said transmitter includes a controller which codes said coded data packets from template waveforms representative of each possible transition of symbols corresponding to a different phase offset of the transmitted signal relative to a fixed carrier phase locked to symbol transitions.

52. A system as in claim 51, wherein said controller converts each of said template waveforms into respective digital data streams which are, in turn, converted into controller instructions.

53. A system as in claim 52, wherein said controller converts zero-to-one state changes of said template waveforms into controller instructions which set an output port bit of said transmitter, converts one-to-zero state changes of said template waveforms into controller instructions which clear said output port bit of said transmitter, and converts idle periods between state changes into a sequence of no-operation instructions so as to introduce correct time delays between state changes.

54. A system as in claim 53, wherein said controller replaces certain no-operation instructions in said template waveforms by jump instructions which jump into a template waveform to a point which ensures continuity of the coded data packets, said controller further deleting instructions in each template waveform rendered unnecessary by said jump instructions.

55. A system as in claim 54, wherein said controller applies an optimization algorithm to said template waveforms to reduce the length each.

56. A health parameter data collection and monitoring system, comprising:
   a sensor band having a sensor assembly for application to a subject, said sensor assembly producing a data signal including health parameter data indicative of values of at least one health parameter of the subject, said sensor band further comprising a transmitter which transmits said data signal over a first communications link;
   a transceiver coupled to said first communications link so as to receive said health parameter data for retransmission of said data signal over a second, wireless communications link; and
   a remote monitoring station disposed so as to receive said retransmitted data signal from said transceiver via said second communications link, said remote monitoring station capturing said health parameter data and storing said health parameter data in a database with health parameter data from a plurality of other subjects, said remote monitoring station including a user interface which provides access to health parameter data in said database and processing of said health parameter data.

57. A system as in claim 56, wherein said remote monitoring station requests retransmission of said data signal to said remote monitoring station at predetermined times, in response to certain conditions, or on demand.

58. A system as in claim 57, wherein said interface allows the user to set said predetermined times and conditions for said retransmission of said data signal to said remote monitoring station.

59. A system as in claim 56, wherein said interface allows the user of the remote monitoring station to select a subject for review of at least that subject's health parameter data.

60. A system as in claim 56, wherein said interface allows the user to simultaneously review and compare time synchronized health parameter data for a plurality of health parameters for a particular subject.

61. A system as in claim 56, wherein said interface permits the user to select at least one of unprocessed health parameter data and summary data for display to the user of the remote monitoring station.

62. A system as in claim 56, wherein said remote monitoring station further includes means for performing ECG analysis of said health parameter data.

63. A system as in claim 56, wherein said interface requests a password from a user before permitting the user to access said database.

64. A system as in claim 56, wherein said interface keeps an audit record of actions performs by the user when using said interface and of actions performed by said remote monitoring station.

65. A system as in claim 56, wherein said interface formats at least a portion of said health parameter data into a histogram of R—R intervals of ECG data, presents said data to a display upon user request, and permits the user to navigate and select said ECG data for detailed viewing.

66. A system as in claim 56, wherein said interface formats received physiological parameter data into trend data, presents said trend data to a display upon user request, and permits the user to navigate and select said trend data for detailed viewing.

67. A method of collecting health parameter data, comprising the steps of:
   applying a sensor band having a sensor assembly to a subject whereby said sensor assembly produces a data signal including health parameter data indicative of values of at least one health parameter of the subject;
   said sensor band transmitting said data signal over a first communications link to a transceiver which is disposed so as to receive said health parameter data;
   said transceiver retransmitting said data signal over a second, wireless communications link to a base station unit;
   said base station unit storing said health parameter data until a designated time for transmission of said health parameter data to a remote monitoring station; and
   said remote monitoring station receiving said retransmitted data signal from said base station unit via a third communications link and capturing said health parameter data for storage in a database as a continuous record of the subject's health parameters.

68. A method as in claim 67, wherein said sensor band applying step comprises the step of attaching said sensor band to a chest of the subject whereby said sensor assembly produces health parameter data indicative of at least one of ECG, respiration, skin temperature, and subject motion.

69. A method as in claim 67, wherein said sensor band transmitting step comprises the step of multiplexing health parameter data signals from at least two different sensors in said sensor assembly for transmission over said first communications link.

70. A method as in claim 67, wherein said retransmitting step comprises the step of transmitting said data signal over a cellular communications link to said remote monitoring station.

71. A method as in claim 62, wherein said retransmitting step comprises the step of transmitting said data signal over a cellular communications link to said base station unit.

72. A method as in claim 62, wherein said retransmitting step comprises the step of retransmitting said data signal to said remote monitoring station at said designated time, in response to a certain condition, or on demand.

73. A method as in claim 72, wherein said retransmitting step comprises the step of allowing a user to set said designated time and certain condition for said retransmission of said data signal to said remote monitoring station.

74. A method as in claim 72, wherein said step of retransmitting said data signal to said remote monitoring station includes the step of real-time transmission of said data signal to said remote monitoring station on receipt of a demand from said remote monitoring station.

75. A method as in claim 62, comprising the further step of storing said health parameter data received from said sensor band in a buffer of said transceiver at least during times when said second communications link is disconnected, lost, or unreliable.

76. A method as in claim 62, comprising the further step of accessing said health parameter data stored in said database for medical diagnosis or analysis.

77. A method as in claim 76, wherein said step of accessing said health parameter data comprises the step of using the remote monitoring station to select a subject for review of at least that subject's health parameter data.

78. A method as in claim 77, wherein said step of accessing said health parameter data comprises the step of simultaneously reviewing and comparing time synchronized health parameter data for a plurality of health parameters for the selected subject.

79. A method as in claim 76, wherein said step of accessing said health parameter data step comprises the step of permitting the user to select at least one of unprocessed health parameter data and summary data for display.

80. A method as in claim 67, comprising the further step of generating case record forms from at least the health parameter data stored for a subject in said database.

81. A method as in claim 67, comprising the further step of receiving at said transceiver health parameter data transmitted by at least two sensor bands for retransmission to said remote monitoring station.

82. A method as in claim 67, comprising the further steps of determining whether the subject moved during a measurement of said health parameter data and deleting or ignoring health parameter data collected during a time the subject moved if such movement may have corrupted the health parameter data.

83. A method as in claim 82, wherein corruption of the health parameter data is determined by comparing motion data to at least one of an ECG waveform and a respiration waveform.

84. A method of collecting health parameter data, comprising the steps of:
applying a sensor band having a sensor assembly to a subject whereby said sensor assembly produces a data signal including health parameter data indicative of values of at least one health parameter of the subject;
said sensor band transmitting said data signal over a first communications link to a transceiver which is disposed so as to receive said health parameter data;
said transceiver retransmitting said data signal over a second, wireless communications link unless said second communications link becomes disconnected, lost, or becomes unreliable;
said transceiver storing health parameter data received from said sensor band at least during times when said second communications link is disconnected, lost, or unreliable and retransmitting said data signal over said second communications link from said transceiver at an increased transmission rate after said second communications link is restored as compared to a transmission rate before said second communications link is disconnected, lost, or becomes unreliable; and
a remote monitoring station receiving said retransmitted data signal from said transceiver and capturing said health parameter data for storage in a database as a continuous record of the subject's health parameters.

85. A method as in claim 84, comprising the additional step of warning the subject that said second communications link has been disconnected, lost, or has become unreliable so that the subject may take steps to restore said second communications link.

86. A method of remotely collecting health parameter data continuously for at least a day, comprising the steps of:
applying a sensor band having a sensor assembly to a subject whereby said sensor assembly produces a data signal including health parameter data indicative of values of at least one health parameter of the subject;
said sensor band transmitting said data signal over a first communications link to a transceiver which is disposed so as to receive said health parameter data;
said transceiver retransmitting said data signal over a second, wireless communications link;
a remote monitoring station receiving said retransmitted data signal from said transceiver and capturing said health parameter data for storage in a database as a continuous record of the subject's health parameters; and
temporarily buffering said health parameter data so as to prevent data loss in the event of transmission error over said first or second communications links.

87. A method as in claim 86, comprising the further step of providing real-time access to said health parameter data from said remote monitoring station to said transceiver by bypassing said buffering step when real-time data is requested by said remote monitoring station.

88. A method of continuously monitoring a subject's health parameters during a drug/therapy trial, comprising the steps of:
applying a sensor band having a sensor assembly to a subject whereby said sensor assembly produces a data signal including health parameter data indicative of values of at least one health parameter of the subject;
said sensor band transmitting said data signal over a first communications link to a transceiver which is disposed so as to receive said health parameter data;
providing a drug/therapy to the subject and electronically providing event data indicating that such an event has occurred and when;
said transceiver retransmitting said data signal and event data over a second, wireless communications link; and
a remote monitoring station receiving said retransmitted data signal and event data from said transceiver and capturing said health parameter data and event data for storage in a database as a continuous record of the subject's health parameters during a trial period of said drug/therapy, whereby said subject's physiological condition during said trial period may be monitored remotely.

89. A method as in claim 88, comprising the further step of electronically providing event data marking (1) that the subject feels ill and (2) when the subject feels ill.

90. A method as in claim 89, comprising the further step of collecting vital signs data at times before, during, and after the timing of an event marked by said event data and providing a display of any changes in said health parameter data as a result of said drug/therapy or of the subject feeling ill.

* * * * *